(12) United States Patent
Ganz et al.

(10) Patent No.: US 7,406,189 B2
(45) Date of Patent: Jul. 29, 2008

(54) COMPUTER CONTROLLABLE LED LIGHT SOURCE FOR DEVICE FOR INSPECTING MICROSCOPIC OBJECTS

(76) Inventors: Brian L. Ganz, 7057 Leeward St., Carlsbad, CA (US) 92009; John A. Adams, 9785 Running Creek La., Escondido, CA (US) 92026; James Hutchings, 2977 Glenbrook St., Carlsbad, CA (US) 92008; Andrew Provost, 1733 Promenade Cir., Vista, CA (US) 92083-6171; Joseph Gottlieb, 1803 Summit Dr., Escondido, CA (US) 92026; David W. Jewell, 4019 Carmel View Rd., #156, San Diego, CA (US) 92130; Mandel W. Mickley, 1433 Eastview Ct., Oceanside, CA (US) 92056; John Andrew Moulds, 423 Jolina Way, Encinitas, CA (US) 92024; Christopher T. Brovold, 3350 Calle Odessa, Carlsbad, CA (US) 92009

( * ) Notice: Subject to any disclaimer, the term of this patent is extended or adjusted under 35 U.S.C. 154(b) by 918 days.

(21) Appl. No.: 10/627,386

(22) Filed: Jul. 25, 2003

(65) Prior Publication Data

US 2004/0105575 A1  Jun. 3, 2004

Related U.S. Application Data

(63) Continuation-in-part of application No. 09/982,048, filed on Oct. 18, 2001, now Pat. No. 6,985,616.

(51) Int. Cl.
*G06K 9/00* (2006.01)
*H04N 5/222* (2006.01)
*H04N 7/18* (2006.01)
*H04N 9/47* (2006.01)

(52) U.S. Cl. .................. 382/133; 382/141; 348/92; 348/131; 348/370

(58) Field of Classification Search ............... 382/128, 382/129, 133, 141–152, 325; 348/135, 370, 348/371, 92, 131, 132; 356/30; 359/385, 359/390; 377/11
See application file for complete search history.

(56) References Cited

U.S. PATENT DOCUMENTS

| | | | | |
|---|---|---|---|---|
| 4,948,247 A * | 8/1990 | Lapeyre | ............... | 356/23 |
| 5,239,178 A * | 8/1993 | Derndinger et al. | ......... | 250/234 |
| 5,293,428 A * | 3/1994 | Kondou et al. | ............... | 382/146 |
| 5,544,254 A * | 8/1996 | Hartley et al. | ............... | 382/108 |
| 6,205,259 B1 * | 3/2001 | Komiya et al. | ............... | 382/284 |
| 6,207,946 B1 * | 3/2001 | Jusoh et al. | ............... | 250/208.1 |
| 6,368,402 B2 * | 4/2002 | DeTitta et al. | ................ | 117/68 |

(Continued)

*Primary Examiner*—Matthew Bella
*Assistant Examiner*—Yubin Hung
(74) *Attorney, Agent, or Firm*—John R. Ross; John R. Ross, III

(57) ABSTRACT

A device for inspecting microscopic objects. A plurality of LEDS is arranged in an array underneath a lens. Some of the LEDS are lighted and some of the LEDS are unlighted. A computer is in control of the LED array. The computer turns on selected LEDS from the array to form the lighted LEDS. Also, the computer turns off selected LEDS from the array to form the unlighted LEDS. The lighted LEDS form a pattern of lighted LEDS underneath the lens. In a preferred embodiment, the lens is connected to a computer controlled camera and the microscopic objects are microscopic crystals.

24 Claims, 40 Drawing Sheets

U.S. PATENT DOCUMENTS

| | | | |
|---|---|---|---|
| 6,407,858 B1 * | 6/2002 | Montagu | 359/391 |
| 6,621,569 B2 * | 9/2003 | Sones | 356/237.2 |
| 2002/0101197 A1 * | 8/2002 | Lys et al. | 315/291 |
| 2003/0030896 A1 * | 2/2003 | Brooker | 359/368 |
| 2004/0263346 A1 * | 12/2004 | Neal | 340/815.45 |

* cited by examiner

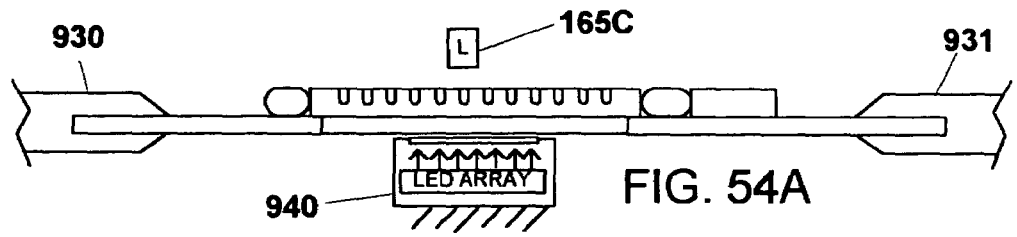
FIG. 54A
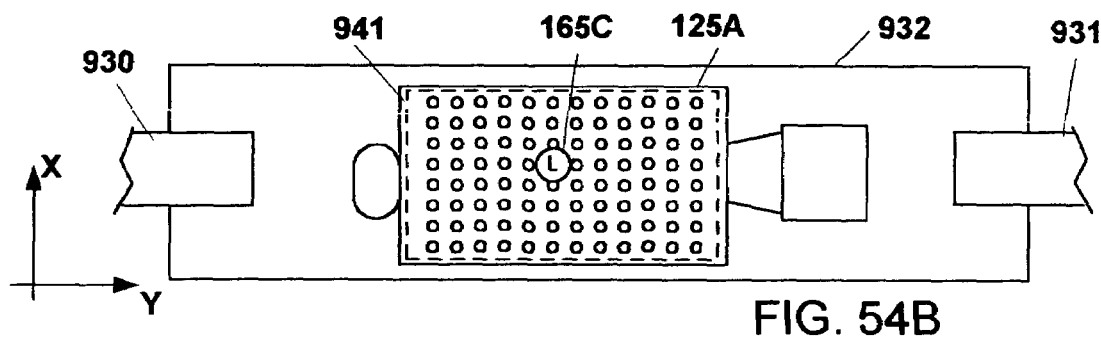
FIG. 54B
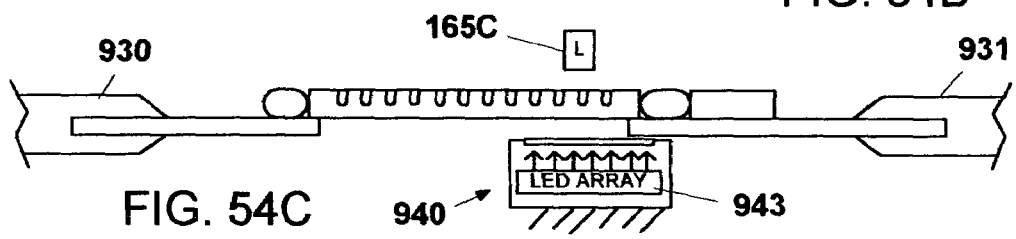
FIG. 54C
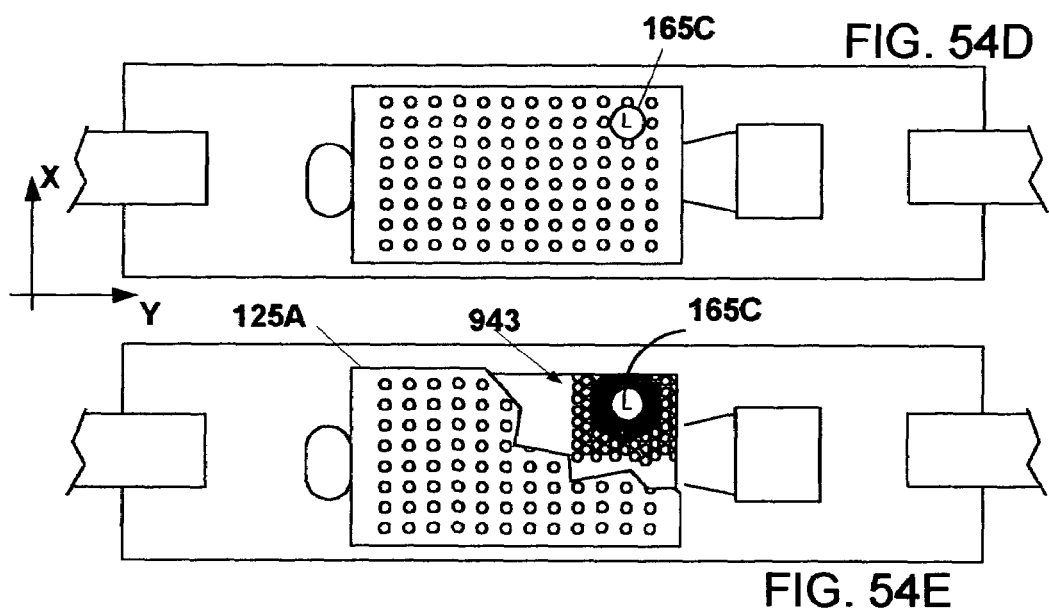
FIG. 54D
FIG. 54E

COMPUTER CONTROLLABLE LED LIGHT SOURCE FOR DEVICE FOR INSPECTING MICROSCOPIC OBJECTS

The present invention relates to automated inspection devices, and in particular to automated inspection devices having computer controllable light sources. This application is a continuation in part application of U.S. patent application Ser. No. 09/982,048 filed Oct. 18, 2001, now U.S. Pat. No. 6,985,616, issued on Jan. 10, 2000, which is incorporated by reference herein.

BACKGROUND OF THE INVENTION

The determination of the three dimensional atomic structure of matter is one of the most important areas of pure and applied research. One way in which the three dimensional atomic structure of matter can be determined is through X-ray crystallography. X-ray crystallography utilizes the diffraction of X-rays from crystals in order to determine the precise arrangement of atoms within the crystal. The result may reveal the atomic structure of substances such as metal alloys, deoxyribonucleic acid (DNA), or the structure of proteins.

There are very important benefits to knowing the accurate molecular structure of a protein crystal. For example, once the molecular structure is known, a drug designer can more effectively develop effective therapeutic agents and drugs. However, despite its promises, X-ray crystallography is limited by the fact that it is very difficult to grow successful crystals.

Prior Art Method of Growing Crystals

Protein crystals are commonly grown in the wells of micro-well plates. A micro-well plate is also known as a micro-titer plate or a microplate. Micro-well plates typically come with either 24, 48, 96, 384 or 1536 wells. A 96-well micro-well plate is shown in detail in FIG. 2. There are a variety of methods in which protein crystals may be grown. Five common ways are summarized below.

Hanging Drop Method

One of the main techniques available for growing crystals, known as the hanging-drop or vapor diffusion method, is a method wherein a drop of a solution containing protein is applied to a glass cover slip and placed upside down in an apparatus such as a vapor diffusion chamber where conditions lead to supersaturation in the protein drop and the initiation of precipitation of the protein crystal.

Sitting Drop Method

Another method is the sitting drop method where the drop sits in a small well adjacent the growing solution instead of hanging over it. This method provides a more stable drop and location.

Aqueous Drop in Oil Method

Another method is the aqueous drop in oil method. The drop is placed in a micro-well and is covered with an oil based solution. The drop stays at the bottom of the well as the crystal grows.

Dialysis Method

In another method referred to as the dialysis method (also called microbatch crystallization), the protein solution is contained within a semi-permeable size exclusion membrane and then placed in a solution of fixed pH and precipitant concentration. As the precipitant diffuses through the membrane into the protein compartment, the solubility of the protein is reduced and crystals may form.

Gel Crystal Growth Method

This method involves the placement of a gel into the end of small diameter glass capillaries. After the solutions have gelled, a protein solution is placed into one end (top) of the capillary and the other end is submerged in a solution of precipitating agent. If the conditions are appropriately selected, crystal growth occurs at a point in the gel where the protein and precipitating agent reach the proper concentrations as the solutions slowly mix by diffusion. Since this is a diffusion limited process, it thus only occurs after an extended period of time. Crystals however, grown by this method are often larger and of higher quality.

Regardless of the method chosen, protein crystal growth is a very delicate and time-consuming process. It can take several days to several months before crystals of sufficient size and quality are grown and ready for x-ray crystallography. The current minimum size that is typically stated is a crystal of at least 50 microns thick by 100 microns in extent. The protein crystal growing environmental conditions need to be rigorously maintained, from the chemistry, to the surrounding air humidity and temperature, cleanliness to prevent contamination, and even lighting conditions. A protein crystallographer working with unknown protein families may only be about 5% successful in growing proper sized quality crystals. With this success rate, for example, a 96-well micro-well plate may only have 5 wells in which good crystals are growing.

Prior Art Inspection of Crystal Growth

Currently, a laboratory technician, or operator, aided by a microscope and a laboratory notebook manually inspects crystals grown in micro-well plates. To inspect a micro-well plate, a laboratory technician dons a clean-room gown suit and enters a cold room in which the crystals are growing. The technician then puts a micro-well plate underneath the microscope and examines each well in the micro-well plate until all of the wells in the micro-well plate have been inspected. The technician then makes a mental judgement as to how he shall classify (also known as "score") the crystal. For example, the technician may feel that he is observing an image that shows "grainy precipitation" or "ugly precipitation". Or, he may feel that the image shows "no crystal growth". The technician then records the classification into a laboratory notebook.

The above system is riddled with opportunities for human error. An operator, manually inspecting a 96-well micro-well plate will take approximately 5 to 20 minutes depending on the skill of the operator and the number of wells that contain interesting features, microcrystals, or crystals. The operator may be subject to physical fatigue, suffer eyestrain, and may be uncomfortably cold in the temperature controlled and generally high humidity room. The operator can be tired and confused and can easily make errors in manually recording data in the notebook. For example, the operator may observe crystal growth at well H5 (FIG. 2), but incorrectly record in the notebook that the crystal growth was at well H6. Additional transcription errors may occur when the data is transferred to a computer database.

Research efforts are underway to by to solve the above problem, but they are inadequate for the needs of the industry. One such effort is described in Jurisica et al. "Intelligent Decision Support for Protein Crystal Growth" *IBM systems Journal*, Vol. 40, No 2, 2001.

What is needed is a better device for inspecting microscopic objects.

SUMMARY OF THE INVENTION

The present invention provides a device for inspecting microscopic objects. A plurality of LEDS is arranged in an array underneath a lens. Some of the LEDS are lighted and some of the LEDS are unlighted. A computer is in control of the LED array. The computer turns on selected LEDS from the array to form the lighted LEDS. Also, the computer turns off selected LEDS from the array to form the unlighted LEDS. The lighted LEDS form a pattern of lighted LEDS underneath the lens. In a preferred embodiment, the lens is connected to a computer controlled camera and the microscopic objects are microscopic crystals.

BRIEF DESCRIPTION OF THE DRAWINGS

FIGS. 45-50B illustrate the operation of the preferred embodiment shown in FIG. 44.

FIGS. 54A-54E show another preferred embodiment of the present invention.

DETAILED DESCRIPTION OF A PREFERRED EMBODIMENT

A detailed description of a preferred embodiment of the present invention can be described by reference to the drawings.

Figure 1:
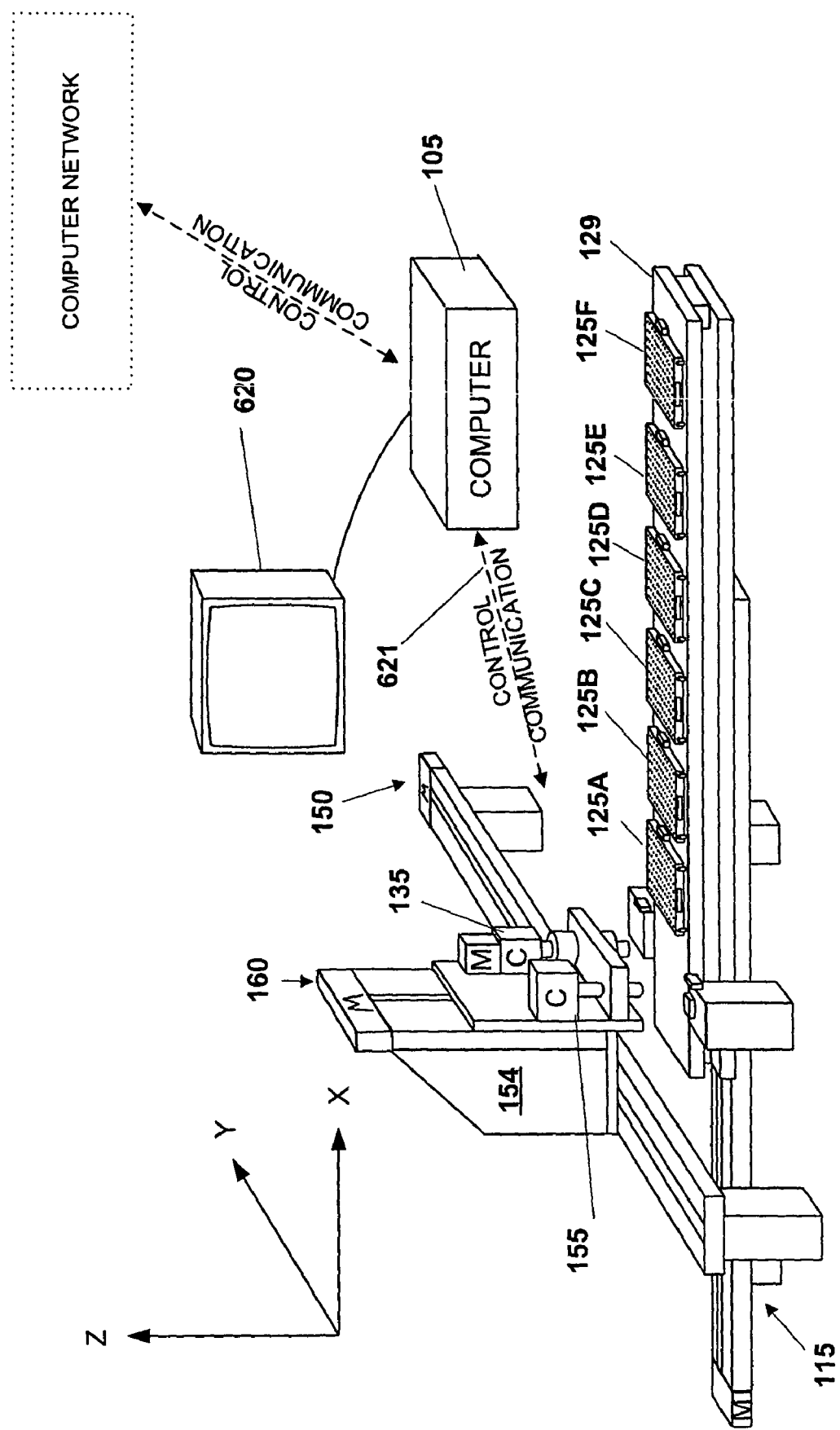
FIG. 1 shows a preferred embodiment of the present invention.

FIG. 1 shows a preferred embodiment of the present invention. Micro-well plates 125A-125F are placed on fixture plate 129. In a preferred embodiment, each micro-well plate has 96 wells. Each well has a drop of liquid in which microscopic protein crystals may be growing. Computer 105 automatically controls linear actuators 115, 150 and 160. Linear actuator 115 moves fixture plate 129 along the x-axis. Linear actuator 150 moves moving base 154 along the y-axis, and linear actuator 160 moves moving plate 162 along the z-axis. n The computer coordinates the movement of the linear actuators to properly position cameras 155 and 135 above each well of each micro-well plate 125A-125F in sequence. Preferably, cameras 155 and 135 are high-resolution ⅔ inch CCD cameras, with 1,300 horizontal pixel elements by 1,030 vertical elements. Each element is preferably 6.7 microns square with a sensing area of 8.7 mm by 6.9 mm. Cameras 155 and 135 take images of each well and transmit the images to computer 105 where they are digitized into a image data array of approximately 1,296 horizontal pixels by 1,000 vertical pixels by 8 bits of gray level representing the intensity (0 to 255) of each pixel. These digitized images are automatically recorded in the database of computer 105 and can be analyzed and scored by an operator via monitor 620. The digitized images may be further processed, analyzed, and the contents of the individual well scored by computer 105 executing program instructions to perform calculations on the image data array. In a preferred embodiment, computer 105 is connected via a communication/control line to a computer network. In this manner, the present invention can be controlled from a remote computer. Likewise, images and data can be transmitted to the remote computer.

Sequence of Operation of a Preferred Embodiment

Micro-well Plates Loaded onto the System

Figure 2:
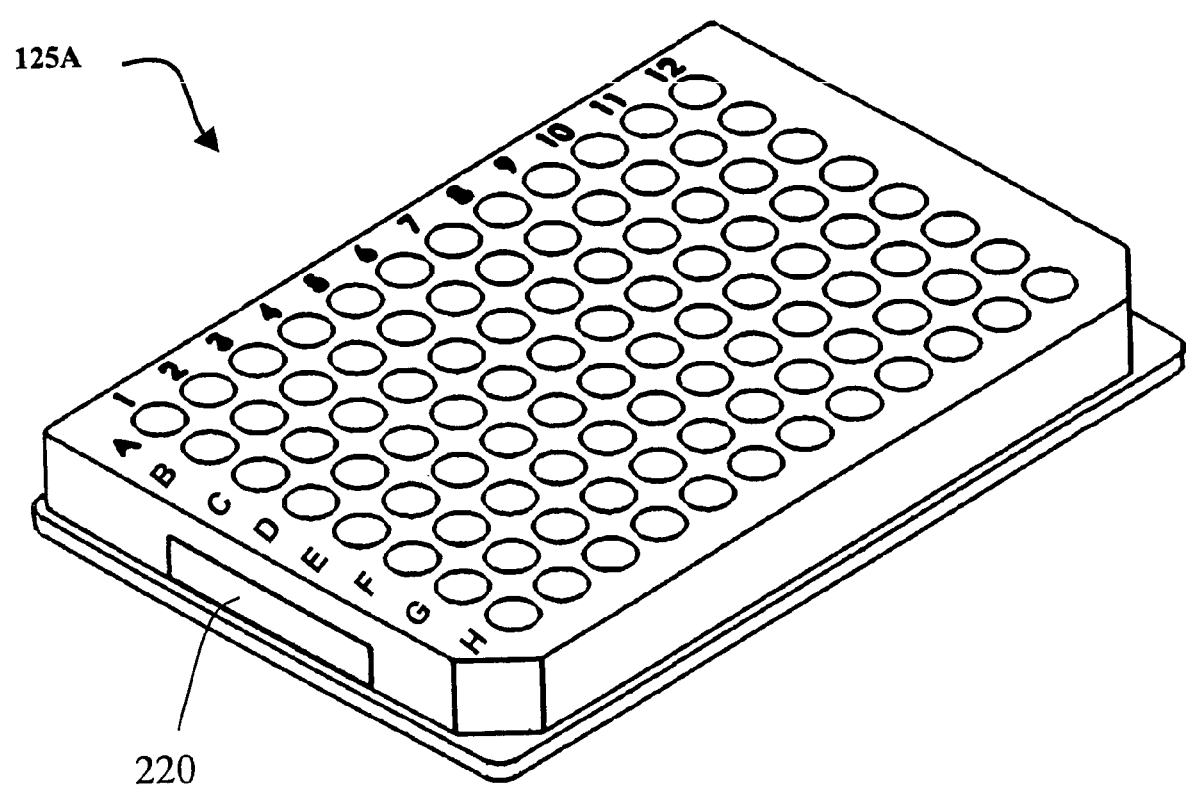
FIG. 2 shows a micro-well plate.

As shown in FIG. 1, six 96-well micro-well plates 125A-125F have been placed (either by an operator or by an external loading robot) onto fixture plate 129. A 96 well micro-well plate 125A is shown in FIG. 2. Micro-well plate 125A has wells labeled A1 through H12 and a bar code label 220. Micro-well plate 125A is available from Nalge-Nunc International, with U.S. offices in Rochester, N.Y. Fixture plate 129 will hold 24, 48, 96, 384, or 1536 well micro-well plates since the micro-well plate external width and length are fairly standard in the industry. The 96 well micro-well plate will be used to illustrate the present invention.

Figure 3:
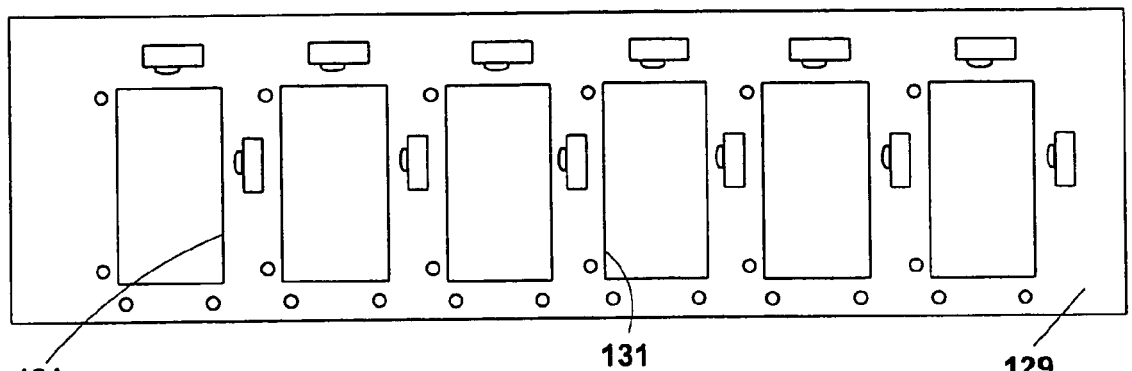
FIG. 3 shows a top view of the fixture plate.

FIG. 3 shows a top view of fixture plate 129 just prior to loading micro-well plates 125A-125F. Fixture plate 129 has six cutout sections 131 that are just slightly smaller in length and width than micro-well plates 125A-125F.

Figure 4:
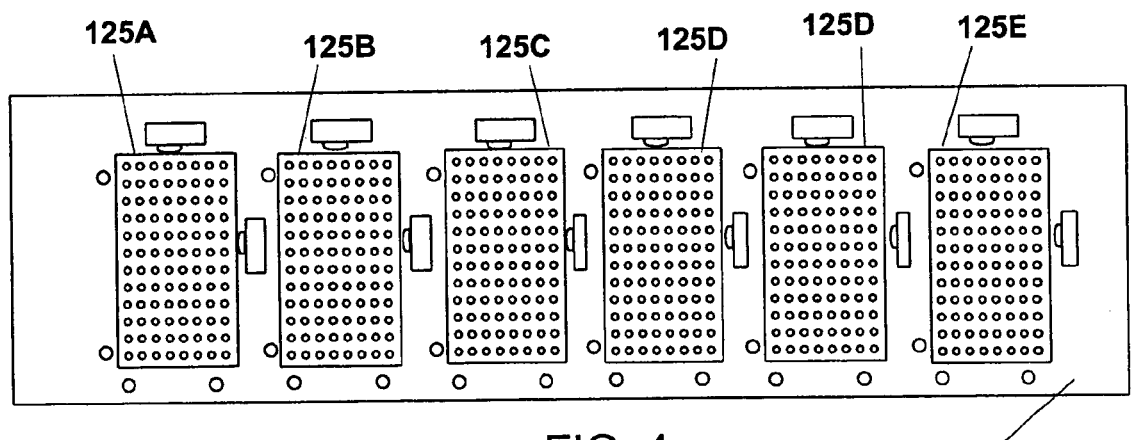
FIGS. 4 and 5 show top views of micro-well plates on the fixture plate.

FIG. 4 shows a top view of micro-well plates 125A-125F immediately after they have been placed on fixture plate 129.

Figure 5:
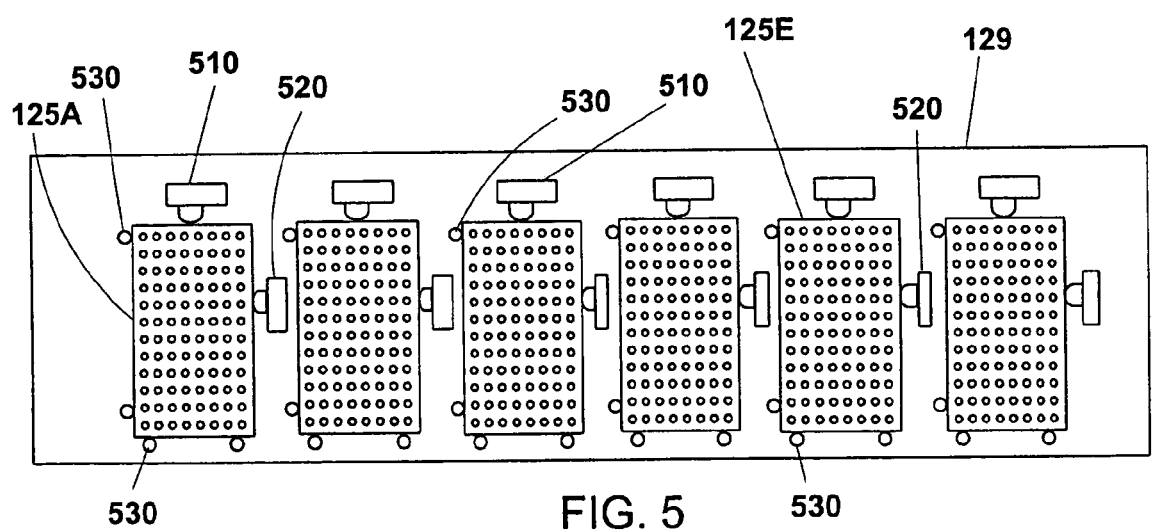

After the operator has placed micro-well plates 125A-125F onto fixture plate 129 as shown in FIG. 4, he enters the command into computer 105 (FIG. 1 and FIG. 6) to expand detents 510 and 520 (FIG. 5). The expansion of detents 510 and 520 firmly secures micro-well plates 125A-125F against plate stops 530.

Recording the Bar Code Information for the Micro-well Plates

Figure 7:
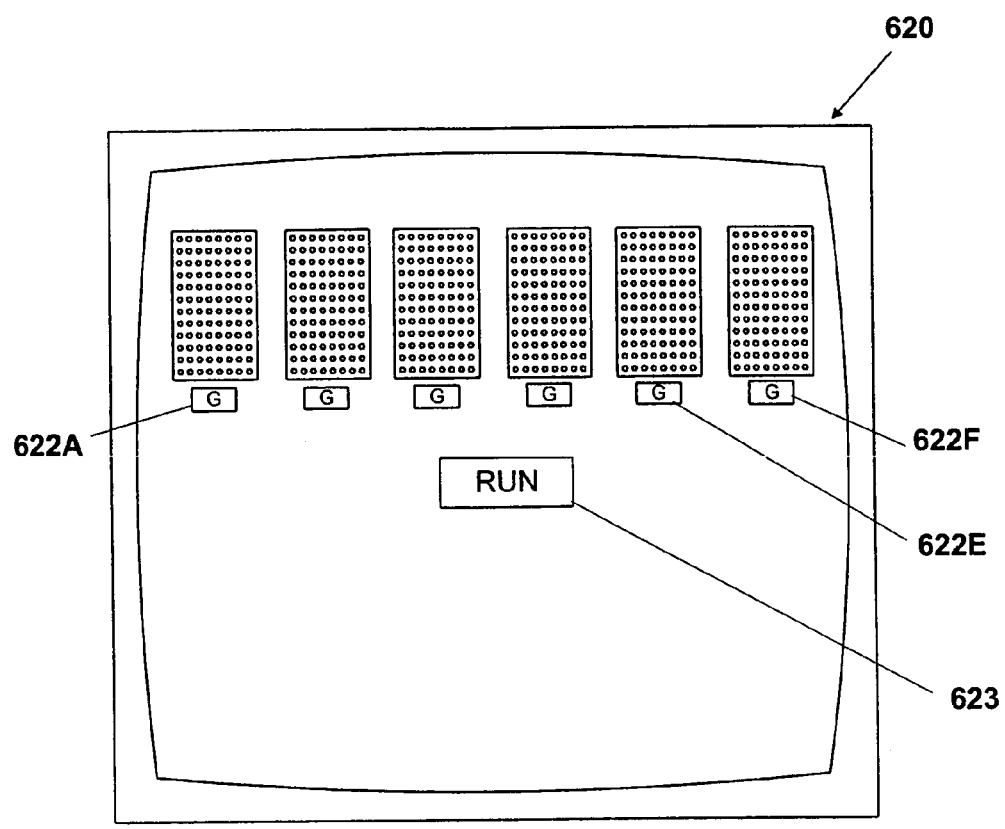
FIG. 7 shows a preferred monitor.

Computer 105 (FIG. 1) has been programmed to accept inputs from an operator. FIG. 7 shows a display representing micro-well plates 125A-125F on the screen of monitor 620. In FIG. 7, the operator has mouse clicked on bars 622A-622F, which has caused them to turn green. By clicking on bars 622A-622F, the operator has selected corresponding micro-well plates 125A-125F to "run". The operator sends the command to run the selected micro-well plates by clicking on run bar 623.

Figure 8:
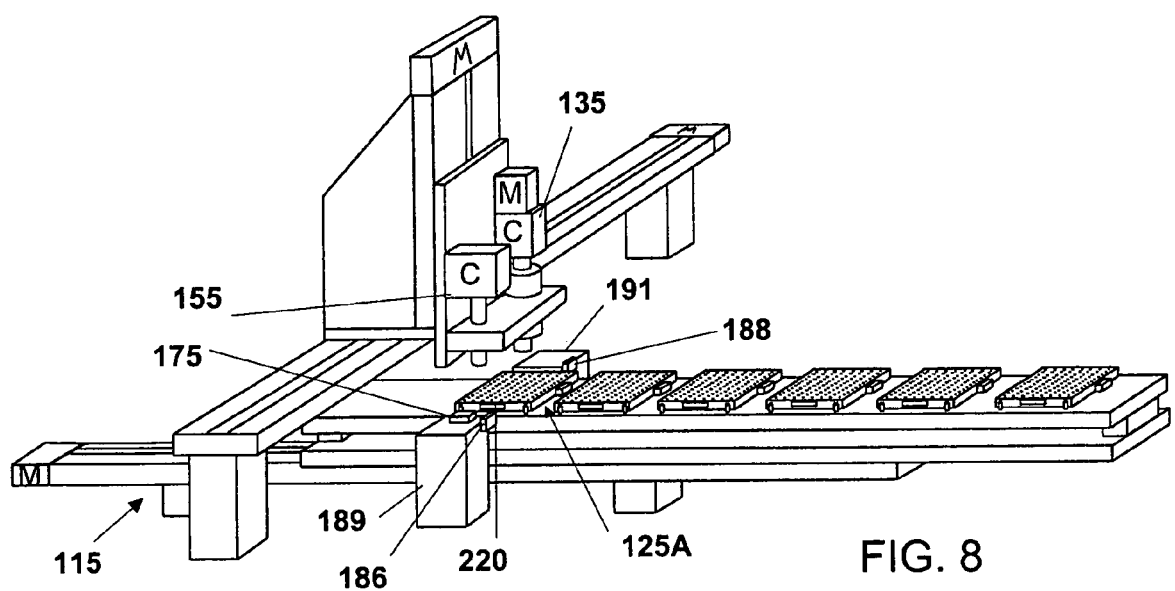
FIGS. 8-10 and 18-25 show steps in the sequence of operations of a preferred embodiment of the present invention.

In FIG. 8, the operator has given the command to run the selected micro-well plates. Micro-well plate 125A has been moved to a position underneath cameras 155 and 135. By the utilization of plate sensor transmitter/receiver 186 and reflector 188, information is sent to computer 105 reporting that micro-well plate 125A is in position underneath the cameras. Plate sensor transmitter/receiver 186 is fixed to support 189 and is aligned to sense whenever a micro-well plate breaks a beam of light emitted by transmitter/receiver 186 and reflected by a reflector 188. Reflector 188 is mounted on support 191 on the opposite side of the linear actuator 115. The plate sensor transmitter/receiver 186 and reflector 188 are preferably model #E3T-SR13 available from Western Switch Controls of Santa Ana, Calif.

Bar code reader 175 is also mounted to support 189 and is positioned to view bar-code identity label 220 (FIG. 2) attached to micro-well plate 125A when it is positioned underneath cameras 155 and 135. Bar-code reader 175 is preferably model #BL601 available from Keyence Corporation of America of Newark, N.J. Bar-code reader 175 communicates with computer 105 via a communication line. Information encoded into label 220 preferably includes: the plate serial number, the plate type (i.e., 24-well, 48-well, 96-well, 384-well, or 1536-well micro-well plate), and the well type (i.e., square, or rounded, hanging drop, sitting drop, constrained sitting drop).

The information from plate sensor transmitter/receiver 186 and bar-code reader 175 is transmitted to computer 105 and stored for later use during the camera inspection and information acquisition phase.

Figure 9:
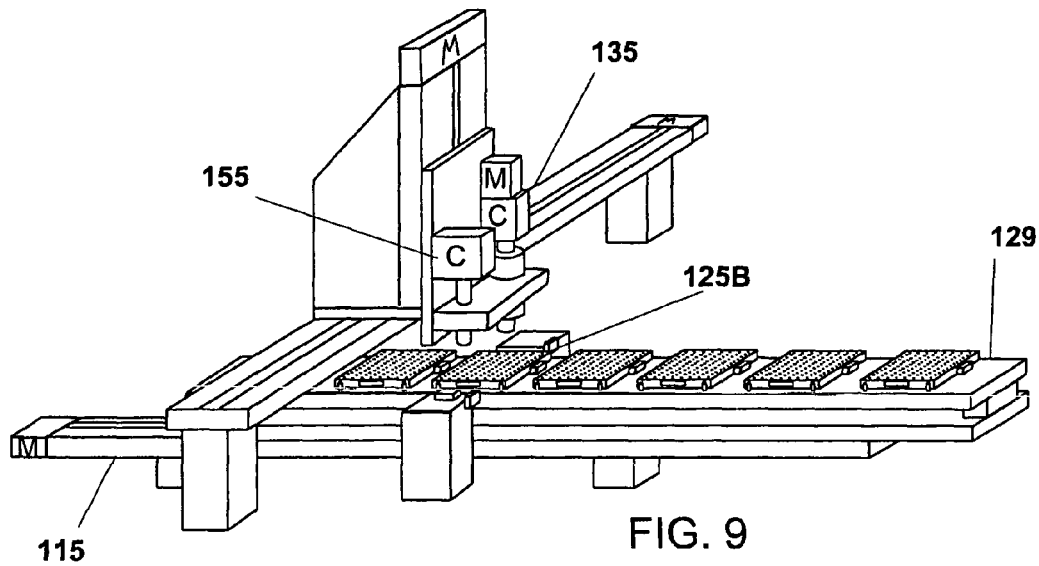

In FIG. 9, linear actuator 115 has moved fixture plate 129 so that micro-well plate 125B is underneath cameras 155 and 135. In a fashion similar to that described above with regards to micro-well plate 125A, information is transmitted from plate sensor transmitter/receiver 186 and bar-code reader 175 to computer 105 and stored for later use during the camera inspection and information acquisition phase.

The above described sequence continues until all micro-well plates 125A-125F have been sensed and recorded by plate sensor transmitter/receiver 186 and bar-code reader 175.

Figure 10:
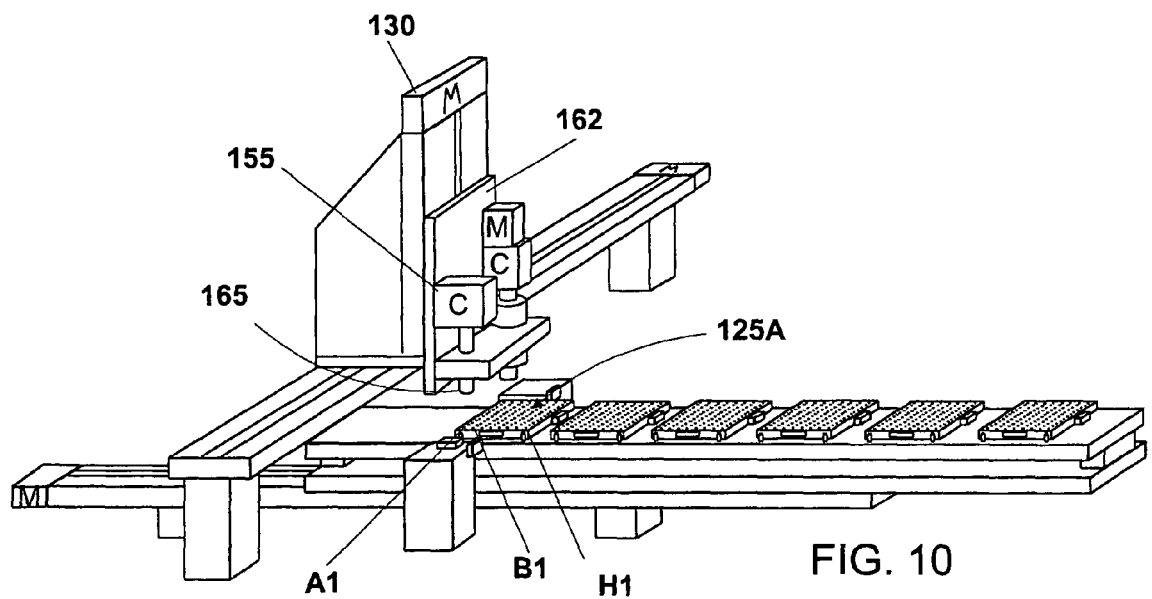

Then, as shown in FIG. 10, linear actuator 115 moves micro-well plate 125A so that it is underneath lens 165 of camera 155. Motor 130 of linear actuator 160 moves moving plate 162 upward and/or downward as necessary to properly focus lens 165 on the drop of hanging liquid over well A1. Preferably, lens 165 is set at a predetermined zoom.

Inspection of Crystals

Determining the Position of the Drop of Liquid within Each Well

An operation to inspect each well to determine the position of each hanging drop of liquid is performed on micro-well plate 125A after it has been moved to the position shown in FIG. 10.

Figure 11:
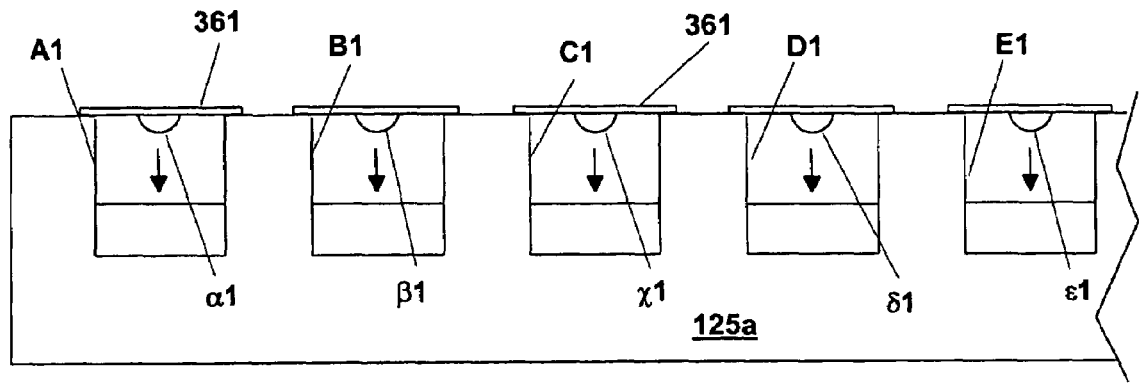
FIG. 11 shows hanging drops of liquid in a micro-well plate.

FIG. 11 shows a cross section side view of wells A1-E1 of micro-well plate 125A. In a preferred embodiment, an attempt has been made to grow protein crystals in the hanging drops in each of the wells of micro-well plate 125A. FIG. 11 shows hanging drops $\alpha 1$, $\beta 1$, $\chi 1$, $\delta 1$, and $\epsilon 1$.

The preferred method for protein crystal growth is the hanging drop method. The hanging drop method (also known as vapor diffusion) is probably the most common method of protein crystal growth. As explained in the background section, a drop of protein solution is suspended over a reservoir containing buffer and precipitant. Water diffuses from the drop to the solution leaving the drop with optimal crystal growth conditions.

Figure 13:
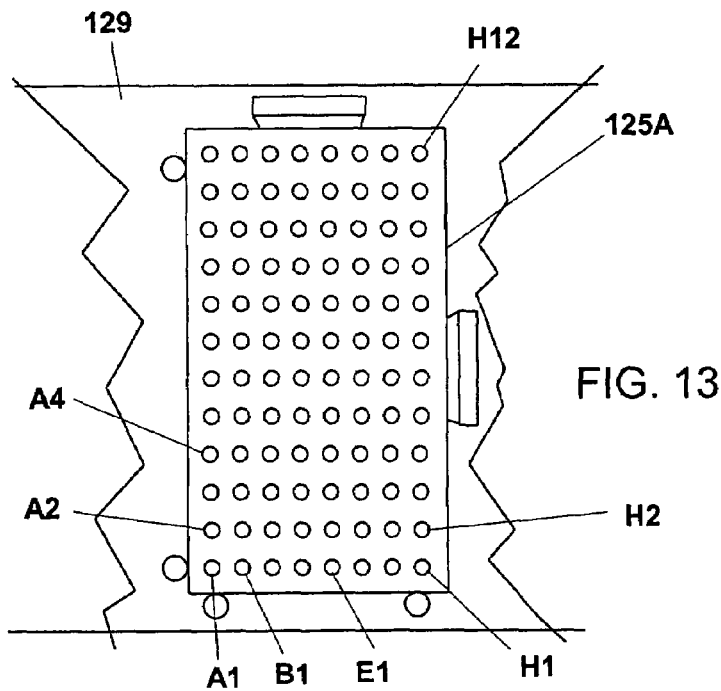
FIG. 13 shows a top view of a micro-well plate on the fixture plate.

In FIG. 10, lens 165 of camera 155 is over well A1 of micro-well plate 125A (FIG. 2, FIG. 11, and FIG. 13). FIG. 13 shows a top view of micro-well plate 125A positioned on fixture plate 129.

Figure 14:
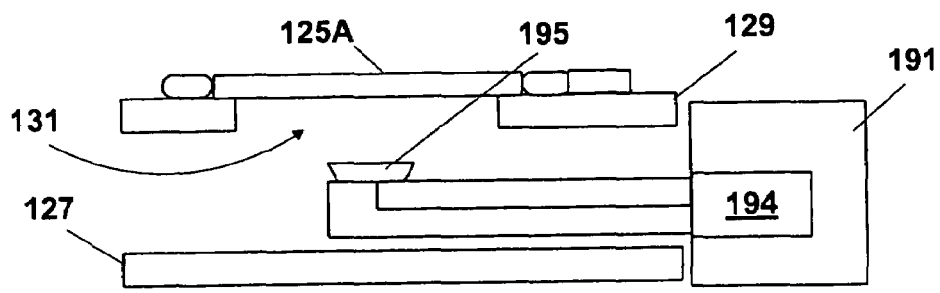
FIG. 14 shows a side view of the light source shining upwards onto a micro-well plate.

FIG. 14 shows a side view of micro-well plate 125A positioned on fixture plate 129. Support 191 with embedded light source 194 is positioned to the side of fixture plate 129. Light from light guide 195 is directed upward through cutout 131 (also shown in FIG. 3). Light guide 195 is positioned between fixture plate 129 and plate 127 such that both plates can move around the light guide 195 without interference. As explained above, fixture plate 129 has cutouts 131 (FIG. 3) that are smaller than the micro-well plates 125 and located under each well plate, such that light from light guide 195 can be projected through the well plates when they are brought into position for inspection. In the preferred embodiment, light source 194 is model #A08925 fiber-optic backlight available from Aegis Electronics of Carlsbad, Calif.

Camera 155 (FIG. 10) inspects well A1 and transmits an image to computer 105 for digitization. As described above, camera 155 preferably (FIG. 10) inspects well A1 at a 1× magnification so that every 6.7 micron square pixel represents approximately 6.7 square microns on the object being measured, allowing for some small geometric distortions caused by the lens 165. Computer 105 has been programmed to digitize the camera image and then by utilizing vision software determines a position within well A1 for the drop of liquid hanging from grease seal 361. The position of the drop of liquid is recorded for later use onto the hard drive of computer 105 and to a memory location within the computer.

In a preferred embodiment, the vision software used to determine the position of the drop of liquid uses a software routine algorithm called mvt_blob_find from a collection of image processing tools called MVTools. MVTools is available from Coreco Imaging, US Office in Bedford, Mass.

Figure 15:
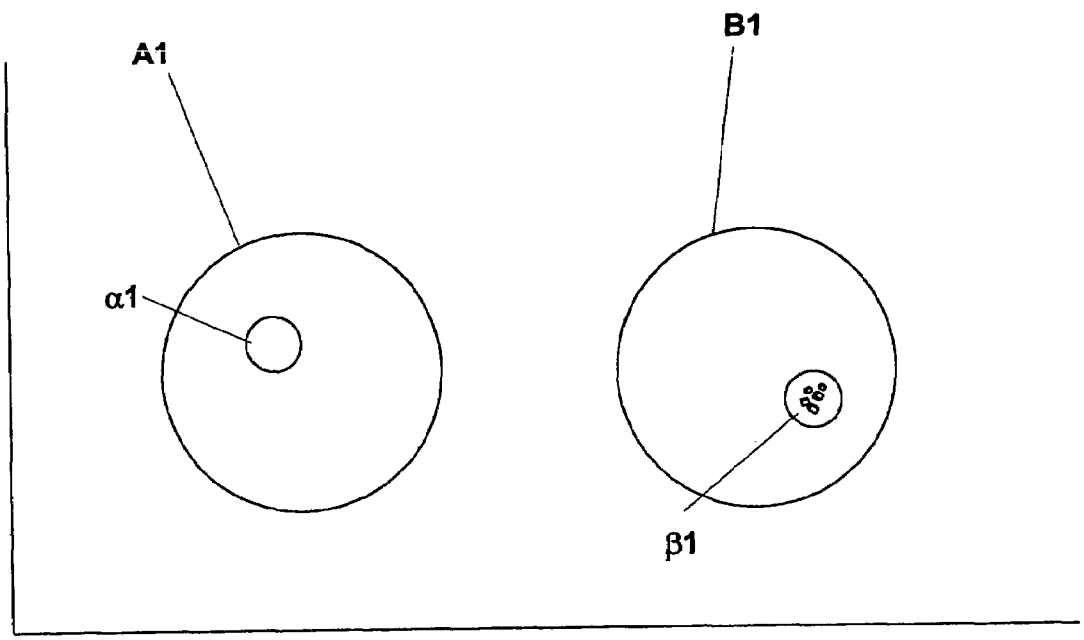
FIG. 15 shows a magnified view of two wells of a micro-well plate, wherein each well

After recording the position of the drop of liquid hanging from grease seal 361 in well A1, linear actuator 115 moves fixture plate slightly to the left so that lens 165 is over well B1 (FIG. 13). In a fashion similar to that described for well A1, the position of the drop of liquid hanging from grease seal 361 in well B1 is recorded on the hard drive of computer 105 and in computer memory. For example, as shown in FIG. 15, computer 105 will record that drop of liquid $\alpha$1 is towards the upper left-hand quadrant of well A1. Likewise, the position of drop of liquid $\beta$1 is recorded onto the database of computer 105 as being in the lower right-hand quadrant of well B1.

Figure 18:
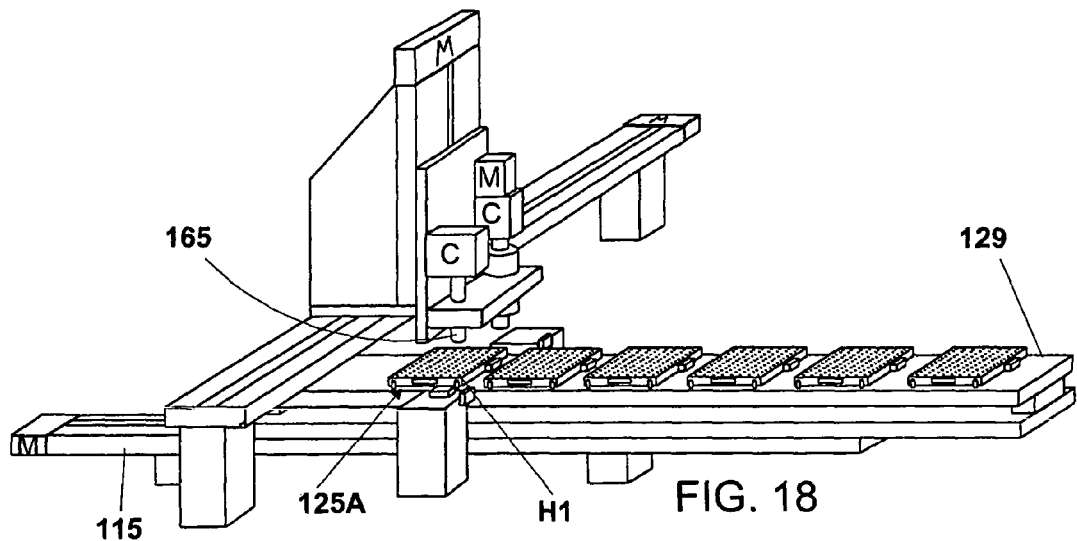

In this manner, positions of the drops of liquid are recorded for cells A1-H12. In FIG. 18, linear actuator 115 has moved fixture plate 129 so that well H1 is under lens 165.

Figure 19:
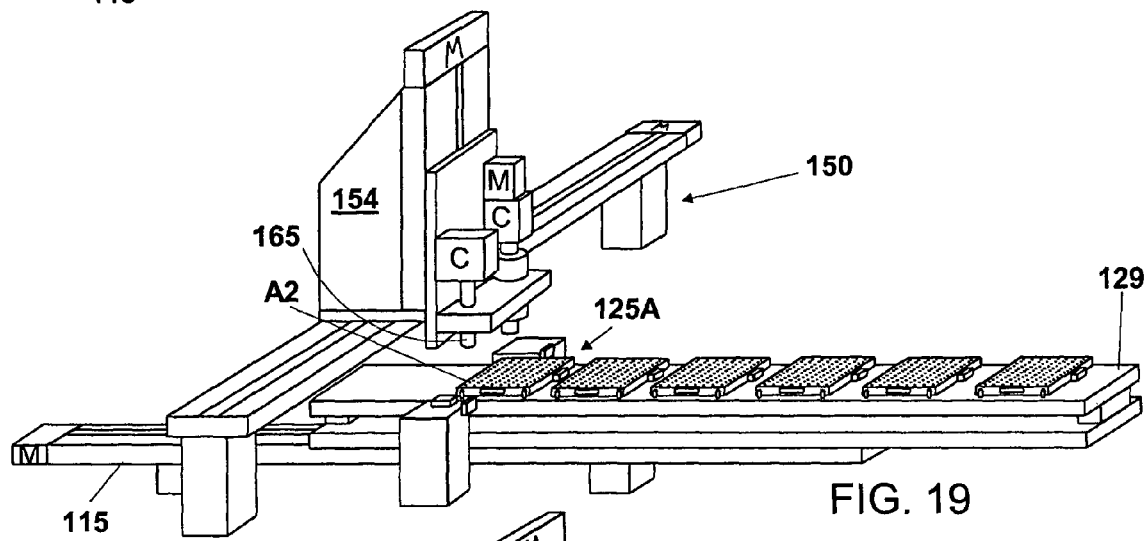

In FIG. 19, linear actuator 115 has moved fixture plate 129 to the left and linear actuator 150 has moved moving base 154 slightly rearward so that lens 165 is over well A2 of micro-well plate 125A (FIG. 13).

Figure 20:
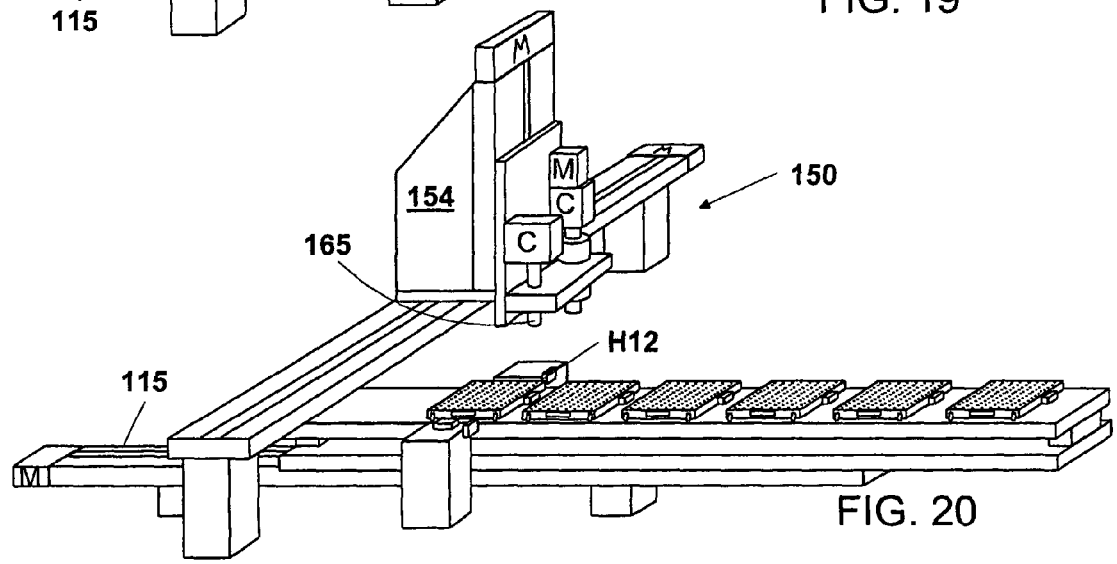

In a manner similar to that described above, positions of the drops of liquid are recorded for cells A2-H12 (FIG. 2, FIG. 13). In FIG. 20, linear actuator 115 has moved fixture plate 129 to the left and linear actuator 150 has moved moving base 154 rearward so that well H12 is under lens 165.

Figure 21:
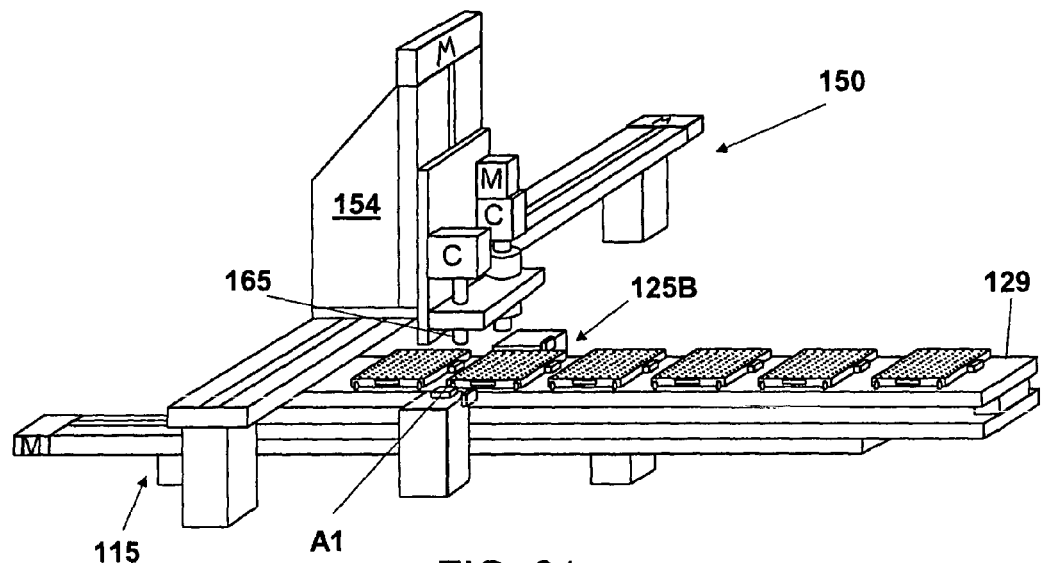

After positions of the drops of liquid are recorded for cells A1-H12 for micro-well plate 125A, linear actuator 115 moves fixture plate 129 and linear actuator 150 moves moving base 154 so that cell A1 of micro-well plate 125B is underneath lens 165 (FIG. 21).

Figure 22:
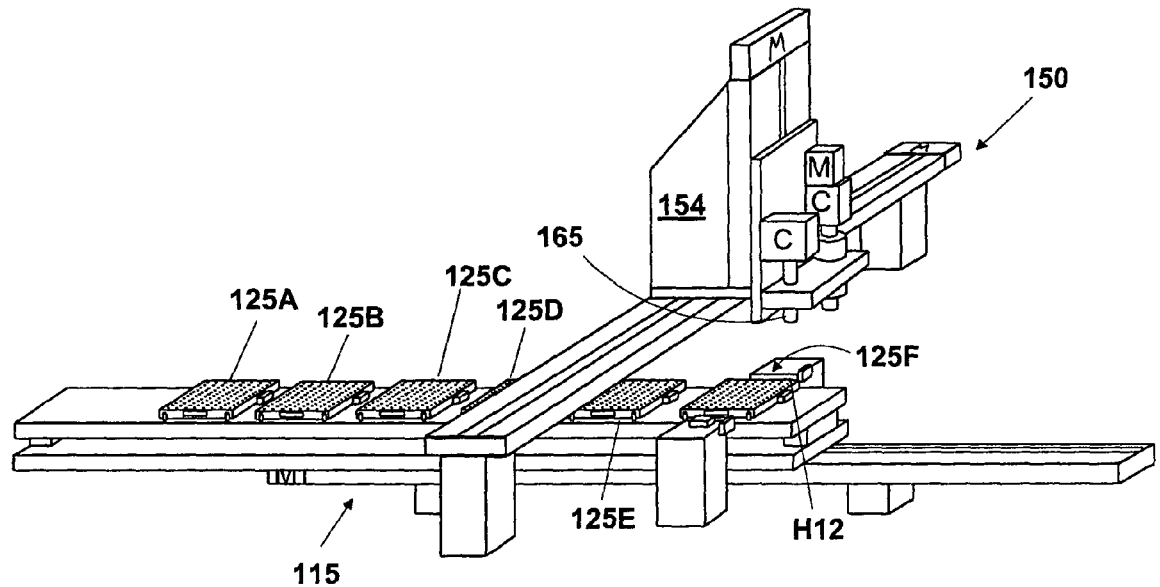

In a manner similar to that described above, positions of the drops of liquid are recorded for cells A1-H12 for each micro-well plate 125A-125F. In FIG. 22, linear actuator 115 has moved fixture plate 129 and linear actuator 150 has moved moving base 154 so that well H12 of micro-well plate 125F is under lens 165.

Recording the Image of the Drop of Liquid within Each Well

Figure 16:
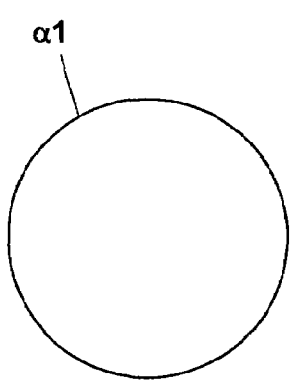
FIGS. 16 and 17 show a detail view of the drops of liquid shown in FIG. 15.
Figure 23:
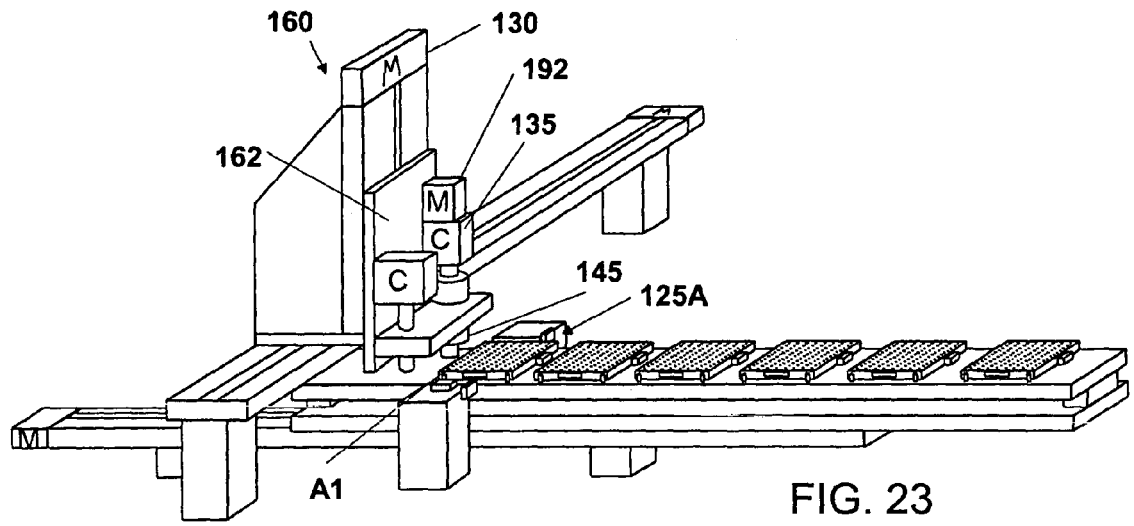

An operation to inspect each hanging drop is performed at a higher magnification using camera 135 with its zoom lens 145 capable of magnifications of 2.5× to 10× corresponding approximately to digitized pixels representing 2.68 microns square (at 2.5×) to 0.67 microns square (at 10×). This inspection is done for the purpose of determining whether protein crystals have grown. Zoom motor 192 controls the degree of zoom for zoom lens 145. Using data representing the position of the drop of liquid within each well obtained during the inspect-well sequence, computer 105 (FIG. 1) automatically transmits a signal to linear actuators 115 and 150 to position lens 145 directly over the drop of liquid within each well. For example, in FIG. 23 lens 145 is positioned over the top of well A1 of micro-well plate 125A. Using the positioning data earlier obtained, lens 145 is precisely positioned so that it is able to zoom in on drop of liquid $\alpha$1 (FIG. 13). FIG. 16 shows a magnified view of drop of liquid $\alpha$1. In FIG. 23, motor 130 of linear actuator 160 has moved moving plate 162 upward and/or downward as necessary to properly focus lens 165 on drop of liquid $\alpha$1. Zoom motor 192 has manipulated lens 165 to obtain the desired degree of zoom. Camera 135 inspects well A1 and transmits a signal representing the magnified image of the hanging drop of liquid to computer 105. The images are stored on computer 105 temporarily in memory for immediate analysis and on hard disk for later analysis.

Figure 17:
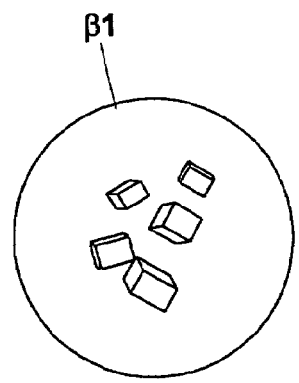

In a similar fashion, linear actuators 115, 150 and 160 and zoom motor 192 operator to properly position and magnify zoom lens 145 over each hanging drop of liquid to obtain desired focus and magnification for image data storage. For example, FIG. 17 shows a magnified view of hanging drop of liquid $\beta$1.

Figure 24:
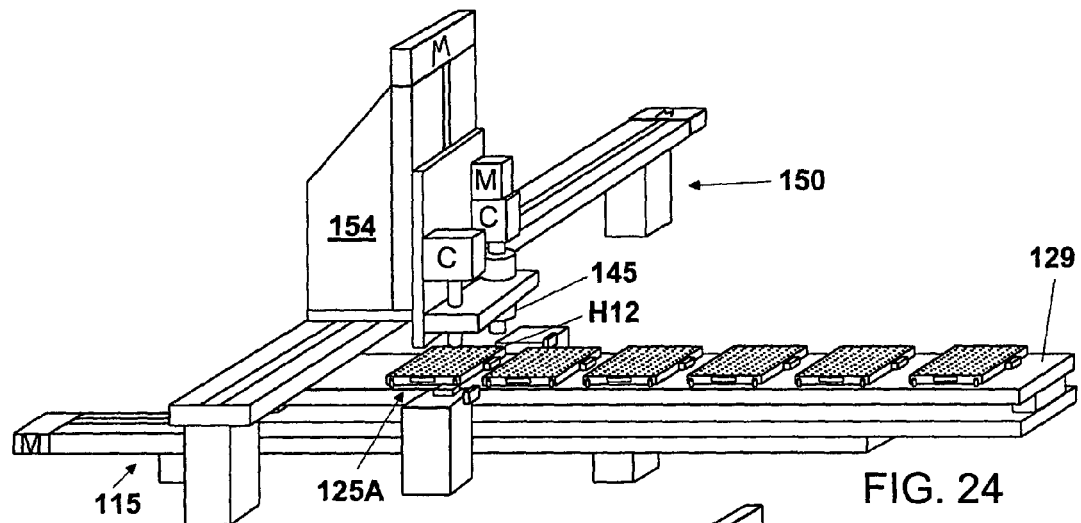

In a manner similar to that described above during the inspect-well sequence, magnified images of the drops of liquids (similar to those shown in FIGS. 16 and 17) are recorded for cells A1-H12 for micro-well plate 125A (FIG. 2, FIG. 13). In FIG. 24, linear actuator 115 has moved fixture plate 129 and linear actuator 150 has moved moving base 154 so that well H12 of micro-well plate 125A is under lens 165.

Figure 25:
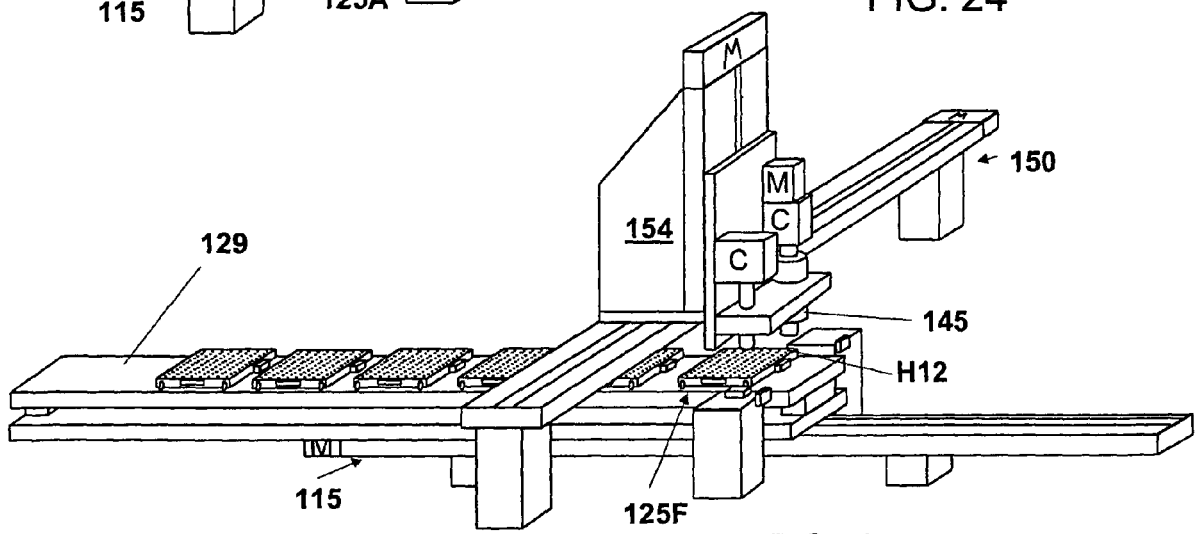

Then, the sequence is repeated for micro-well plates 125B-125F so that magnified images of the hanging drops of liquids are recorded for each cell A1-H12 for micro-well plates 125B-125F. In FIG. 25, the sequence has ended for micro-well plates 125A-125F. Linear actuator 115 has moved fixture plate 129 and linear actuator 150 has moved moving base 154 so that well H12 of micro-well plate 125F is under lens 145.

Manual Scoring the Drop of Liquid within Each Well

Figures 26, 27:
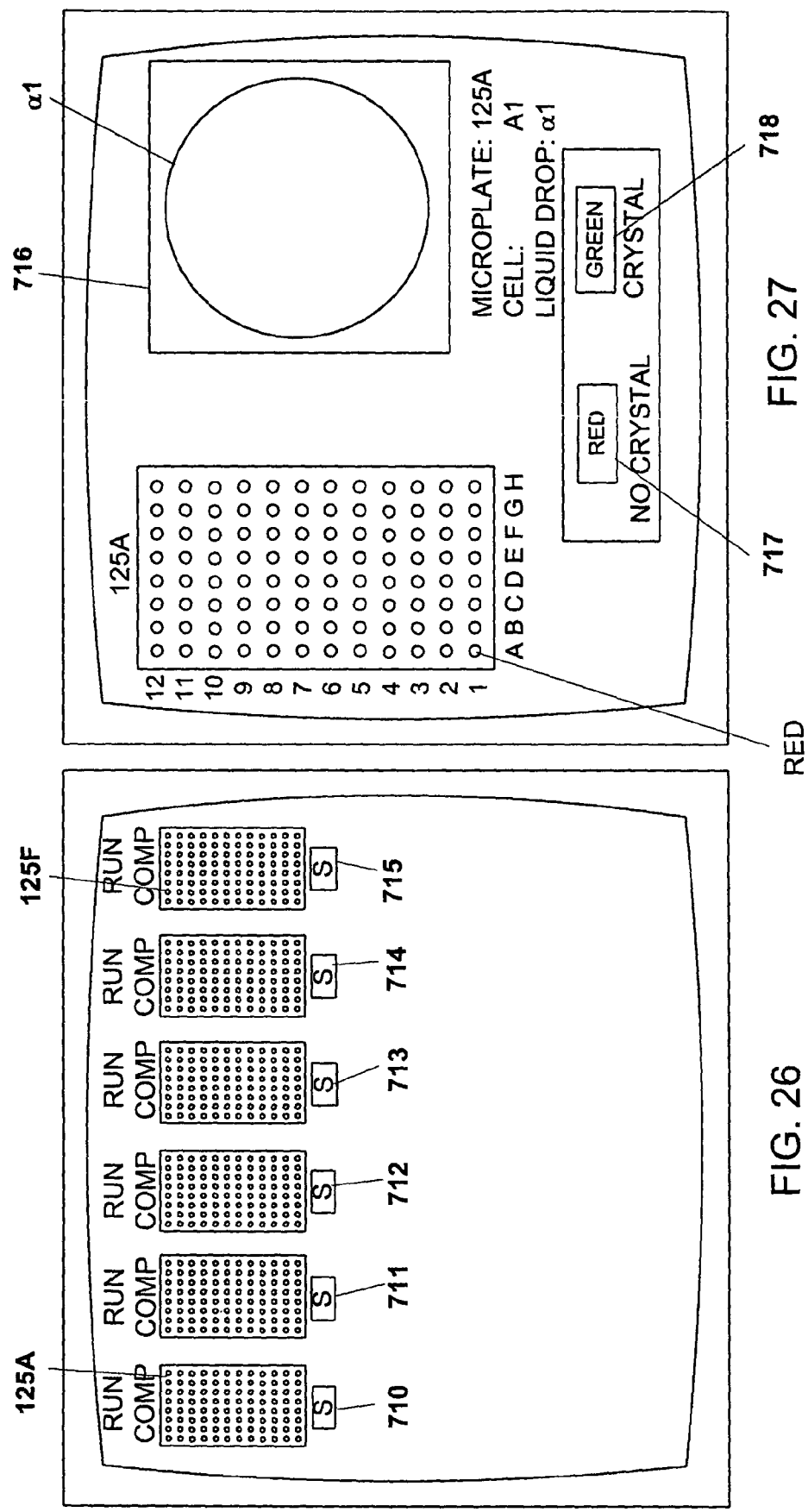
FIG. 26 shows a preferred monitor screen after a run has been completed.
FIGS. 27 and 28 show details of other preferred monitor screens.

After micro-well plates 125A-125F have been run, monitor 620 will appear as shown in FIG. 26. In FIG. 26, six images representing micro-well plates 125A-125F appear on the screen. Above each image is a message "Run Comp" indicating that image data for hanging drops of liquid has been transferred into computer 105. Beneath each image are buttons 710-715 marked "S". By mouse clicking on any button 710-715, the operator may manually score for successful crystal formation each magnified image of each hanging drop of liquid.

For example, in FIG. 26, the operator can mouse click on button 710 to score micro-well plate 125A.

In FIG. 27, the operator has mouse clicked on the circle representing well A1 of micro-well plate 125A. This has caused a magnified image to be displayed of drop of liquid $\alpha$1 in screen section 716. The operator has concluded that there are no crystals in drop of liquid $\alpha$1 and has therefore mouse clicked on button 717 for "NO CRYSTAL". On the display screen, this has caused the circle representing well A1 of micro-well plate 125A to turn red.

Figure 28:
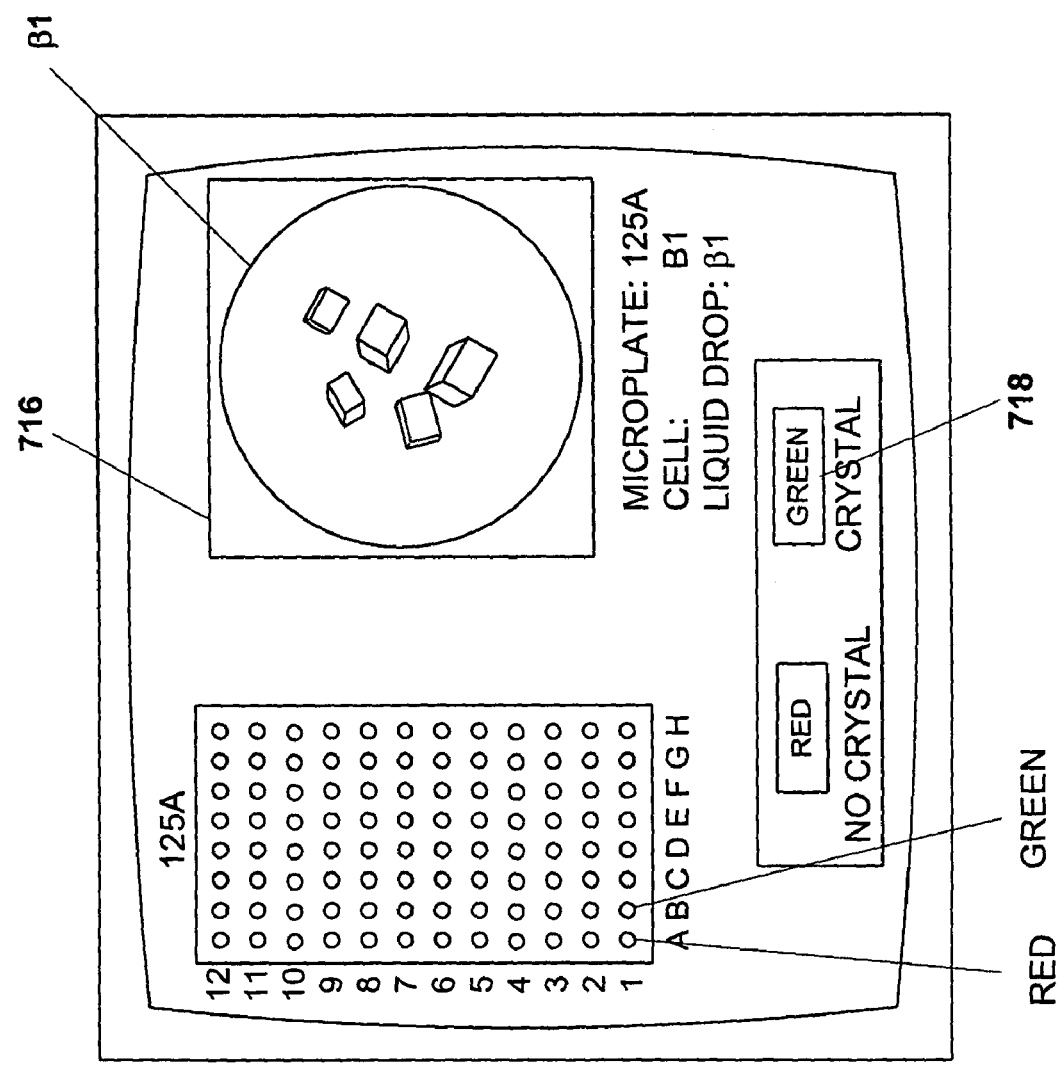

In FIG. 28, the operator has mouse clicked on the circle representing well B1 of micro-well plate 125A. This has caused a magnified image to be displayed of drop of liquid $\beta$1 in screen section 716. The operator has concluded that there are crystals in drop of liquid $\beta$1 and has therefore mouse clicked on button 718 for "CRYSTAL". On the display screen, this has caused the circle representing well B1 of micro-well plate 125A to turn green.

In a similar fashion, the above scoring procedure is repeated until all wells A1-H12 for micro-well plates 125A-125F have been scored as either red (NO CRYSTAL) or green (CRYSTAL).

Data Utilization

Once micro-well plates 125A-125F have all been scored, the operator has at his easy disposal a database that contains the identity of each micro-well plate that was inspected along with a score summarizing whether crystal formation occurred for each well in the micro-well plate. The automated and efficient manner in which the operator is able to acquire his contrasts with the prior art method of laboriously inspecting each well with a microscope and the handwriting the results into a notebook.

For example, to score six 96-well micro-well plates utilizing the present invention should take approximately no more than 10 to 15 minutes.

In contrast, the prior art method of inspecting six 96-well micro-well plates with a microscope and the handwriting the results into a notebook will take approximately 30 to 100 minutes depending on the conditions discussed in the background section in addition to the time required to transcribe the results into a computer database. Plus, as previously explained in the background section, manual inspection and scoring is subject to a relatively high risk of human error.

Second Preferred Embodiment

Figure 29:
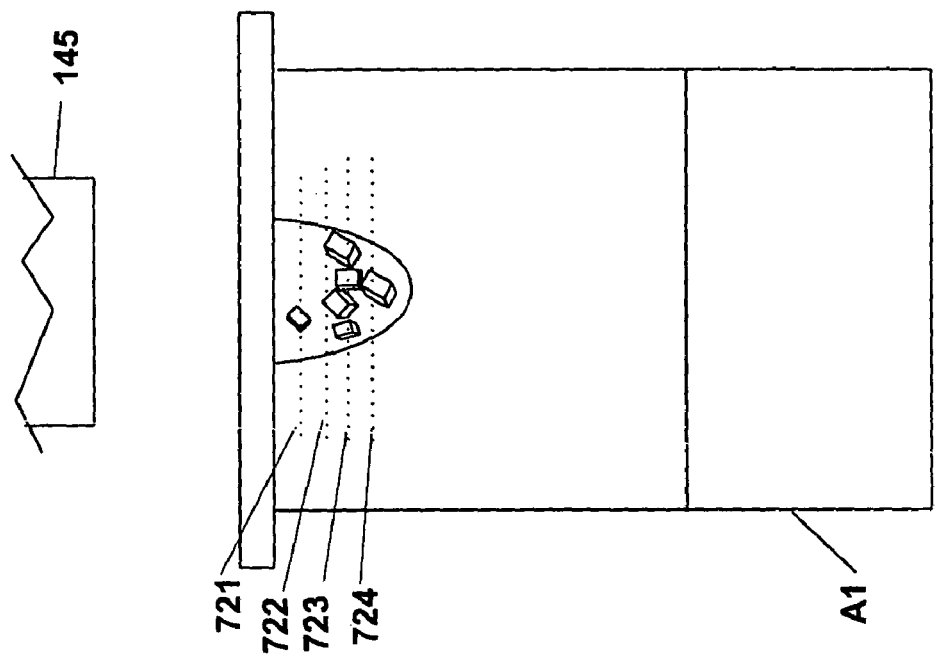
FIG. 29 shows a hanging drop of liquid with crystal growth.

In a second preferred embodiment, the depth of view of camera 135 is approximately 50 to 100 micrometers. The crystal in the drop of liquid may be larger than the depth of view or there may be crystals growing at various levels within the hanging drop of liquid, as shown in FIG. 29. Therefore, in the second preferred embodiment, lens 145 is focused at multiple different levels 721-724 and a set of images are recorded at the different levels so that the entire crystal may be analyzed.

Specimen Auto-focus

Figure 31:
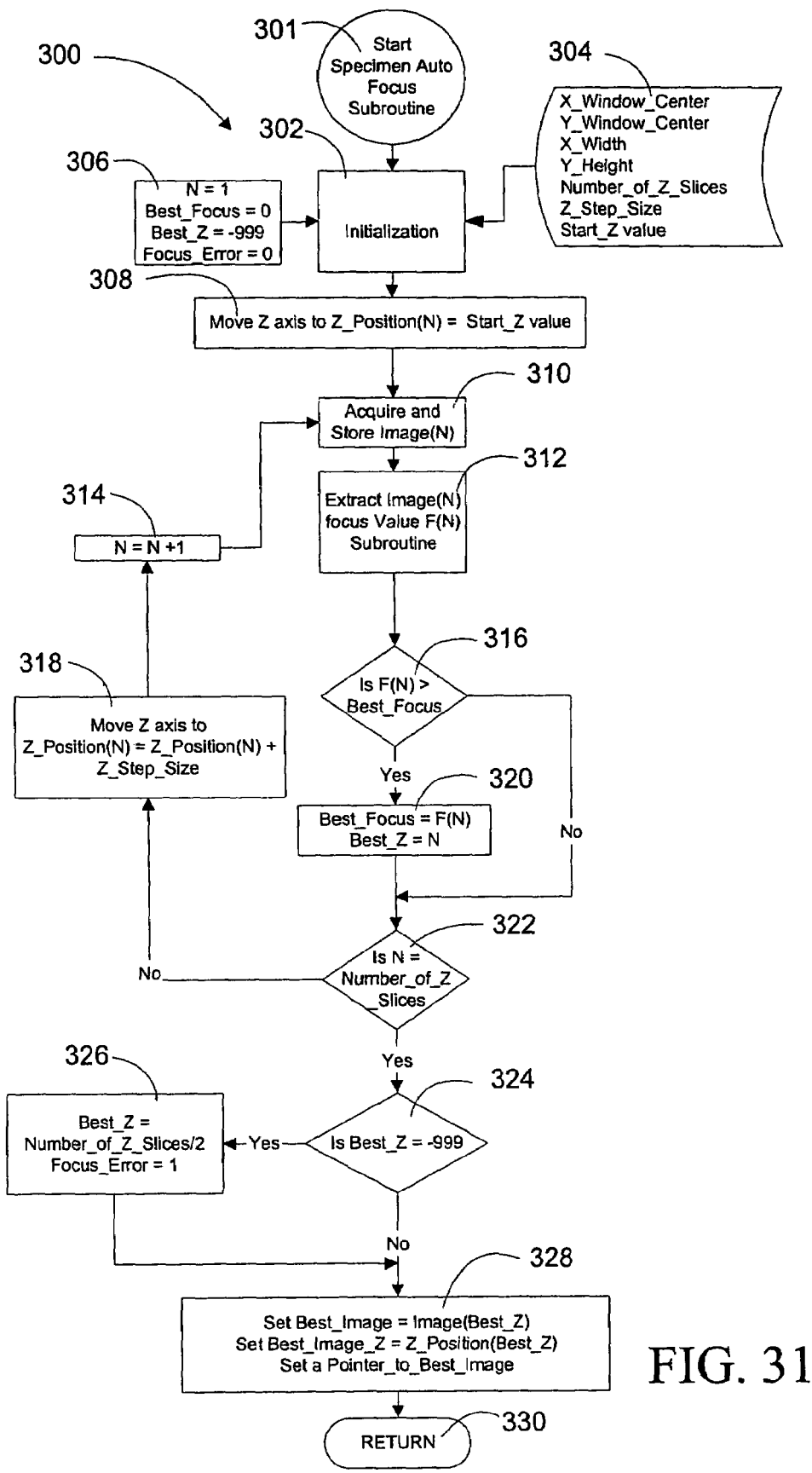
FIG. 31 shows a flowchart of an auto-focus subroutine of the present invention.

The third preferred embodiment of the present invention utilizes a specimen auto-focus subroutine 300 (FIG. 31). Subroutine 300 ensures that the specimen within the micro-well is in-focus at the desired zoom (or magnification ratio) of image lens 145. Utilizing the auto-focus feature, the present invention causes camera 135 to take a number of images defined by a Number_of_Z_Slices. Typically, there are between 5 and 10 slices separated in the Z-axis from one another by a Z_Step_Size. The typical step size is 0.05 mm to 0.25 mm. The slices preferably start at a Z-Axis location defined by a Start_Z value, which is typically at the bottom of the cover-slip on the micro-well plate. During specimen auto focus initialization 302, input data 304 is received. The area of interest window within the images is further defined in the input data 304 by a X_Window_Center and a Y_Window_Center plus an X_Width and a Y_Width. Initial settings 306 for the routine 300 are the starting value of a counter N, a Best_Focus, a Best_Z, and a Focus_Error. The inspection device sets Z_Position(N) equal to the Start_Z location and moves camera 135 there in step 308. An image is acquired with camera 135 and digitized as previously described and stored as Image (N) in step 310. A second subroutine 312 extracts a focus value F (N) for Image (N) and is further described in the section for discussion for FIG. 32. A test is made between F(N) and the Best_Focus in step 316, such that if F(N) is greater than Best_Focus then Best_Focus is set to F(N) and Best_Z is set to N as shown in step 320 and the program flow goes onto step 322, if the test condition is not met in step 316 then the program flow skips step 320 and goes on to step 322. In step 322, a test is made to determine of all of the slices have been taken as N is tested against the Number_of_Z_Slices. If N is equal to Number_of_Z_Slices then program flow goes onto step 324. If more slice images are needed, then the flow goes to step 318. In step 318, Z_Position (N+1) is set to Z_Position(N)+Z_Step_Size and the Z-Axis is moved to Z_Position(N+1) and the program flow goes on to step 314 where N is incremented by 1 (one). The program flow goes back to step 310 and completes the loop of step 310 to step 322 until all of the image slices have been taken and then moves onto step 324. In step 324, Best_Z is tested against its initial value, and if it equals its initial value (meaning no focus was found in the focus value subroutine 312) then it is set to a default value of the Number_of_Z_Slices divided by 2 and Focus_Error is set to 1 (one) in step 326 and the program flow goes onto step 328. If Best_Z in step 324 has a value other than its initial value then program flow goes onto step 328 from step 324. In step 328 a Best_Image image is set to the image slice at best focus by setting Best_Image equal to Image(Best_Z). Also, a Best_Image_Z value is set equal to Z_Position(Best_Z) and the flow goes onto step 330 which is the RETURN part of the subroutine and program flow returns to the main software flow.

Figure 32:
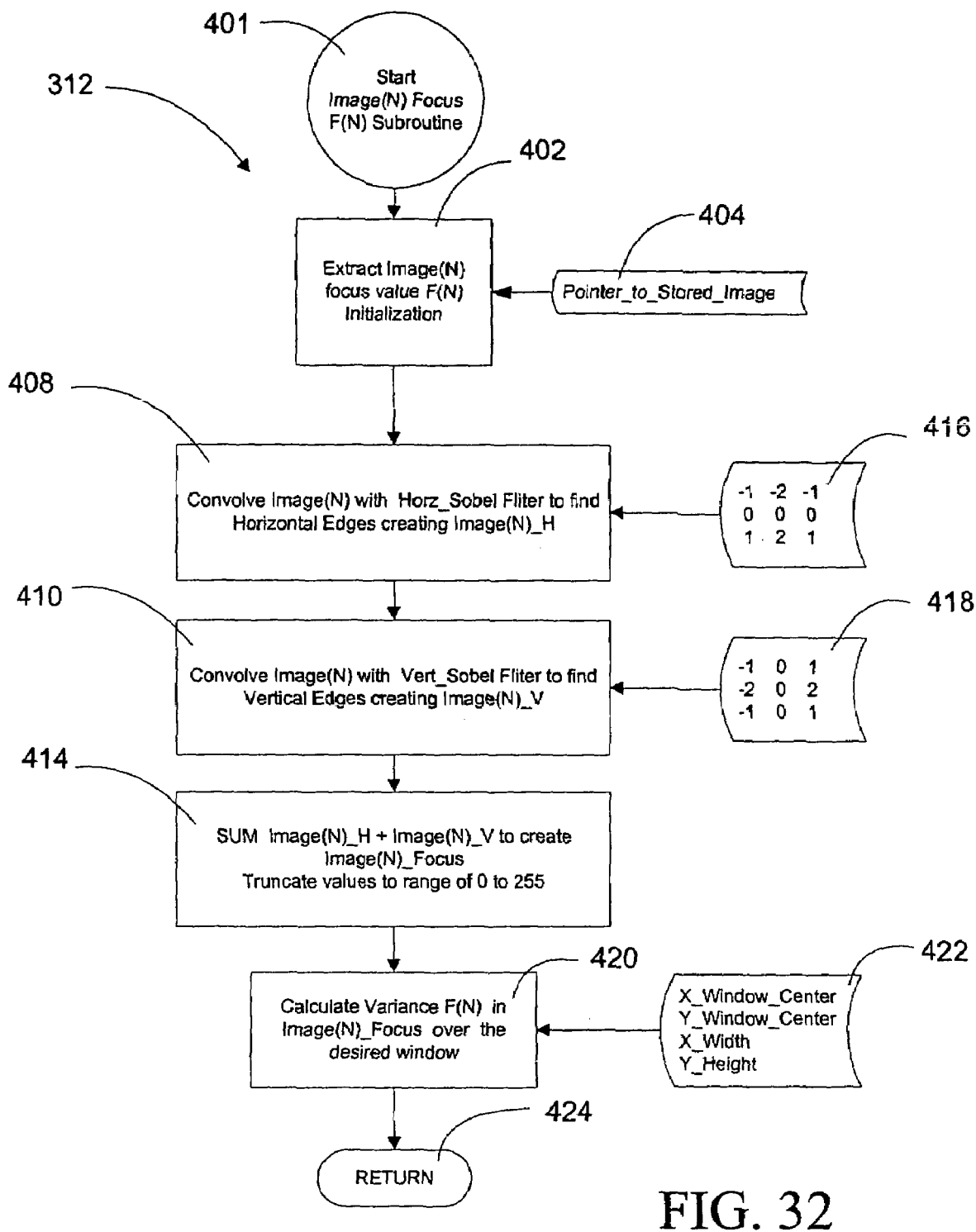
FIG. 32 shows a flowchart of a focus value subroutine.

As illustrated in FIG. 32. an image(N) focus F(N) subroutine 312 is further detailed, starting at the step Start 401. A pointer_to_image(N) 404 is provided in step 402. In step 408 the image(N) is convolved with a standard 3×3 Sobel_Horizontal filter 416 to produce an Image(N)_H wherein horizontal edges within the image are emphasized. In step 410 the image(N) is convolved with a standard 3×3 Sobel_Vertical filter 418 to produce an Image(N)_V wherein vertical edges within the image are emphasized. In step 414, both the horizontal edge emphasized image Image(N)_H and the vertical edge emphasized image Image(N)_V are summed pixel by pixel, during the summing process any resulting negative pixel values are set to zero and any resulting pixel values that are greater than 255 are set to 255, to produce an image Image(N)_Focus. In step 420, a simple variance F(N) is calculated for the pixels within a window of interest defined in 422 by X-Window_Center, Y_Window_Center, X_width, and Y_Height. The resulting value of the variance is returned to the calling program as F(N) in step 424. The sobel processing and the variance calculation is performed with a collection of image processing software tools within MVTools. MVTools is available from Coreco Imaging, US Office in Bedford, Mass.

Fourth Preferred Embodiment

In the first preferred embodiment, it was disclosed how an operator could manually score each drop of liquid as either "CRYSTAL" or "NO CRYSTAL". In the fourth preferred embodiment, the operator is given a greater variety of options in deciding on how to score each drop. Table 1 shows listing of the operator's scoring options, including number, text description, and the corresponding color code. Once a micro-well drop has been scored a 9, the operator can further classify the crystals in a scoring shown in Table 2.

TABLE 1

| SCORE | DESCRIPTION | DISPLAY COLOR |
|---|---|---|
| 0 | clear | White |
| 1 | light precipitation | Red |
| 2 | heavy precipitation | Yellow |
| 3 | ugly precipitation | Blue |
| 4 | phase separation | Orange |

TABLE 1-continued

| SCORE | DESCRIPTION | DISPLAY COLOR |
| --- | --- | --- |
| 5 | unknown | Violet |
| 6 | Spherolites | Black |
| 7 | Grainy precipitation | Gray |
| 8 | Microcrystals | Brown |
| 9 | Crystal | Green |

TABLE 2

| SCORE | DESCRIPTION |
| --- | --- |
| 9.0 | crystal (no comments) |
| 9.1 | needles, intergrown |
| 9.2 | needles, single |
| 9.3 | plates, intergrown |
| 9.4 | plates, single |
| 9.5 | chunks, <50 microns, intergrown |
| 9.6 | chunks, <50 microns, single |
| 9.7 | chunks, >50 microns, intergrown |
| 9.8 | chunks, >50 microns, single |
| 9.9 | gorgeous > 50 microns |

Fifth Preferred Embodiment

In the fourth preferred embodiment, it was disclosed how an operator can manually score each drop of liquid into one of 10 categories with corresponding color coding, and how the operator can score category 9 into further subcategories of 9.0 through 9.9. In the fifth preferred embodiment, the inspection device automatically scores and classifies each drop specimen by executing computer software subroutines as shown in FIGS. 33, 34a, 34b, 34c, 34d, and 35a and 35b under control of the program flow shown in FIG. 36. The automatic classification can occur at three levels of detail, the first level, Type_of_Classification=1, simply discriminates between a drop that is clear or not-clear (unknown), the second level, Type_of_Classification=2, scores and classifies the drop into classes 0 through 9 as described in Table 1 above, and the third level, Type_of Classification=3, performs second level scoring and classification, plus adds an additional 10 subcategories to the CLASS 9, crystal classification, as detailed in Table 2 above.

Automatic Scoring and Classification

Figure 36:
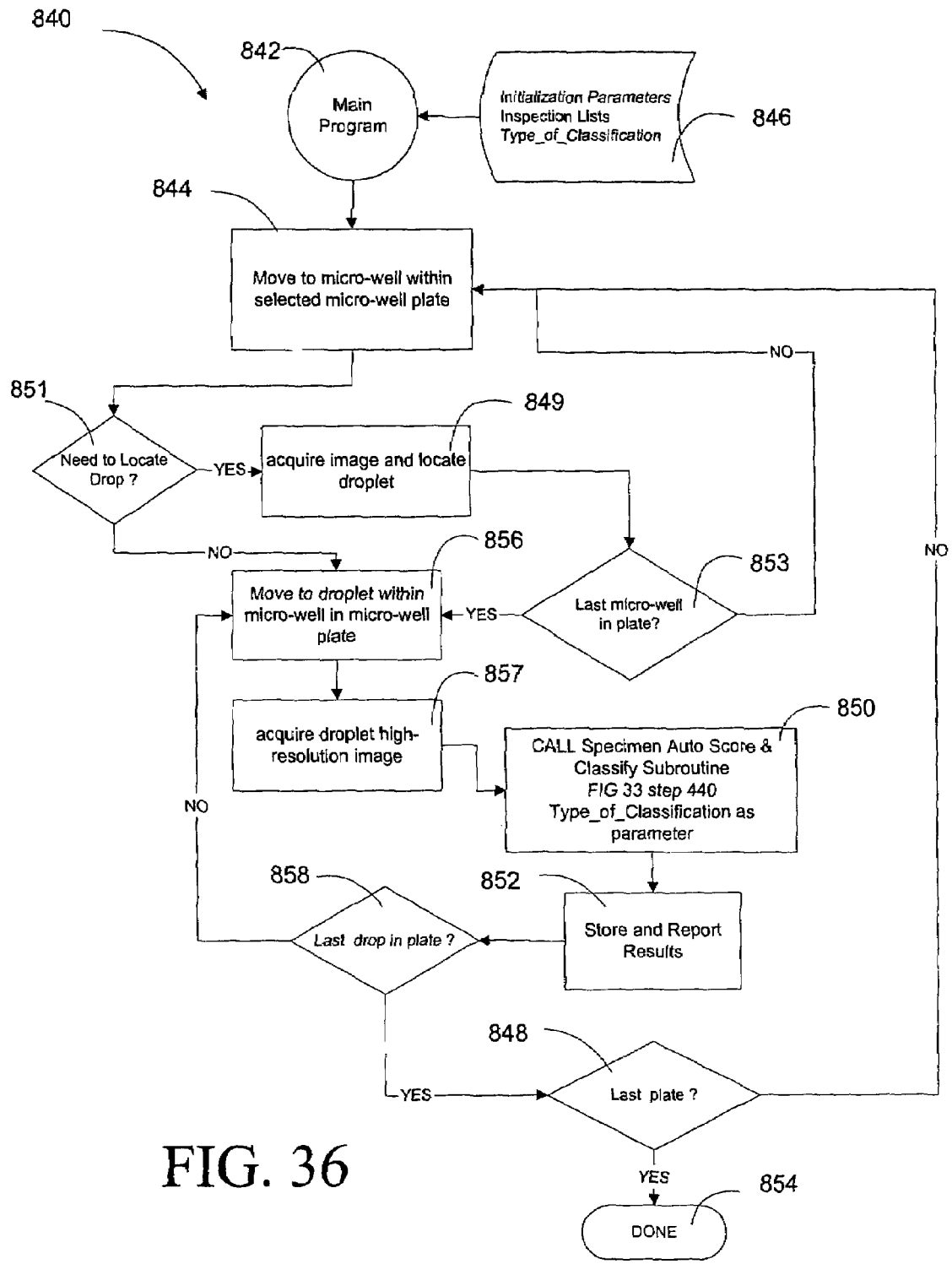
FIG. 36 shows the main program flow.

FIG. 36 illustrates the main program flow 840 starting at step 842. The software is initialized with parameters, inspection lists, and Type_of_Classification detailed in step 486. The flow continues onto step 844 where the system moves the micro-well of interest within the selected micro-well plate under the selected camera. In step 851, if the drop needs to be located, the flow continues onto step 849 wherein an image is acquired by the camera and software operates on the image and determines the location of the drop. Then a test is made to determine if the last micro-well in the plate has been imaged, if not then the flow loops to step 844 and continues. If the last micro-well in plate step 853 has been imaged then the flow continues to step 856 where the system moves to the droplet within micro-well in micro-well plate under the high-resolution camera. Also in step 851 if the drop had been previously located, then the flow would continue from step 844 directly to step 856 without the need to re-locate the drop. From step 856, the flow continues onto step 857 wherein a high-resolution image of the drop is obtained. Then the flow goes onto step 850. In step 850, a CALL is made to subroutine that automatically scores and classifies the drop depending on the Type_of_Classification required. The subroutine is detailed in FIG. 33 and starts at step 440 in FIG. 33. After the drop has been classified the subroutine returns to step 852 wherein the results are stored and reported. The program flow continues to step 858 where a test is made to determine if the last drop in the selected plate has been processed, if so then the flow goes onto step 848 wherein a test is made to determine if the last plate has been processed. If not, the flow loops back to 856 and continues. If the last plate has been processed, the flow goes onto step 854 and the program is done.

Figure 33:
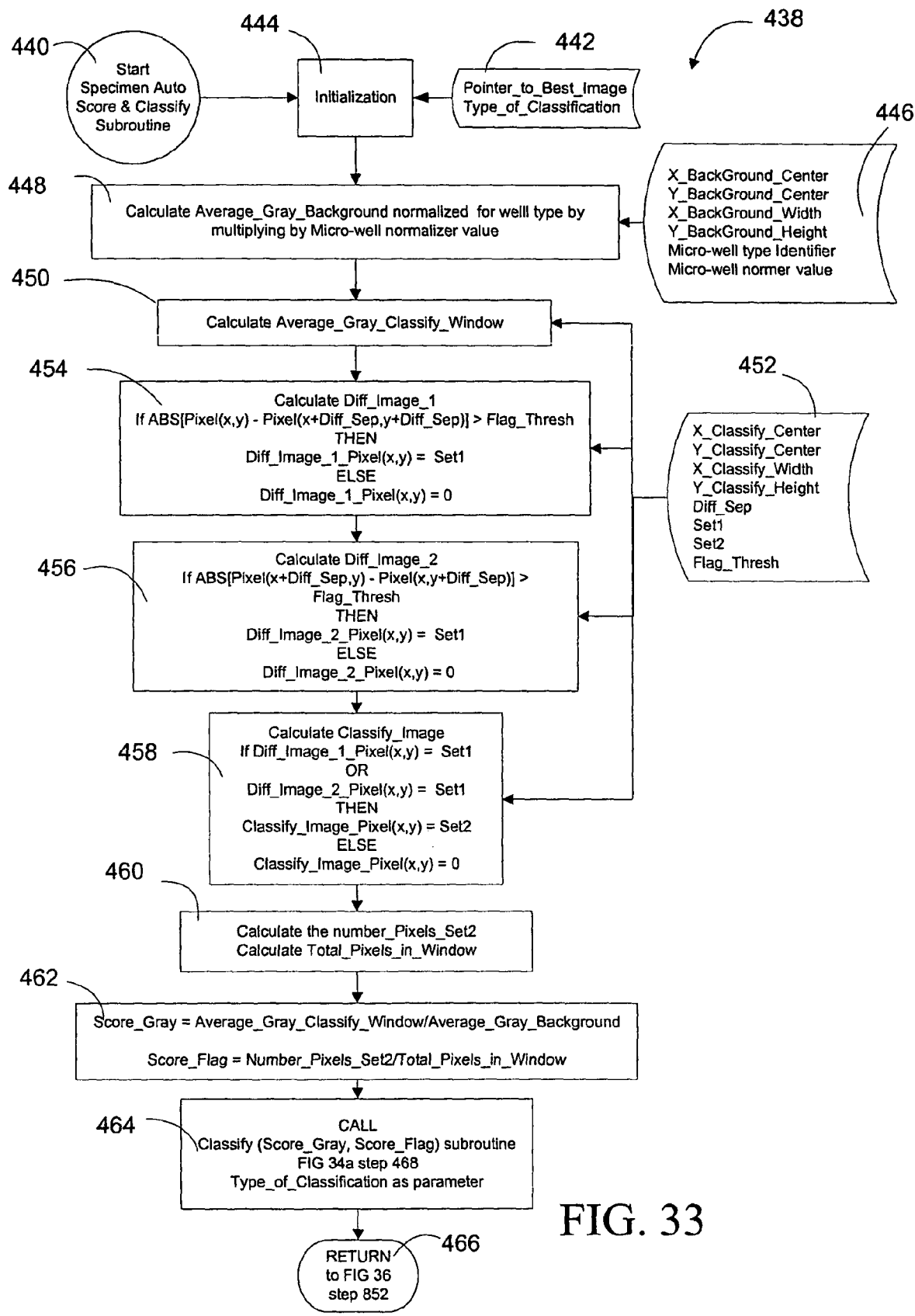
FIG. 33 shows a flowchart of the auto score and classify subroutine.

FIG. 33 shows Micro-well Specimen Auto Score and Classify Subroutine 438 starting at step 440. Pointer_to_Best_Image 442 provides information to the initialization step 444 that allows access to the image that was found to be the best focus. Plus, the Type_of_Classification is passed into the routine. Alternatively, pointer 442 can point to an image that was taken at a z height value known to be the focus of the system. After initialization 444 the subroutine 438 calculates in step 448 an average_gray_Background value normalized to allow for the variation present from various plate types, by using a first rectangular window defined by parameters shown in step 446 (X_Background_Center, Y_Background_Center, X_Background_Width, and Y_Background Height) and by summing all of the gray scale values of the pixels defined by the window 446 and dividing by the number of pixels within that window. The average_gray_background is normalized for well-type differences by multiplying the calculated value by a Micro-well normer value also found in step 446 and generally determined by measuring the various micro-well plate types under inspection and normalizing to the 96-well standard micro-well plate. This average_gray_background 448 is calculated in a window area of the image that is outside the area of the drop but generally within the well or within the bounding well walls.

In step 450 an average_gray_Classify_Window value is calculated in a similar manner as described above (except it is not normalized for micro-well type) using a second rectangular window defined by parameters shown in step 452 (i.e., X_Classify_Center, Y_Classify_Center, X_Classify _Width, and Y_Classify Height). This average_gray_classify_window value 450 is taken in a rectangular window area of the image that is inside the area of the drop and defined by being a fraction between 0.98 and 0.5 (with 0.8 preferred) of the width and height of the external bounding rectangular box from the blob utilizing subroutine mvt_blob_find. The subroutine mvt_blob_find defines the extent of the drop as previously discussed in the section "Determining the Position of the Drop of Liquid within Each Well".

In step 454, a diagonal difference image is calculated by stepwise subtracting pixel values from two pixel locations, defined by (x,y) and (x+Diff_Sep, y+Diff_Sep) within the Classify_window. The pixel values are separated in width and height by the value Diff_sep from step 452. This is repeated over all pixels within the Classify window defined by step 452 using X_Classify_Center, Y_Classify_Center, X_Classify _ Width, and Y_Classify Height. For each value calculated the absolute value is taken of the subtraction result and compared to a threshold value Flag_Thresh defined in step 452. If the calculated value is greater than Flag_Thresh 452 then the pixel is set at the first location in x,y equal to a value defined by Set1 in step 452, if the calculated value is equal to or less than Flag_Thresh, 452, then the pixel value is set to zero. This can be seen by the mathematical equations and flow described in step 454 in calculating a Diff_Image_1. Typical values for Diff_Sep are between 1 to 20 pixels with 7 preferred. Typical values for Set1 are between 1 and 511 with 128 preferred. Typical values for Flag_Thresh are between 5 and 50 with 25 preferred.

In Step 456, a calculation similar to that performed in step 454 is performed on the Classify_Window except that the separation between the two pixels undergoing the calculation is defined by (x+Diff_Sep, y) and (x, y+Diff_Sep), as is shown in the mathematical calculation in 456 to generate a Diff Image_2. This calculation uses definitions shown in step 452. Typical values for Set2 are between 1 and 511 with 200 preferred.

In Step 458 the Classify_Image, which is a combination of the images generated in step 454 and 456 is calculated as shown by the mathematical equations shown in step 458 using definitions shown in step 452. If the x,y pixel value in either Diff_Image_1 or Diff_Image_2 (steps 454 and 456 respectively) has a value equal to Set1 452 then the pixel value is set at (x,y) in Classify_Image equal to Set2 452. Otherwise, the value is equal to zero(0) as shown in the mathematical equations in step 458. The calculations are repeated for all pixels within the window defined in 452. The Classify_Image is basically an image of the classify_image_window wherein edges present within the original Best_Image are detected.

In step 460, the value of number_Pixels_Set2 is set equal to the total number of pixels that are set equal to Set2 452 in step 458. Also, the value of Total_Pixels_in_Window is set to the total number of pixels in the Classify_window in step 458.

In step 462, a Score_Gray is calculated by dividing the Average_Gray_Classify_Window determined in step 450 by the Average_Gray_Background found in step 448. A Score_Flag is also calculated by dividing the Number_Pixels_Set2 by Total_Pixels_in_Window from step 460. The Score_Gray and Score_Flag are normalized in this matter.

In step 464, the values of Score_Gray, Score_Flag, and Type_of_Classification are passed to a classify subroutine and a classification is returned for the Classify_image, effectively classifying the protein crystals within the window. Details of the Classify subroutine 464 are provided in FIG. 34a, 34b, 34c, and 34d, plus FIG. 35a and 35b.

Figure 34A:
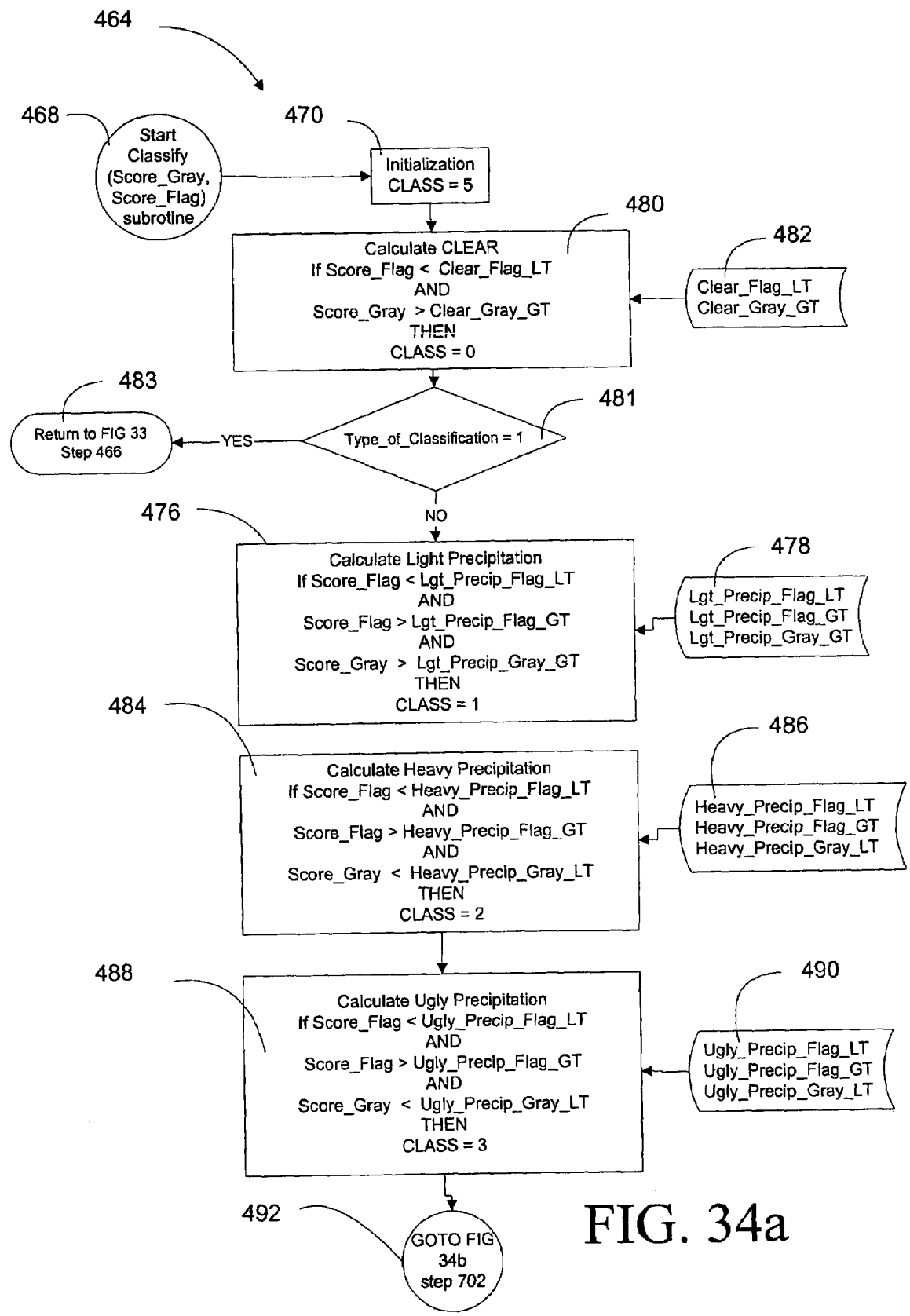
FIGS. 34a-34d show flowcharts of the classify subroutine.

FIG. 34a shows the Classify Subroutine 464. Start of Classify subroutine is shown in step 468 followed by initialization 470 whereby the initial classification CLASS value is set to 5, representing "unknown" and the flow goes onto step 480. Step 480 calculates whether the drop is clear and the CLASS=0 by a test detailed in step 480 using thresholds defined in step 482 (Clear_Flag_LT and Clear_Gray_GT) with the following equation: if score_flag is less than Clear_Flag_LT and Score_Gray is greater than Clear_Gray_GT then set CLASS=0. At step 481, a test is made to see of the type_of_classification is equal to 1, the first classification type wherein the drop is classified as simply clear (0) or unknown (5) as previously discussed. If the type_of_classification is equal to 1 then the flow goes on to step 483 and then returns to FIG. 33 step 466 with the results. If the type_of_classification is not equal to 1 then the flow goes onto step 476 for further classification.

Step 476, utilizing threshold value parameters shown in step 478 (Lgt_Precip_Flag_LT, Lgt_Precip_Flag_GT, Lgt_Precip_Gray_GT), assigns the value of 1 to CLASS indicating that Light Precipitation is present in the Classify_Image. Step 476 utilizes the mathematical equation which states if Score_Flag is less than Lgt_Precip_Flag_LT and Score_Flag is greater than Lgt_Precip_Flag_GT and Score_Gray is greater than Lgt_Precip_Gray_GT then set CLASS to value 1.

Step 484 calculates heavy precipation by using thresholds detailed in step 486 (Heavy_Precip_Flag_LT, Heavy_Precip_Flag_GT, Heavy_Precip_Gray_LT) with the following equation: if score_flag is less than Heavy_Precip_Flag_LT and score_flag is greater than Heavy_Precip_Flag_GT and score_gray is less than Heavy_Precip_Gray_LT then set CLASS=2.

Step 488 calculates ugly precipation by using thresholds detailed in step 490, Ugly_Precip_Flag_LT, Ugly_Precip_Flag_GT, Ugly_Precip_Gray_LT, with the following equation: if score_flag is less than Ugly_Precip_Flag_LT and score_flag is greater than Ugly_Precip_Flag_GT and score_gray is less than Ugly_Precip_Gray_LT then set CLASS=3.

Figure 34B:
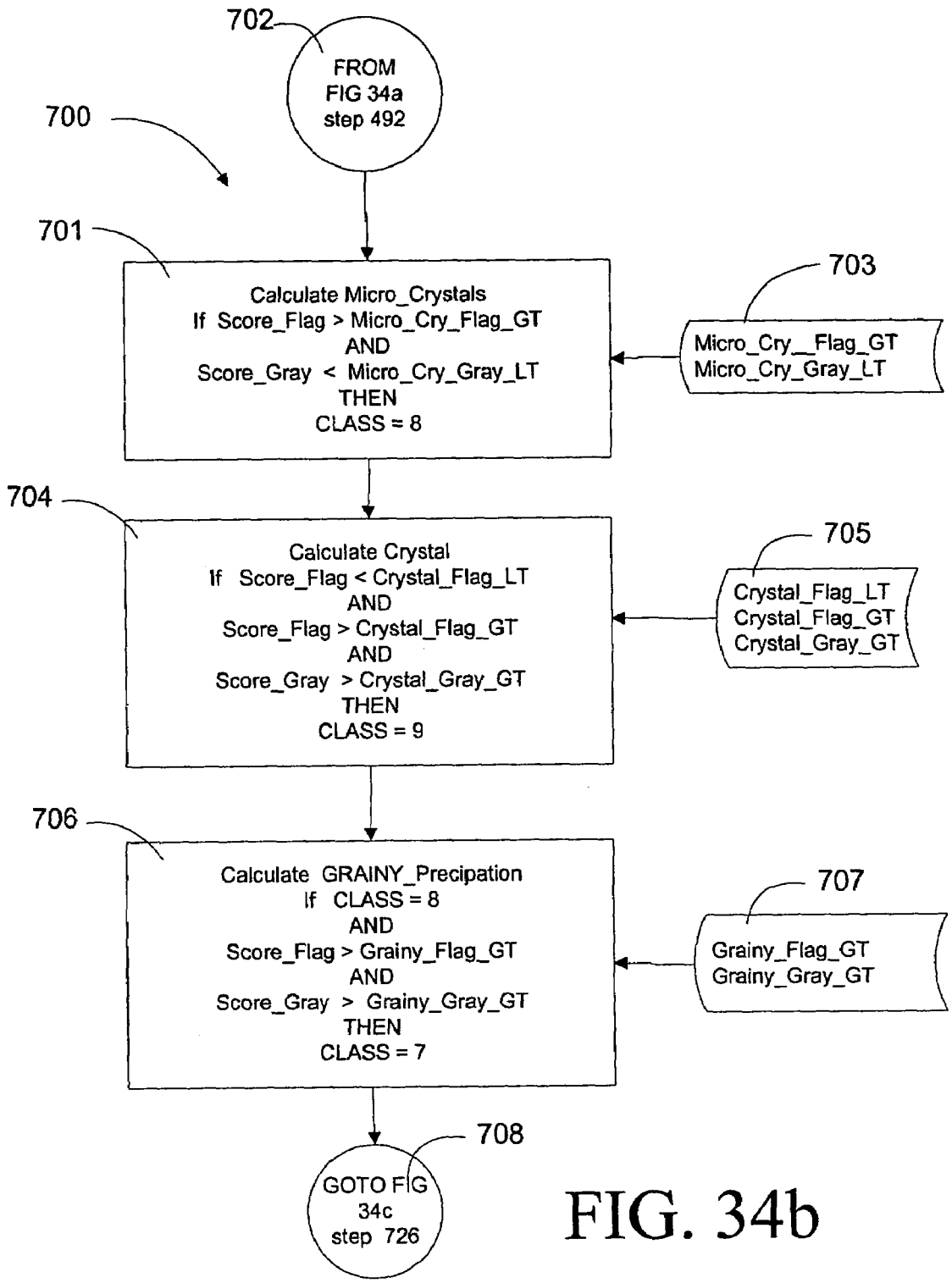

Step 492 continues the classification process in FIG. 34b.

In FIG. 34b, the continuation of the classification process 700 is shown continuing in step 702. Step 704 calculates micro_crystals by using thresholds detailed in step 703 (Micro_Cry_Flag_GT and Micro_Cry_Gray_LT) with the following equation: if score_flag is greater than Micro_Cry_Flag_GT and score_gray is less than Micro_Cry_Gray_LT, then set CLASS=8.

Step 704 calculates crystals by using thresholds detailed in step 705 (Crystal_Flag_LT, Crystal_Flag_GT, and Crystal_Gray_GT) with the following equation: if score_flag is less than Crystal_Flag_LT and score_flag is greater than Crystal_Flag_GT and score_gray is greater than Crystal_Gray_GT then set CLASS=9.

Step 706 calculates Grainy precipitation by using thresholds detailed in step 707 (Grainy_Flag_GT, and Grainy_Gray_GT) with the following equation: if CLASS=8 and score_flag is greater than Grainy_Flag_GT and score_gray is greater than Grainy_Gray_GT, then set CLASS=7.

Figure 34C:
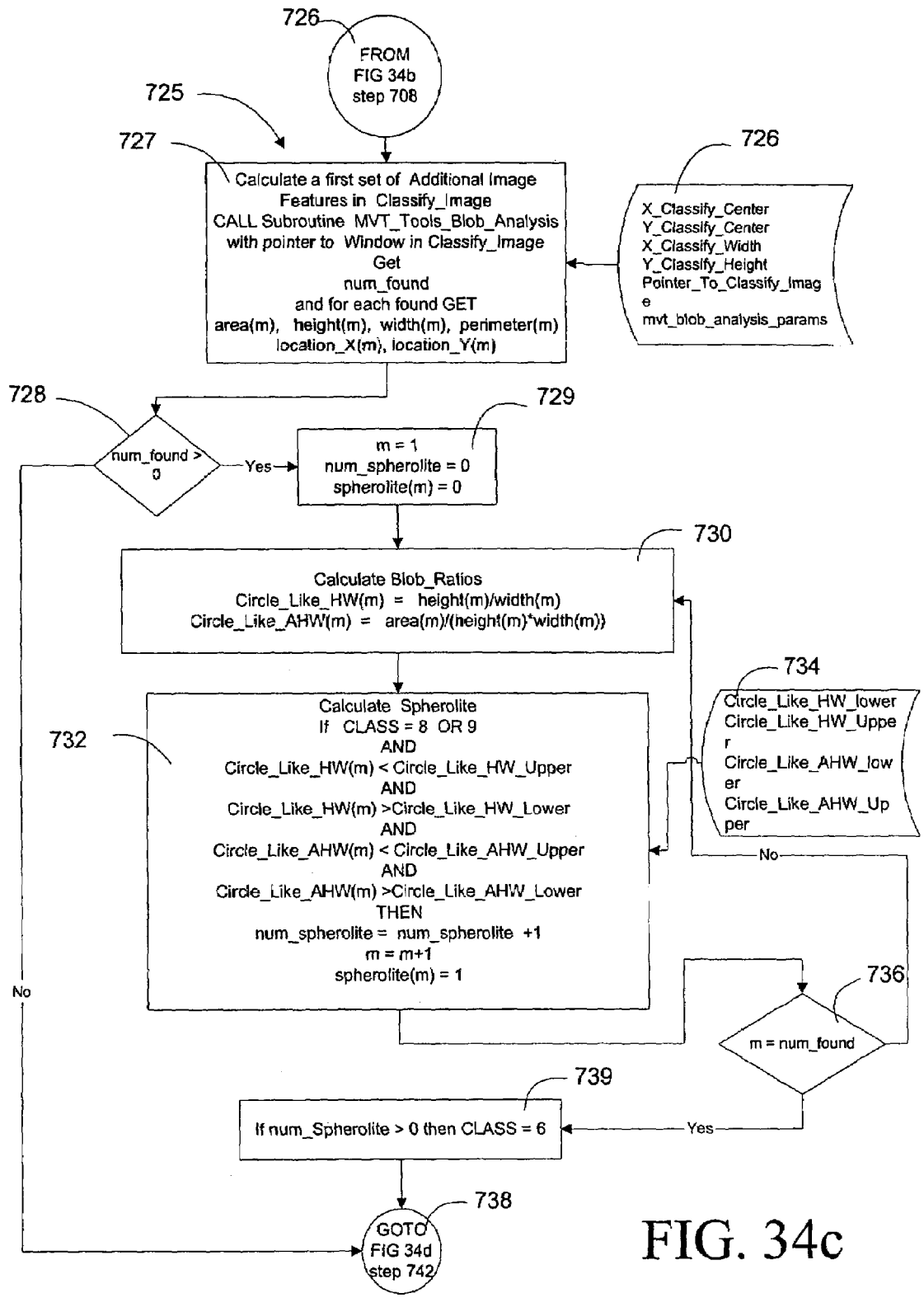

Step 708 continues the classification process onto FIG. 34c as 725.

Step 726 continues from step 708 of FIG. 34b.

In FIG. 34c, Step 727 calculates and generates a first set of additional image features for further use in classification taking as input 726 (X_Classify_Center, Y_Classify_Center, X_Classify_Width, Y_Classify Height, Pointer_to_classify_image, and mvt_blob_analysis_Params). In step 727, MVT_Tools_Blob_Analysis with pointer to window in Classify_Image is called. Step 727 gets the num_found of blobs and, for each blob found, step 727 gets its area(m), height(m), width(m), perimeter(m), and location of each as location_X (m) ands location_Y(m). These values are recorded. These calculations are performed on the image called Classify_Image, which is the image that was formed in FIG. 33 as step 458.

In step 728, if num_found is not greater than zero(0) the subroutine goes to step 738. However, if any blobs are found then further analysis is started in step 729 by setting m=1, num_spherolite=0, and spherolite(m)=0. In step 730, the following blob_ratios are calculated: Circle_Like_HW(m)= height(m)/Width(m) and Circle_Like_AHW(m)=area(m)/ (height(m)*width(m)). For blobs that are circular, Circle_Like_HW will be around a value of one (1). If blobs get elongated then the value will be other than one. Circle_Like_AHW for circular blobs has a value around 0.785. For square-like blobs the value will be closer to one (1). The program flow goes onto step 732.

Step 732 determines whether to classify a drop as having a spherolite by utilizing the parameters found in 734 (Circle_Like_HW_lower, Circle_Like_HW_Upper, Circle_Like_AHW_Lower, and Circle_Like_AHW_Upper). The following equation is used:: if CLASS=8 or 9 and Circle_Like_HW(m) is less than Circle_Like_HW_Upper and Circle_Like_HW(m) is greater than Circle_Like_H-W_lower, and Circle_Like_AHW(m) is less than Circle_Like_AHW_Upper and Circle_Like_AHW(m) is greater then Circle_Like_AHW_Lower, then num_spherolite=num_sperolite+1. An increment is done by calculating m=m+1 and setting spherolite(m)=1 to show one has been found at m.

Step 736 tests whether all of the found blobs have been classified by testing m against num_found and, if equal, the subroutine goes onto step 738. If not the program loops back to step 730 and flows through as above.

Figure 34D:
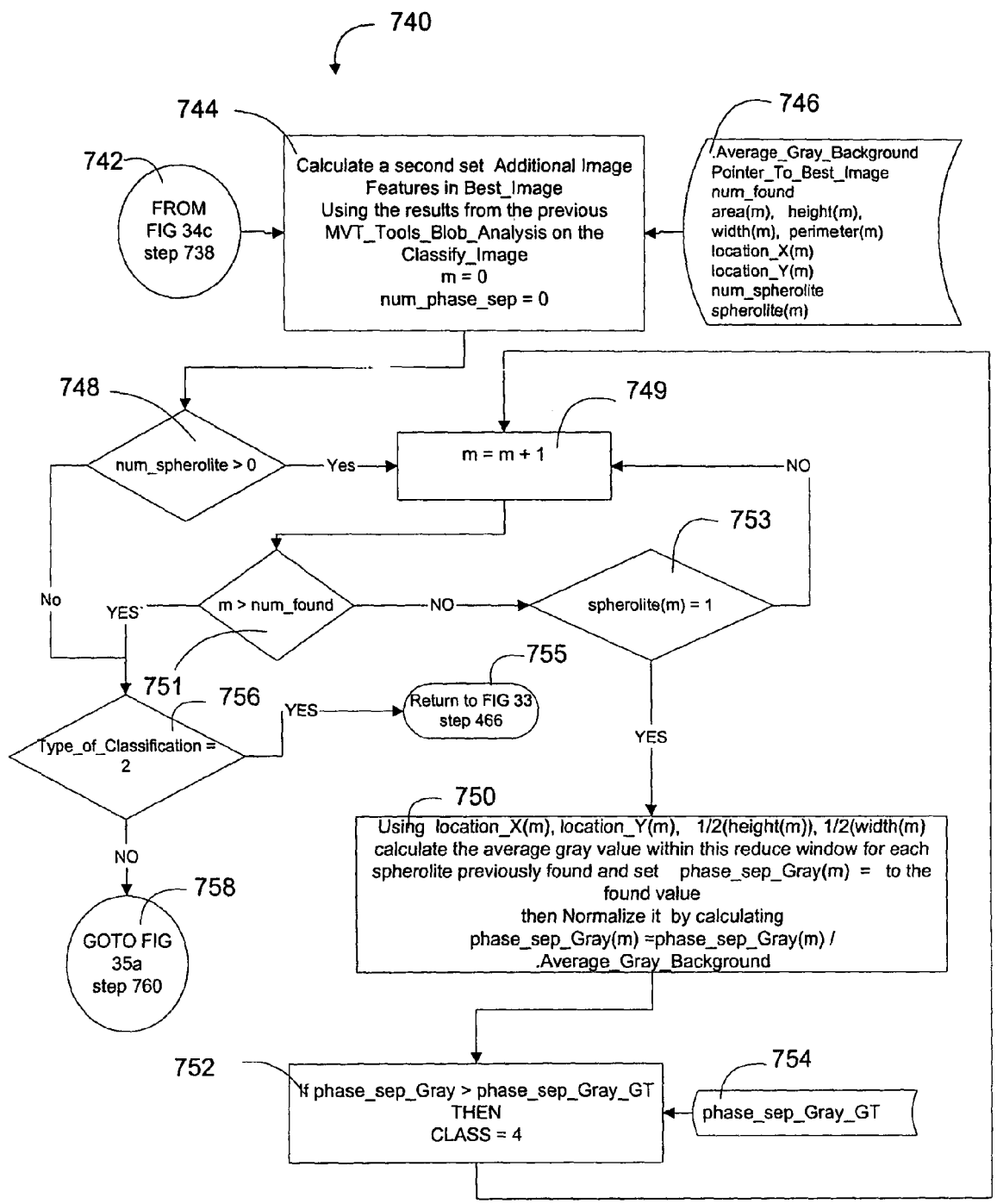

Step 738 goes onto FIG. 34*d* in the classification subroutine as 740.

FIG. 34*d* continues from FIG. 34*c* at 742 and goes to 744 where a second set of additional features is calculated. These features are generated with the original Best_Image generated in step 328 (FIG. 31) as the image of the best focus. For these additional features, the results are used from the blob analysis performed in FIG. 34*c* on the classify_image. Such features as shown in parameters 746 as num_found, area(m), height(m), width(m), perimeter(m), location_X(m), location_Y(m), num_spherolite, and spherolite(m). Plus it uses the average_gray background from FIG. 33 step 448, and the pointer_to_Best_Image in FIG. 31 step 328. In step 744 "m" and num_phase_sep are set equal to zero.

In step 748, if the number of spherolites previously found (num_spherolite) is not greater than zero (0), then the flow goes to step 756 and the remaining steps shown in FIG. 34*d* are bypassed. But if the num_spherolite is greater than zero (0), then the flow goes onto step 749 wherein m is incremented by 1. Then the flow goes on to step 751 to test whether to go to step 756 or to step 753 depending on comparing "m" to the num_found. In step 753, the value of spherolite(m) found in FIG. 34*c* step 732 is tested to see if any were classified as spherolite. If not, then the flow loops back to step 749. If spherolite(m) is equal to one (1) then step 750 is executed.

In step 750, the information location_X(m), location_Y (m), one half of height(m) and one half of width(m) is used to calculate the average gray value within this reduced image inside each spherolite. The Best_Image pixel data obtained from the previous blob analysis is utilized and phase_sep_Gray(m) is set equal to this value. Phase_sep_Gray(m) is then normalized by dividing it by the Average_Gray_Background. The program flow goes onto step 752, wherein phase_sep_Gray(m) is tested to see if it is greater than a parameter phase_sep_Gray_GT from parameter input step 754. If true, then CLASS is set equal to four(4) and the program loops up to step 749.

In step 751 the automatic program has classified the microdrop into one of the 10 primary classes, 0 through 9, detailed previously in Table 1. Then, a test is made to see if the type_of_classification is equal to 2. If so, then the flow goes onto step 755 wherein the flow is returned to FIG. 33. In step 466, a general classification is complete. If further classification into subcategories is required, then the flow goes onto step 758.

Figure 35A:
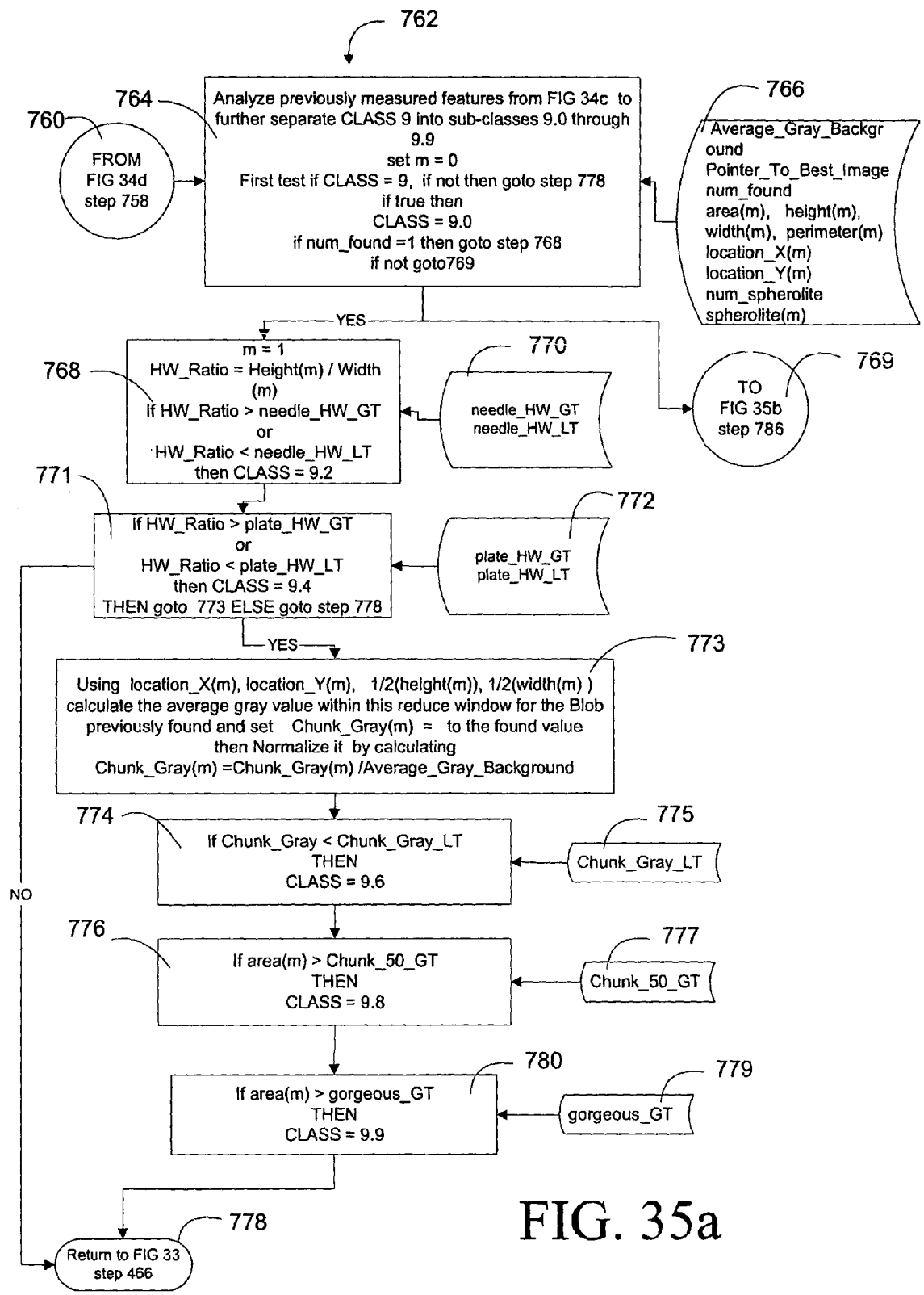
FIG. 35a-35b show the sub-classification of the crystal class.

In step 758, the program flow goes onto FIG. 35*a* step 760. In FIG. 35*a*, a crystal classification subroutine 762 further classifies any CLASS 9 crystal image into to additional subclasses, 9.2, 9.4, 9.6, 9.8, or 9.9, as previously discussed in Table 2. The subroutine begins at step 760 and goes onto step 764. In step 764, the blob counter m is set to zero. A test is conducted to see if the CLASS is equal to 9 and, if not, the flow goes to step 778 and returns to FIG. 33 step 466. Step 764 uses input values as shown in step 766 (Average_Gray_Background, Pointer_To_Best_Image, num_found, area(m), height(m), width(m), perimeter(m), location_X(m), location_Y(m), num_spherolite, and spherolite(m)), as previously described. If the CLASS is equal to 9 another test is made to see if one or more than one blobs were previously found. If only one blob was previously found then the flow goes onto step 768. If more then one is found, the flow goes onto step 769 in FIG. 35*b*. In step 768, a height to width ratio is calculated and compared to thresholds representing needle-like characteristics in step 770. If the test conditions are met, then the CLASS is set to 9.2. If not, the flow goes onto step 771. In step 771, the height to width ratio is compared to thresholds representing plate-like characteristics in step 772. If the conditions of the test are met, the CLASS is changed to 9.4 and the flow goes onto step 773. If not, no further classification is performed and the flow goes onto step 778 and the subroutine returns to FIG. 33 step 466. In step 773, a normalized average gray value, Chunk_Gray(m), within the blob is calculated and the flow goes onto step 774. In step 774, if Chunk_gray(m) is less than a threshold Chunk_Gray_LT (from step 775), then CLASS is set to 9.6 and the flow goes onto step 776. In step 776, if Chunk_gray(m) is greater than a threshold Chunk_50_GT, (from step 777), then CLASS is set to 9.8 and the flow goes onto step 780. In step 780 if area(m) is greater than threshold gorgeous_GT (from step 779), then CLASS=9.9 and the flow goes onto step 778. Then the subroutine returns to FIG. 33 step 466.

Figure 35B:
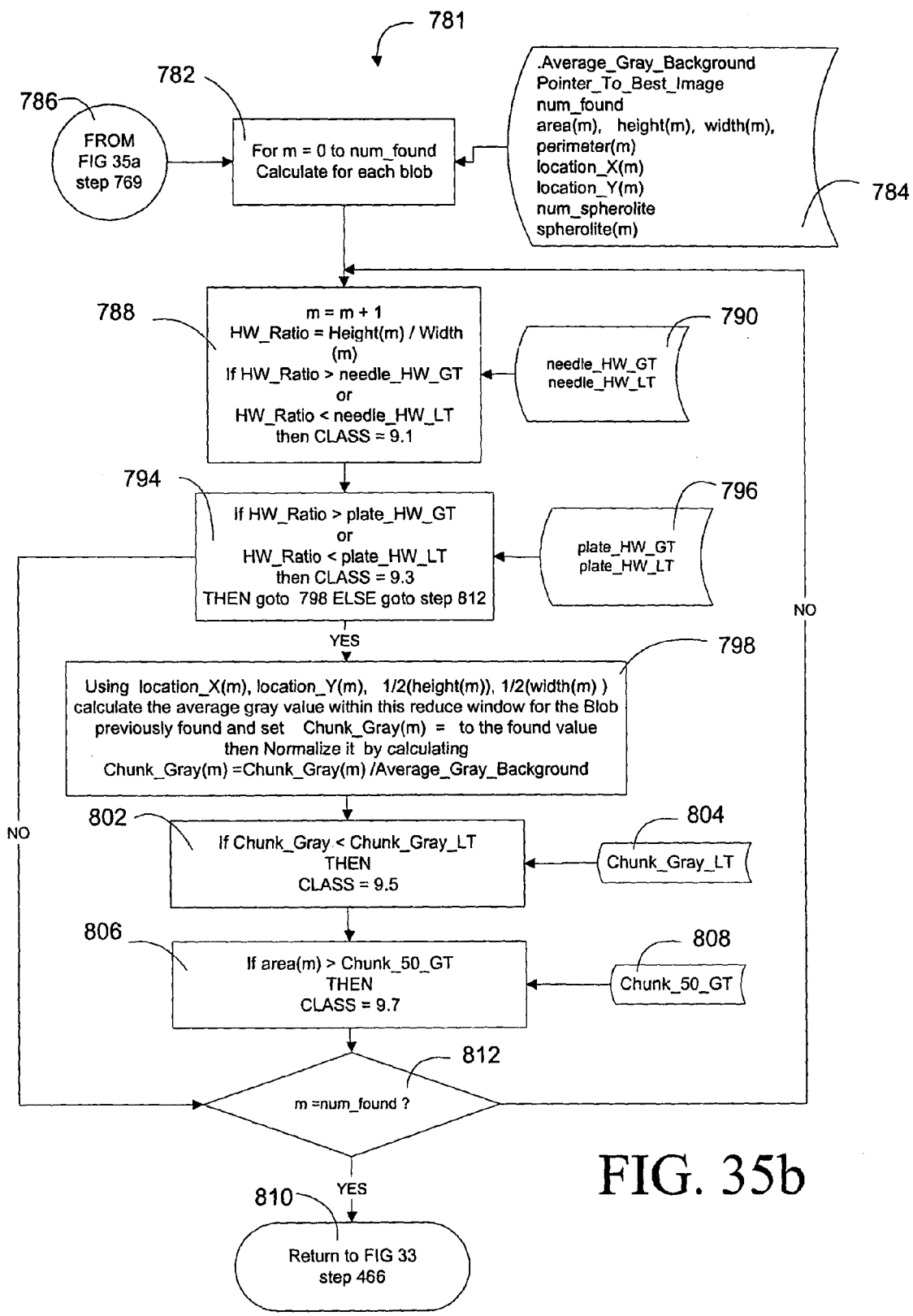

FIG. 35*b* shows flowchart 781 illustrating the further classification of a CLASS 9 image having multiple blobs within the image into additional subclasses, 9.1, 9.3, 9.5, or 9.7, as previously discussed in Table 2. The subroutine begins at step 786 from step 769 in FIG. 35*a* and goes onto step 782. In step 782, a loop begins at m equals 0 for each blob m using input values from step 784 (Average_Gray_Background, Pointer_To_Best_Image, num_found, area(m), height(m), width(m), perimeter(m), location_X(m), location_Y(m), num_spherolite, and spherolite(m)) as previously described. The flow goes onto step 788 where m is incremented and a height to width ratio is calculated and compared to thresholds representing needle-like characteristics in step 790. If the test conditions are met, then the CLASS is set to 9.1. If not, the flow goes onto step 794. In step 794, the height to width ratio is compared to thresholds representing plate-like characteristics in step 796. If the conditions of the test are met, the CLASS is changed to 9.3. If not, no further classification is performed and the flow goes onto step 812 to determine if all of the lobs have been tested. In step 798, a normalized average gray value (Chunk_Gray(m) as described before) within the blob is calculated and the flow goes onto step 802. In step 802, if Chunk_gray(m) is less than a threshold Chunk_Gray_LT (from step 804) then CLASS is set to 9.5 and the flow goes onto step 806. In step 806, if Chunk_gray(m) is greater than a threshold Chunk_50_GT (from step 808) then CLASS is set to 9.7 and the flow goes onto step 812. In step 812, if all of the blobs have been tested, the flow goes onto step 810 and the subroutine returns to FIG. 33 step 466. If not all tested, then the flow loops back to step 788 for the next blob and the process loops until complete.

Typical parameter and threshold values for use in classification in FIGS. 33, 34*a*, 34*b*, 34*c*, 34*d*, and 35*a* and 35*b* are given in Table 3 along with the preferred value. These values serve only as a guide, and other values may be used when circumstances justify. For example, different lighting conditions, variations in the transparency of micro-well plates, variations in the formulations of the protein growing media and drop, values may be used as well. One skilled in the art may adjust the parameter and threshold values to tune in the classification results specific to their setup.

TABLE 3

Typical and preferred values for threshold and Classification parameters

| Step | Name | lower value | upper value | Preferred value |
|---|---|---|---|---|
| 452 | Diff_Sep | 1 | 20 | 7 |
| 452 | Set1 | 1 | 511 | 128 |
| 452 | Set2 | 1 | 511 | 200 |
| 452 | Flag_Thresh | 5 | 50 | 25 |
| 478 | Lgt_Precip_Flag_LT | 0.0001 | 0.010 | 0.002 |
| 478 | Lgt_Precip_Flag_GT | 0.0 | 0.001 | 0.00001 |
| 478 | Lgt_Precip_Gray_GT | 0.8 | 1.2 | 1.020 |
| 482 | Clear_Flag_LT | 0.000001 | 0.01 | 0.0007 |
| 482 | Clear_Gray_GT | 0.8 | 1.2 | 1.020 |
| 486 | Heavy_Precip_Flag_LT | 0.0001 | 0.050 | 0.020 |
| 486 | Heavy_Precip_Flag_GT | 0.0 | 0.005 | 0.001 |
| 486 | Heavy_Precip_Gray_LT | 0.7 | 1.2 | 0.95 |
| 490 | Ugly_Precip_Flag_LT | 0.0001 | 0.050 | 0.020 |
| 490 | Ugly_Precip_Flag_GT | 0.0 | 0.005 | 0.001 |
| 490 | Ugly_Precip_Gray_LT | 0.5 | 1.2 | 0.7 |
| 703 | Micro_Cry_Flag_GT | 0.0001 | 0.05 | 0.020 |
| 703 | Micro_Cry_Gray_LT | 0.9 | 1.20 | 1.010 |
| 705 | Crystal_flag_LT | 0.1 | 0.5 | 0.30 |
| 705 | Crystal_Flag_GT | 0.001 | 0.05 | 0.01 |
| 705 | Crystal_Gray_GT | 0.8 | 1.2 | 1.0099 |
| 707 | Grainy_Flag_GT | .001 | .5 | 0.177 |
| 707 | Grainy_Gray_GT | 0.8 | 1.2 | 0.980 |
| 734 | Circle_Like_HW_lower | 0.5 | 1.00 | 0.9 |
| 734 | Circle_Like_HW_Upper | 1.00 | 2.0 | 1.1 |
| 734 | Circle_Like_AHW_lower | 0.1 | 3.9 | 0.78 |
| 734 | Circle_Like_AHW_Upper | .785 | 2.0 | 0.83 |
| 754 | phase_sep_Gray_GT | 0.9 | 1.2 | 1.05 |
| 770, 790 | needle_HW_GT | 2 | 20 | 5 |
| 770, 790 | needle_HW_LT | 0.5 | 0.05 | 0.2 |
| 772, 796 | plate_HW_GT | 1.1 | 2.0 | 0.95 |
| 772, 796 | plate_HW_LT | 0.9 | 1.1 | 1.05 |
| 775, 804 | Chunk_Gray_LT | 0.8 | 1.2 | 1.01 |
| 777, 808 | Chunk_50_GT | 70 | 200 | 100 |
| 779 | Gorgeous_GT | 7000 | 2000 | 1000 |

Prototype

Applicants have designed, built and tested a working prototype of the present invention.

Figure 30:
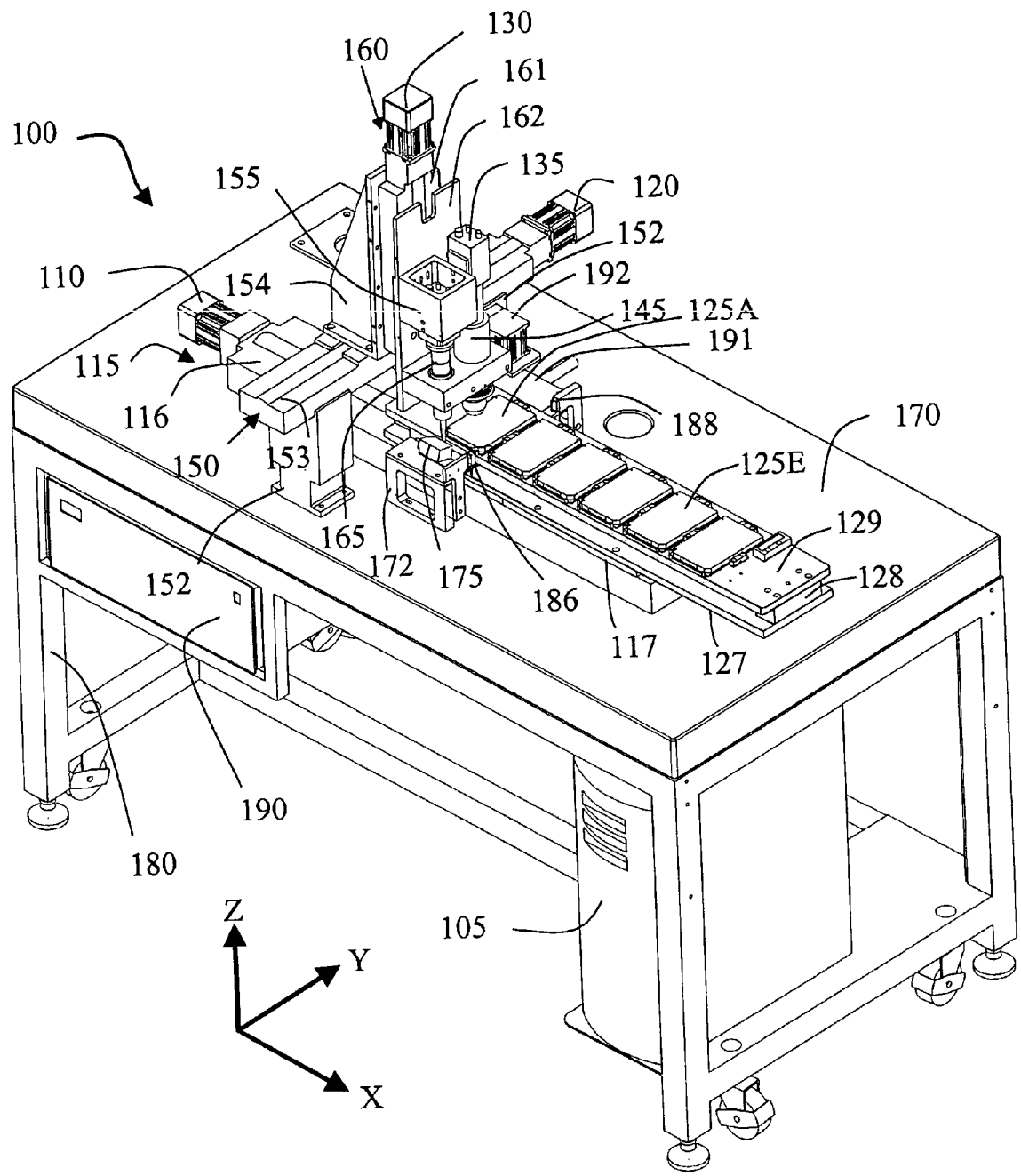
FIG. 30 shows a preferred embodiment of the present invention.

FIG. 30 shows the major components of the Applicant's prototype. Proteomic crystal verification and inspection system 100 has three axis of linear motion. Linear actuator 115 is preferably linear actuator model #802-0763D available from Dynamic Solutions of Irvine Calif., with 600 mm of travel driven by an enclosed 0.5 mm pitch ballscrew. Linear actuator 115 is driven by an intelligent self-contained servo motor 110 model #SM2320 SQ available from Animatics Corp. of Santa Clara, Calif., with 38 oz-in of available torque. Servo motor 110 communicates with a Windows Based computer 105 through a serial connection routed through a central control unit 190.

Linear actuator 115 has stationary part 116 fixed to a granite table top 170. Motor 110 moves moving part 117 along the x-axis. Granite top 170 is supported by a frame 180. Frame 180 has casters and adjustable legs. Plate 127 is attached to moving part 117. At each end of plate 127, a spacing block 128 spaces fixture plate 129 from plate 127. At each of its ends, fixture plate 129 is supported by spacing block 128. Fixture plate 129 provides for the mounting, removal, and positioning of multiple micro-well plates 125A-125F. Preferably micro-well plates 125A-125F are agar plates, microtiter well plates of 96, 384, 1536 wells, or other sample plates.

Support 191 is positioned adjacent to fixture plate 129 and contains a light source. In the preferred embodiment, the light source is model #A08925 fiber-optic back light available from Aegis Electronics of Carlsbad, Calif.

In the preferred embodiment, linear actuator 150 is model #802-1384A available from Dynamic Solutions of Irvine Calif., with 350 mm of travel driven by an enclosed 0.5 mm pitch ballscrew. Linear actuator 150 has stationary part 153 horizontally bridged above linear actuator 115 and supported by pillars 152. Moving base 154 provides a mounting base for components of linear actuator 160. In a preferred embodiment, linear actuator 150 is driven by driven by an intelligent self-contained servo motor 120 identical to motor 110. Servo motor 120 communicates with Windows Based computer 105 through a serial connection routed through central control unit 190.

In a preferred embodiment, linear actuator 160 is model #802-0756D available from Dynamic Solutions of Irvine Calif., with 100 mm of travel driven by an enclosed 0.5 mm pitch ballscrew. Linear actuator 160 has with a stationary part 161 mounted perpendicular to and fixed to moving base 154 of linear actuator 150. Linear actuator 160 is driven by intelligent self-contained servo motor 130. Servo motor 130 is preferably identical to motor 110. Servo motor 130 communicates with the Windows Based computer 105 through a serial connection routed through the central control unit 190.

Moving plate 162 provides a mounting base for camera 155. In a preferred embodiment camera 155 is a high-resolution monochrome megapixel CCD camera model #CVM1 from JAI America INC. of Laguna Hills, Calif. Camera 155 has lens 165. Preferably, lens 165 has a 0.75× to 3× zoom capability and is model #NT52-571 available from Edmund Industrial Optical of Barrington, N.J. Moving plate 162 also provides a mounting base for camera 135. Preferably, camera 135 is a high-resolution monochrome megapixel CCD camera model #CVM1 from JAI America INC. of Laguna Hills, Calif. Camera 135 has lens 145. Preferably, lens 145 has a 2.5× to 10× zoom capability and is model #NT54-396 available from Edmund Industrial Optical of Barrington, N.J.

Moving plate 162 also provides a mounting base for a zoom lens motor 192, an intelligent self-contained servo motor model #SM2315D available from Animatics Corp. of Santa Clara, Calif., with 20 oz-in of available torque. The servo motor communicates with the Windows Based computer 105 through a serial connection routed through the motion control box 190. The zoom lens motor operates the zoom lens 145 through a conventional belt drive.

A bar-code reader 175 is mounted adjacent linear actuator 115 and is attached to support 172 fixed on granite top 170. Bar-code reader 175 is positioned to view a bar-code identity label attached to a micro-well plate when the micro-well plate is positioned under linear actuator 150. Preferably, bar-code reader 175 is model #BL601 available from Keyence Corporation of America of Newark, N.J.

A plate sensor transmitter/receiver 186 is also fixed to support 172 and is aligned to sense whenever a micro-well plate 125 breaks a beam of light emitted by transmitter/receiver 186 and reflected by a reflector 188. Reflector 188 is mounted on support 191 on the opposite side of the linear actuator 115. Plate sensor transmitter/receiver 186 and reflector 188 are preferably model #E3T-SR13 available from Western Switch Controls of Santa Ana, Calif.

Block Diagram Showing Connectivity of the Prototype

Figure 6:
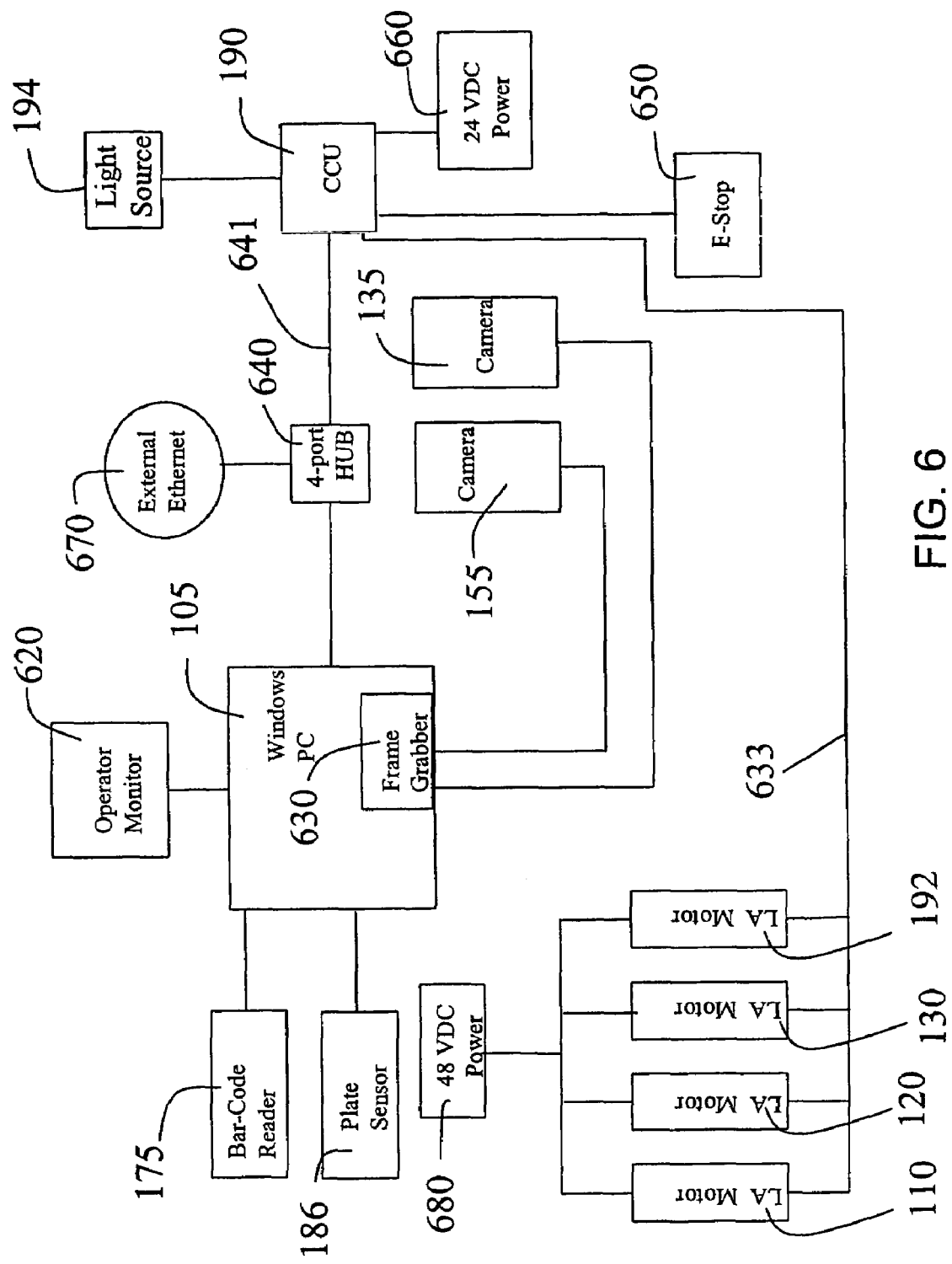
FIG. 6 shows a block diagram of a preferred embodiment of the present invention.

FIG. 6 shows a block diagram illustrating the connectivity of Applicant's prototype. Linear actuator motors 110, 120 and 130, and zoom motor 192 receive DC power from 48 Volt DC power supply 680 through an electrical connection. Linear actuator motors 110, 120 and 130, and zoom motor 192 motors communicate with Windows-based computer 105 through common serial line 633. Bar-code reader 175 communicates with computer 105 through a communications line and plate sensor 186 communicates with the computer 105 through a communications line. Monitor 620 displays information to the operator transmitted from computer 105. Cameras 135 and 155 communicate with frame grabber 630 through communication lines. Frame grabber 630 is installed within computer 105 and is preferably PCVision from Coreco Imaging US Office in Bedford, Mass. Frame grabber 630 digitizes the image from the camera to form the digitized image data array within computer 105. A 4-port Ethernet hub 640 provides for connectivity between computer 105, central control unit 190, and an external Ethernet 670. By providing for connectivity to the Ethernet, computer network communications are possible. The central control unit 190 controls light source 194 through an analog control line. Central control unit 190 receives 24 volt DC power from 24 volt DC power supply 660. Emergency stop button and switch (e-stop) 650 is connected to central control unit 190.

Experimental Results

Fifty-three test images were obtained from the system and were both automatically classified by the system and were manually classified by four scientists. Table 4 shows the correlation percentage between the various scientists and the automatic classification provided by the system.

TABLE 4

|  | Sam | Mary | Susan | Fred | AUTO |
|---|---|---|---|---|---|
| Sam | 100% |  |  |  |  |
| Mary | 98% | 100% |  |  |  |
| Susan | 93% | 97% | 100% |  |  |
| Fred | 89% | 93% | 96% | 100% |  |
| AUTO | 95% | 93% | 86% | 81% | 100% |

Utilization of Color

In another preferred embodiment, the present invention is configured to record color images. It is desirable to be able to analyze color images in that certain precipitation products in the protein crystallization process have distinctive colors and a crystallographer or automated image analysis algorithm may use the color information to help discriminate crystallization results.

True Color Picture

Figure 37:
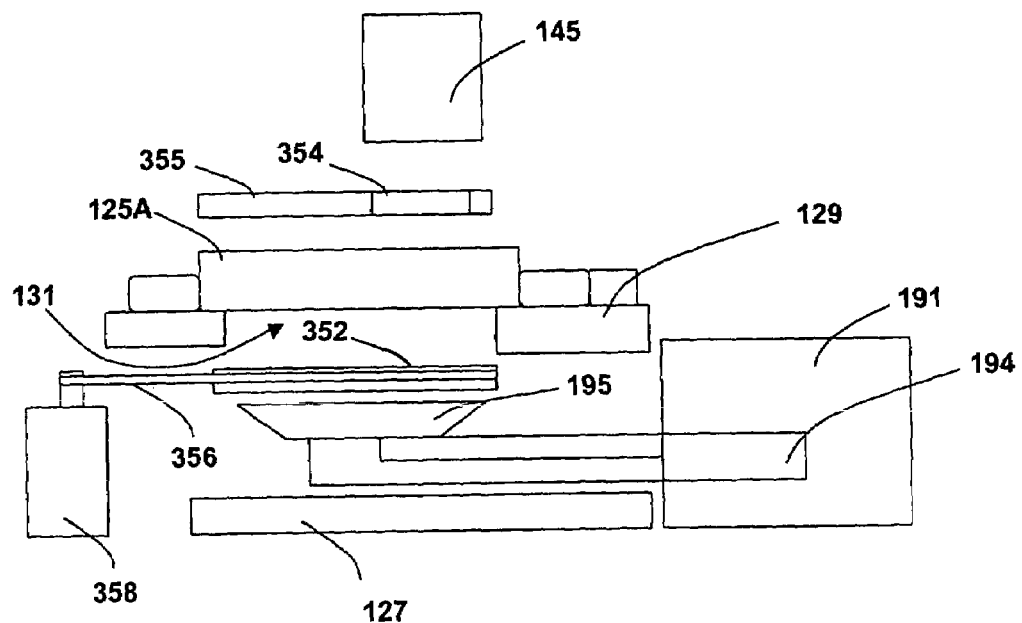
FIG. 37 illustrates a side view illustrating dual filters in the light path.

FIG. 37 shows a side view of micro-well plate 125A positioned on fixture plate 129. Support 191 with embedded light source 194 is positioned to the side of fixture plate 129. Light from light guide 195 is directed upward through cutout 131. Light guide 195 is positioned between fixture plate 129 and plate 127 such that both plates can move around the light guide 195 without interference.

Figure 38:
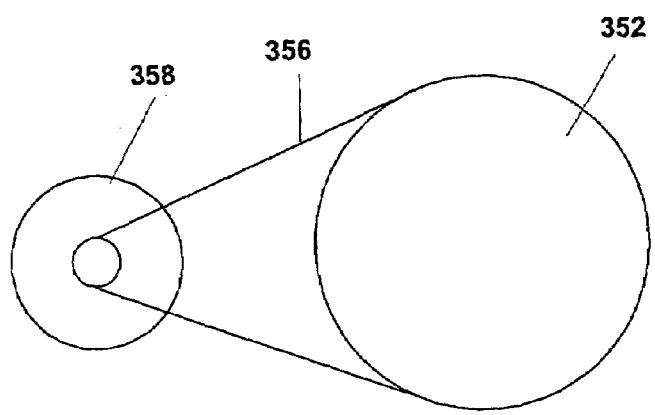
FIG. 38 illustrates a top view of the drive mechanism for the rotatable linear polarized filter.
Figure 39:
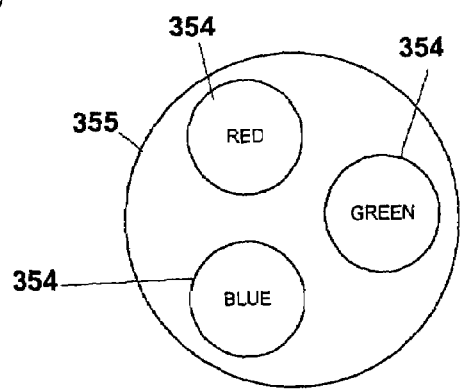
FIG. 39 illustrates a top view of a second filter wheel.
Figure 40:
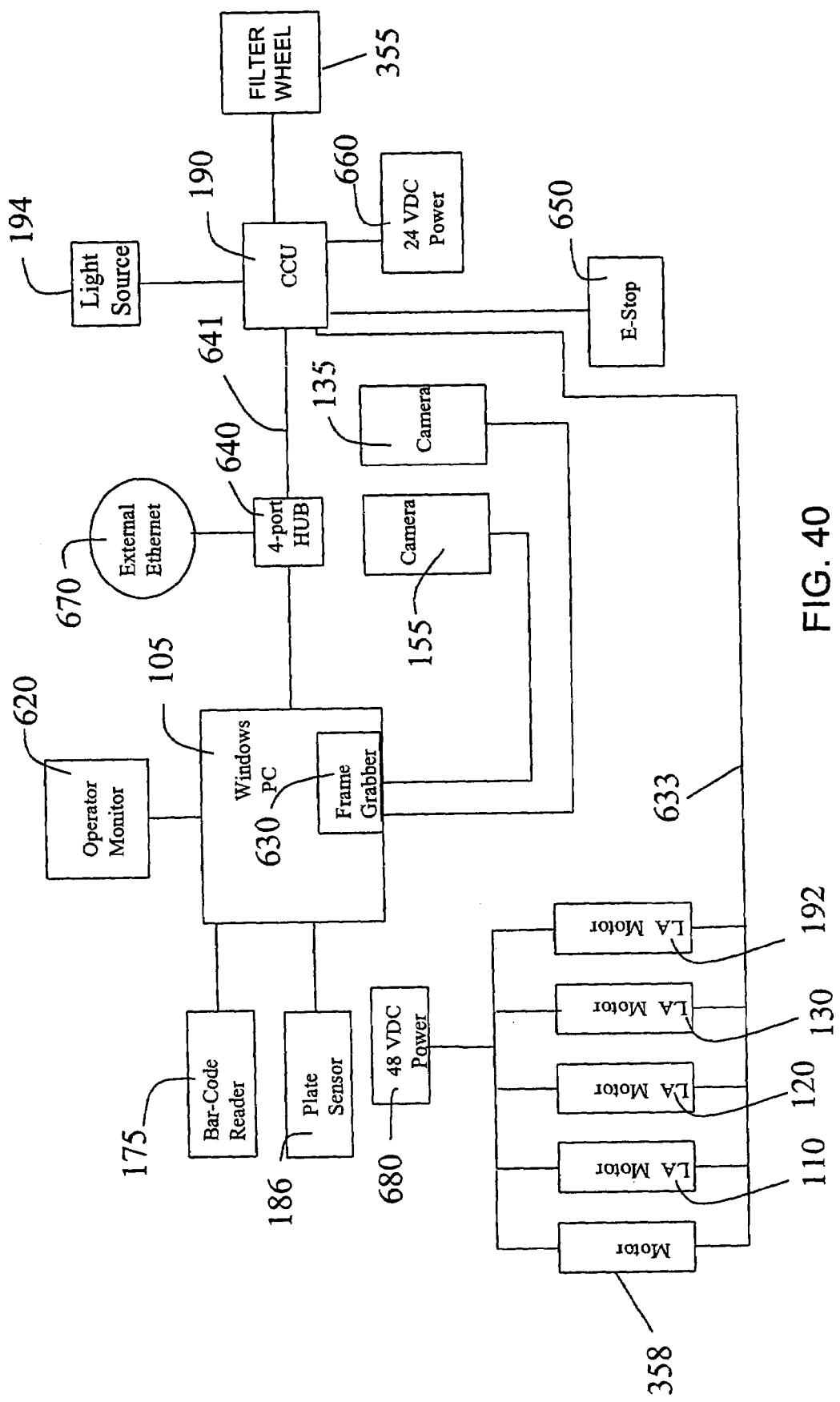
FIG. 40 shows the connectivity of another preferred embodiment.

Linear polarized filter 352 is rotationally mounted above light guide 195 such that light from light guide 195 can be polarized linearly at a programmable angle before it transits through micro-well plate 125A. Polarizer drive belt 356 (top view shown in FIG. 38) rotates polarized filter 352 about a vertical axis. Polarization drive belt 356 is driven by motor 358. Motor 358 is controlled by CCU 190 (FIG. 40). Second filter 354 (top view shown in FIG. 39) is positioned above micro-well plate 125A such that light transiting through micro-well plate 125A goes through second filter 354 before it goes into the camera zoom lens 145. Second filters 354 are mounted on filter wheel apparatus 355. Filter wheel apparatus 355 rotates the operator selected second filter 354 into position under the zoom lens 145. The selected second filter 354 is preferably either a red, green or blue dichroic filter. Preferably, individual images taken through the red, green and blue second filters are combined to form a true color image.

False Color Image

In addition to the true color images that may be formed using red, green, and blue filters 354, a false color (also called a pseudo color) image may be formed by taking three individual images using linear polarized filter 352 at three different polarization angles with respect to a second filter. In this preferred embodiment, a linear polarized filter is substituted for the dichroic second filters 354 discussed above. For example, the polarized axis may be at 90 degrees to each other, and at plus and minus 45 degrees to each other. The three images are then called red, green, and blue and a false color image is produced. If the crystal exhibits any polarization rotation effects, then a very colorful image results. This pseudo color image is useful in detecting very small and fine crystals from the image background material. Other polarizing angles may be selected as well.

In the preferred embodiment, light guide 195 is model #A08925 fiber-optic backlight available from Aegis Electronics of Carlsbad. Calif. Light source 194 is a Dolan-Jenner Model-PL-900 available from Edmund Industrial Optics, Barrington, N.J. First polarized filter 352, second filter 354 (including the linear polarized filters, and the dichroic red, green, blue filters) are available from Edmund Industrial Optics, Barrington, N.J. Filter wheel 355 is model FW1 available from Integrated Scientific Imaging Systems, Inc of Santa Barbara, Calif.

LED (Light Emitting Diode) Array Light Source

In another preferred embodiment, an array of LEDS is used to illuminate micro-well plates as they are positioned underneath lens 165 of camera 155. The utilization of an LED array provides several advantages, including: (1) a lifetime on the order of 10,000 hours compared to the Dolan-Jenner light source that uses a 150 watt halogen-filled incandescent bulb with a life on the order of several hundred hours, (2) an emission spectrum that is relatively constant as intensity varies over an order of magnitude compared to the incandescent source which has an emission spectrum which varies substantially with intensity, (3) switching on-off times measured in milliseconds or less compared to much longer on-off times for an incandescent bulb, (4) overall intensity at over 5 times that of a 150 watt halogen bulb and flat panel, and (5) a lower power consumption with the 600 LED array consuming less than 50 watts, and (6) more light directed in the direction perpendicular to the array compared to the diffuse flat panel driven by the incandescent bulb.

Figure 56A:
FIGS. 56A-57B show photographs demonstrating the clarity of LED illumination.

LEDS provide an optimum light source. For example, FIG. 56A is a photograph showing a magnified image of wells E11 and F11 of micro-well plate 125A. The photograph taken in FIG. 56A utilized a halogen filled incandescent bulb as a light source. The drop within well E11 is approximately 1.2 millimeters across.

Figure 56B:
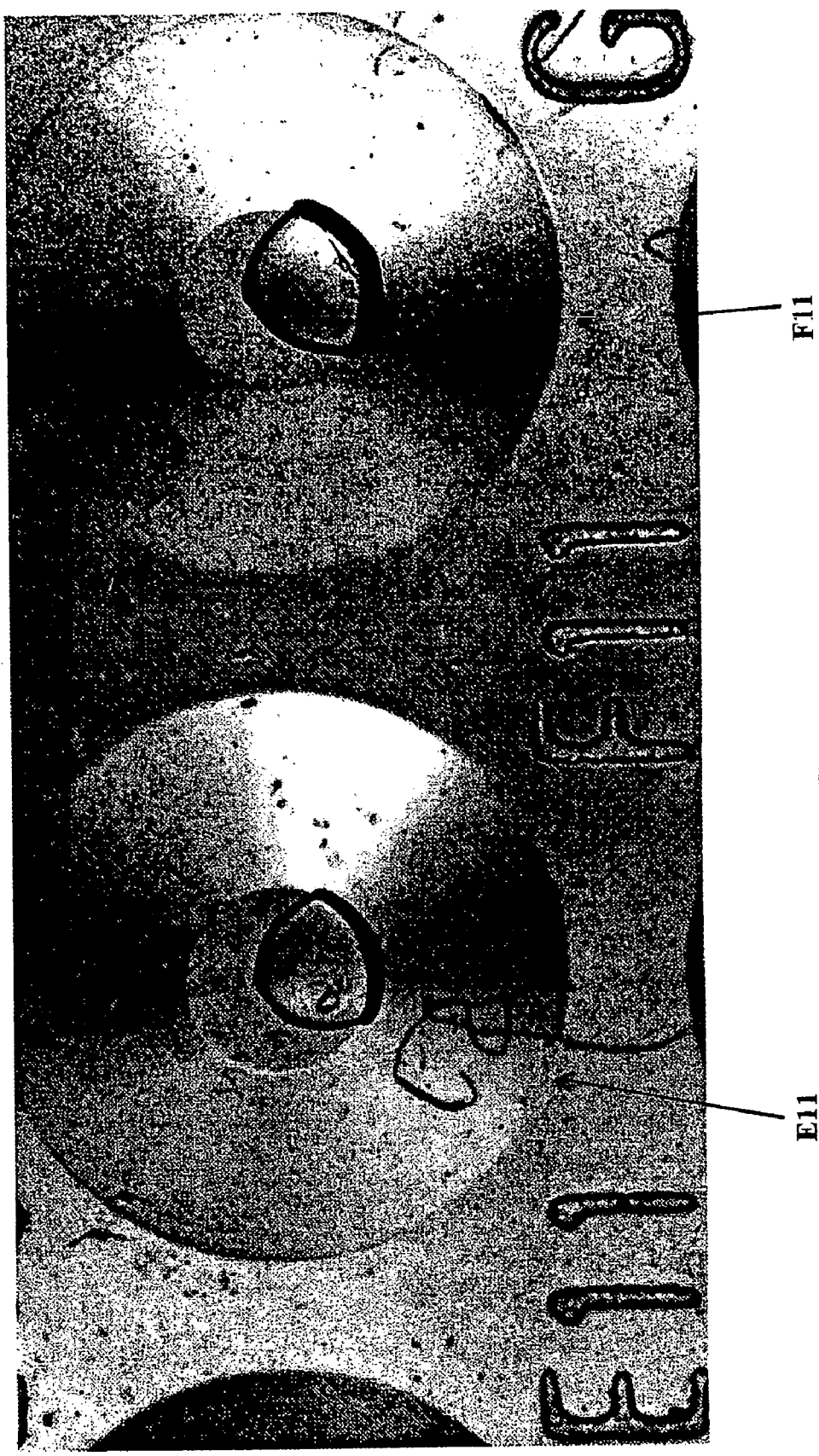

In comparison, FIG. 56B shows the same wells E11 and F11 of micro-well plate 125A. The photograph taken in FIG. 56B utilized an LED array similar to that shown in FIG. 43 as a light source. As is clearly demonstrated by FIGS. 56A and FIG. 56B, the LED array provides a light source that is far more intense and directed. The result is better clarity in the image.

Figure 57A:
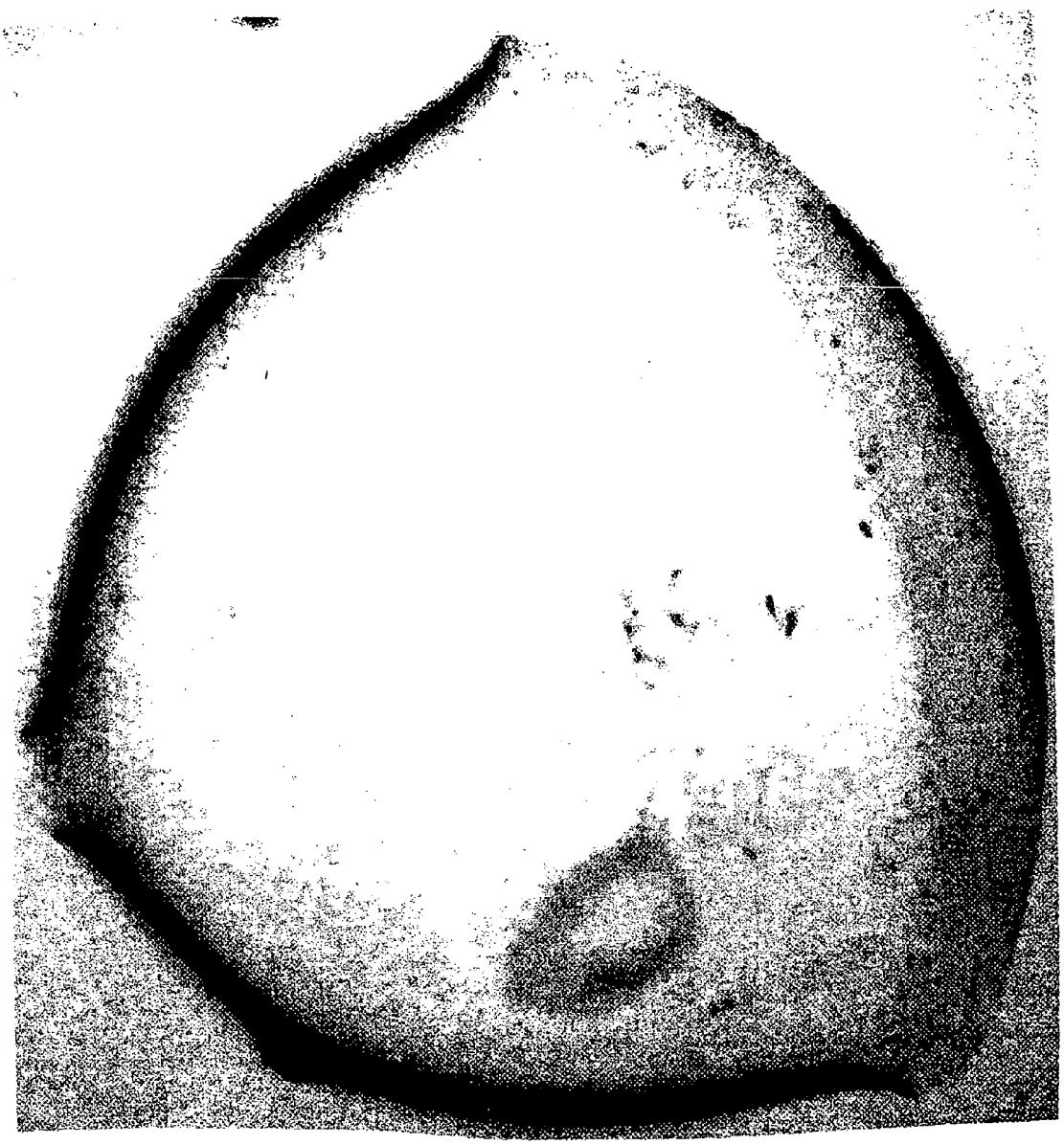

To further illustrate the improvement to the image, FIG. 57A is a photograph taken at an even higher magnification than the photograph shown in FIG. 56A. FIG. 57A shows details of the drop containing microcrystals in well E11 of micro-well plate 125A. The photograph taken in FIG. 57A utilized the halogen filled incandescent bulb used in FIG. 56A.

Figure 57B:

In contrast, FIG. 57B shows the same well E11 as in FIG. 57A. However, in FIG. 57B the LED array of FIG. 56B was used as a light source. By using the LED array light source, it was possible to achieve imaging of the fainter microcrystals in the drop.

A Preferred LED Array Light Source

Figure 44:
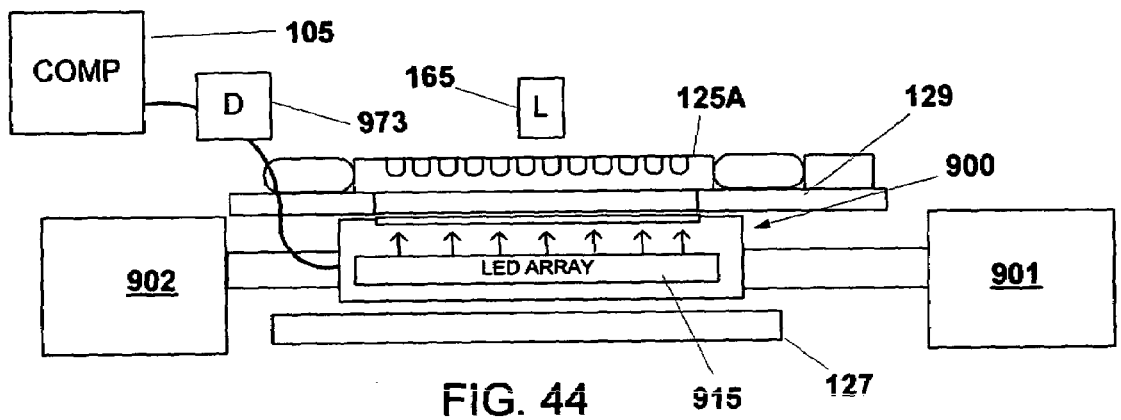
FIG. 44 shows another preferred embodiment of the present invention.

As shown in FIG. 44, LED array light source 900 is mounted between fixture plate 129 and plate 127 and LED array light source 900 is providing illumination for micro-well plate 125A. LED array light source 900 is supported by side supports 901 and 902.

Figure 41:
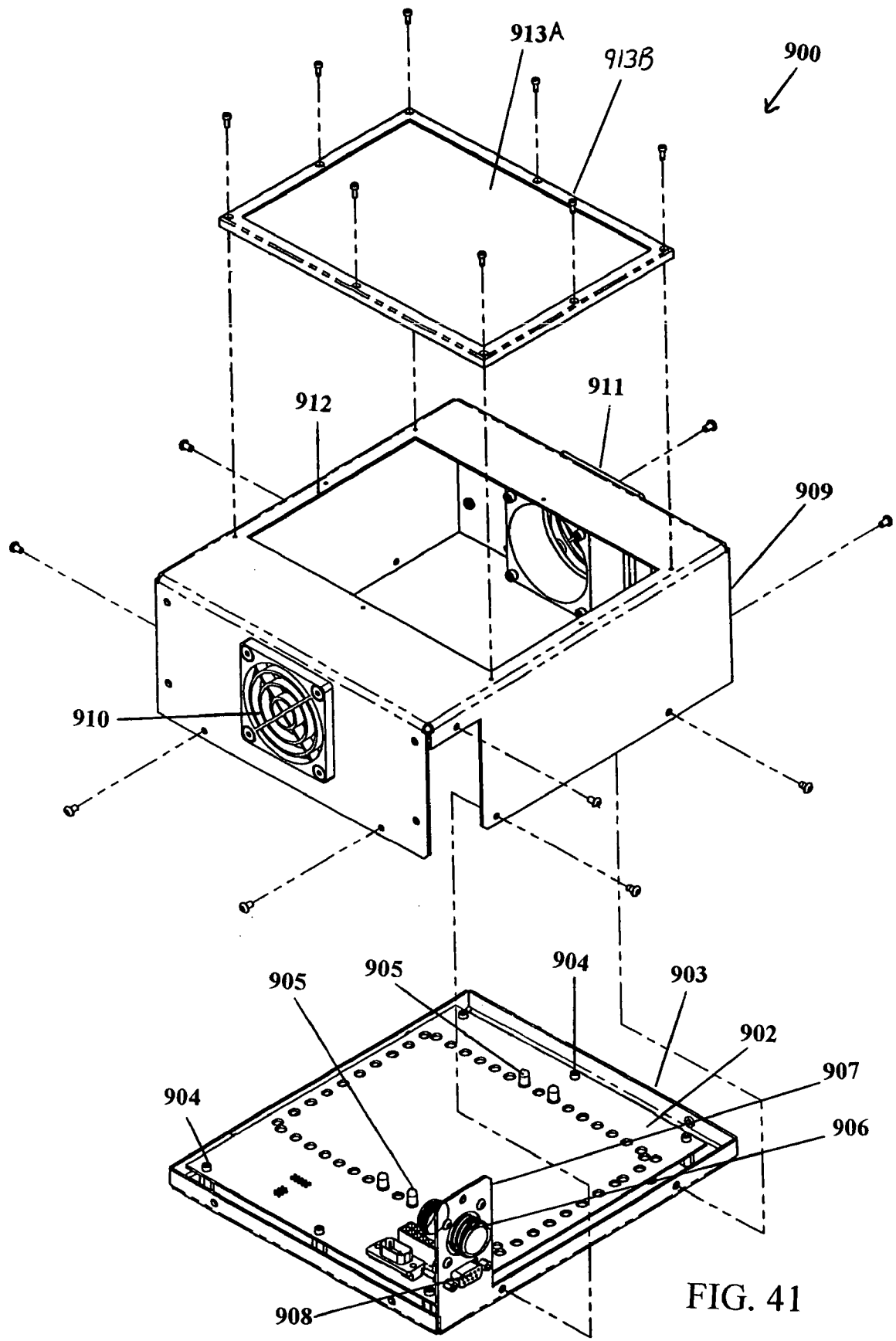
FIG. 41 shows an exploded view of another preferred embodiment of the present invention.
Figure 42:
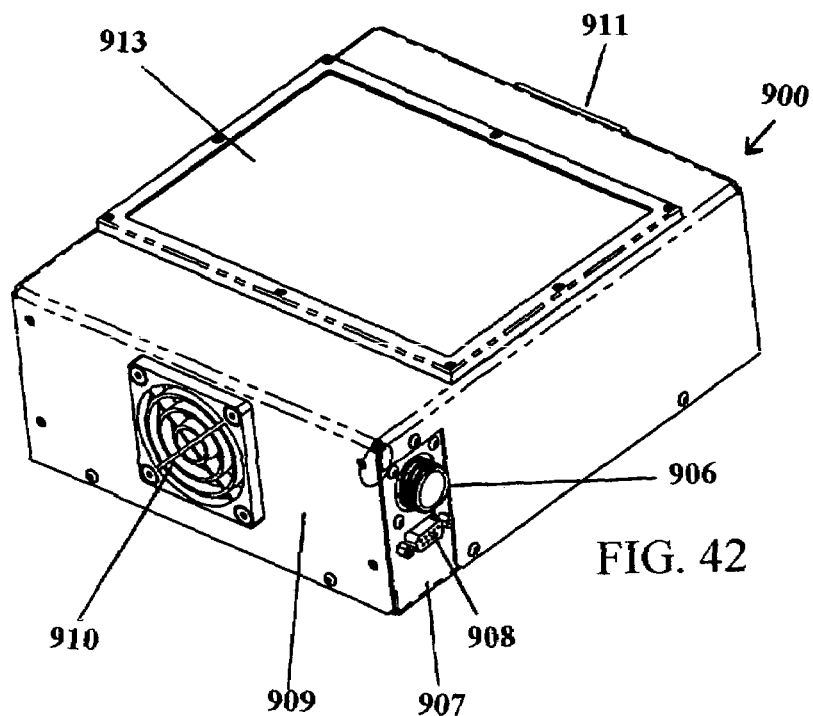
FIG. 42 shows a perspective view of the preferred embodiment shown in FIG. 41.

FIG. 41 shows an exploded view of a preferred LED array light source 900 and FIG. 42 shows a perspective view of LED array light source 900. PCB (printed circuit board) 902 is mounted to bottom section 903 via screws 904. LEDS 905 are inserted into PCB 902 as shown. LEDS are available from many sources, however preferred LEDS 905 are white-light LEDS available from Brite-LED Optoelectronics, Valrico, Fla., Part No. -BL-LBUW5B20C-NB.

Figure 43:
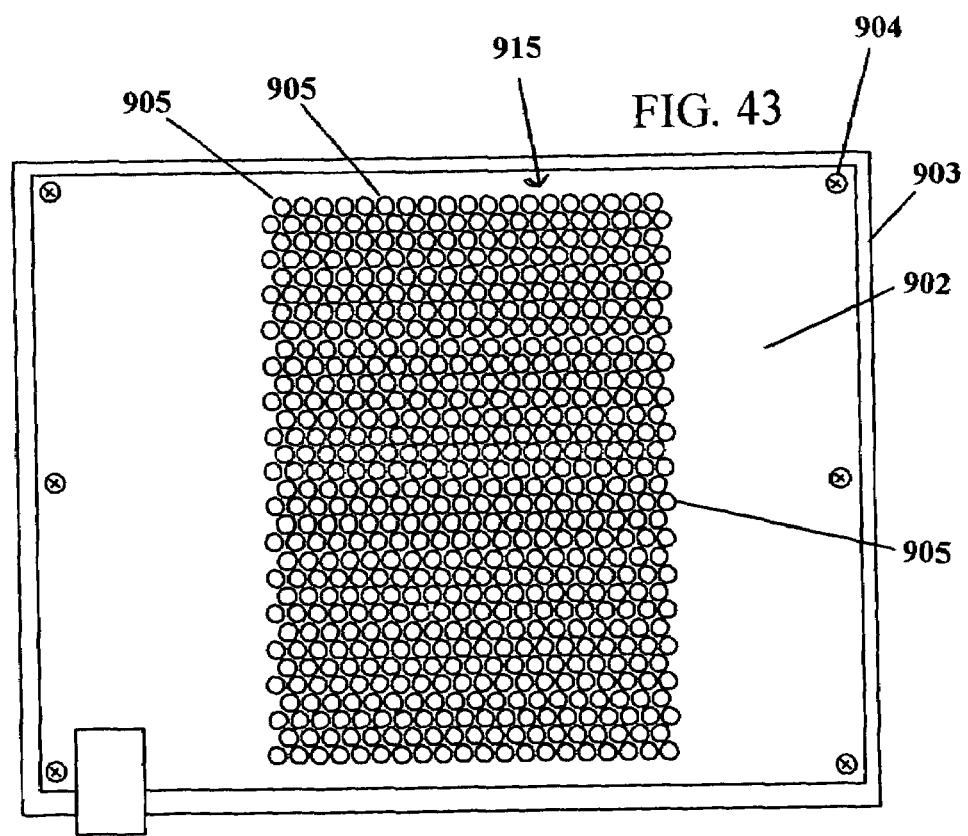
FIG. 43 shows a top view of an LED array.

Please note that FIG. 41 shows only a small portion of the total number of LEDS 905 mounted to PCB 902. FIG. 43 shows a top view of a preferred array 915 of LEDS 905 mounted to PCB 902. In the preferred embodiment, LED array 915 includes 624 LEDS 905. Power connector 906 and control connector 908 are both mounted to extension 907.

In FIG. 41, Fan 910 and filter 911 are both mounted to upper section 909. Also, upper section 909 has cut-out section 912. Diffusing panel 913A and mounting frame 913B are mounted over cut-out section 912, as shown. In the preferred embodiment, diffusing panel 913A is a glass panel that has been sandblasted on one side with 120 grit spray so that the sandblasted side is facing the array of LEDS. A preferred diffusing panel is available from Edmund Industrial Optics of Barrington, N.J., U.S.A., as model F02-146. Diffusing panel 913A diffuses the light from LED array 915 so that a more uniformly distributed light source is presented to the micro-well plate being inspected.

Operation of the LED Array Light Source

Preferably, LED array light source 900 is controlled by computer 105 (FIG. 44). LEDS 905 that are in the area below lens 165 are automatically turned "on" by computer 105. Likewise, as lens 165 moves away from an area of lighted LEDS 905, computer 105 automatically turns "off" the lighted LEDS 905. The overall result is that as the position of lens 165 is changed relative to micro-well plate 125A, a pattern of lighted LEDS 905 underneath lens 165 follows the position of lens 165.

By selectively turning "on" certain LEDS and selectively turning "off" the other LEDS, light is being applied only to the area needed (i.e., the area in the vicinity of lens 165). By controlling the light in this fashion, the user minimizes the amount of light and heat that is applied to the wells that are not being inspected. This is important because excessive light and heat can adversely affect the growth of the microcrystals in the micro-well plate.

Variation of LED Intensity

The current to the LEDS in the array is controlled by computer 105 so that the intensity of the array is programmable. By varying the intensity, customized lighting applications can be programmed. In the preferred embodiment, the intensity of the lighted LEDS is varied by appropriately programming computer 105. Computer 105 then controls programmable driver 973 (FIG. 44) to drive the LEDS so that the desired intensity is displayed. As the current to the LEDS increases, the intensity of light generated by the LEDS increases. The illumination level can vary from "off" to full current "on".

Sequence Depicting Operation of Preferred Embodiment

Figure 45:
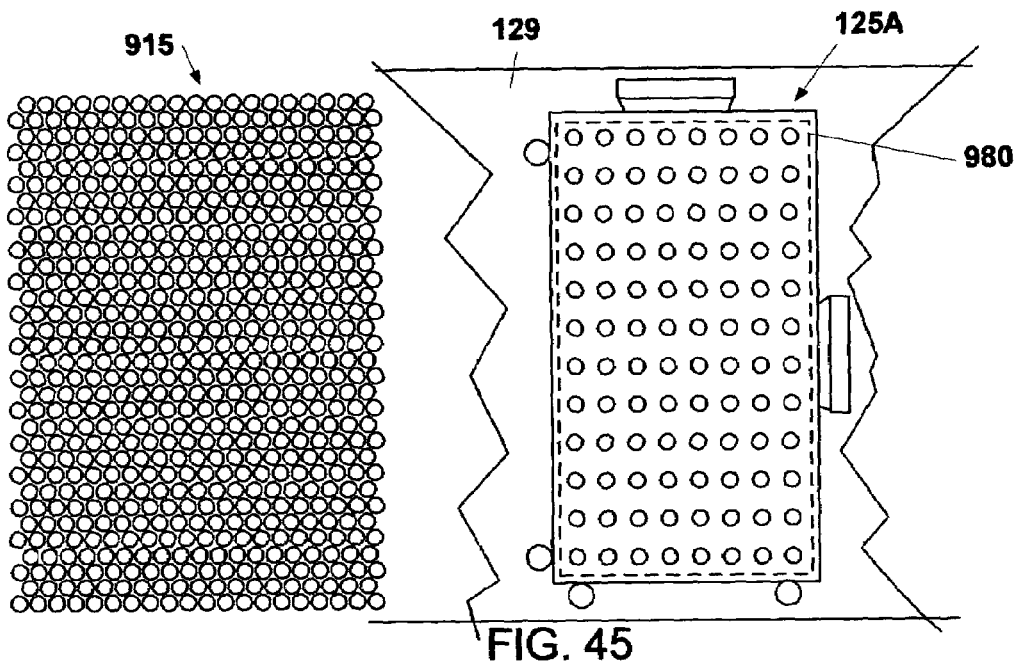

FIG. 45 shows micro-well plate 125 positioned on fixture plate 129. LED array 915 is positioned underneath and to the left of micro-well plate 125A. (Please note, in FIG. 45, diffusing panel 913A (FIG. 42) and is not shown so that the operation of LED array light source 900 can better be explained. Also, in FIGS. 46-50B, other elements of this preferred embodiment, such as fixture plate 129, are not shown so that the operation of LED array light source 900 can better be explained.)

Figure 46A:
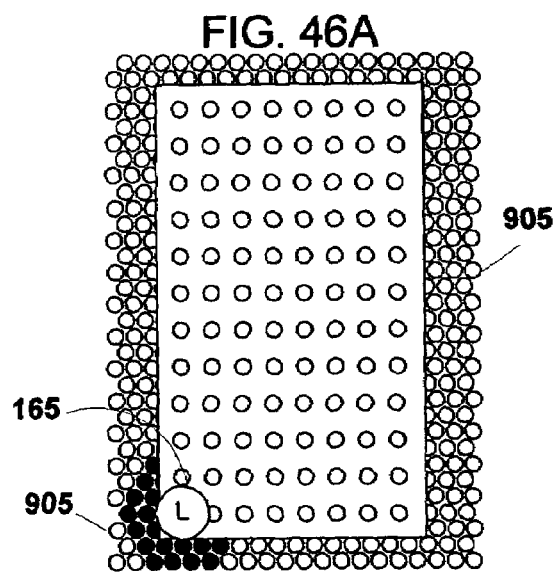
Figure 46B:
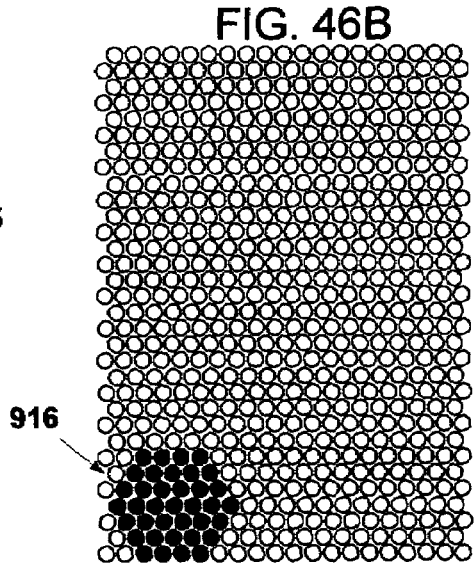

In FIG. 46A, computer 105 has positioned lens 165 so that it is above the lower, left-corner well of micro-well plate 125A. Also, computer 105 has turned on a group of LEDS 905 underneath lens 165. FIG. 46B shows more clearly pattern 916 of the LEDS that have been turned on. LEDS that are "on" are shown in FIGS. 46A and 46B as being all black. A preferred pattern 916 has the approximate shape of a hexagon. Preferably, the center of pattern 916 is positioned underneath the center of lens 165 at the lower, left-corner well of micro-well plate 125A.

Figure 47A:
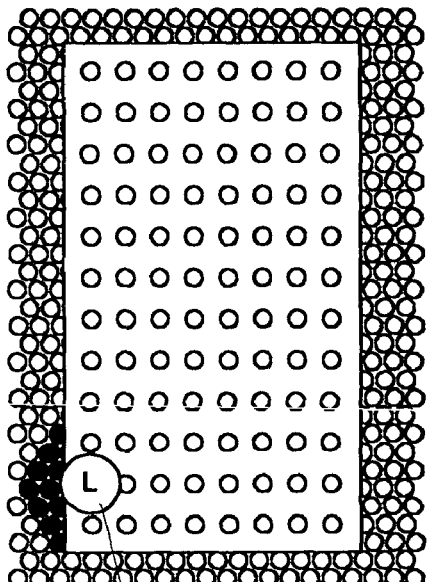
Figure 47B:
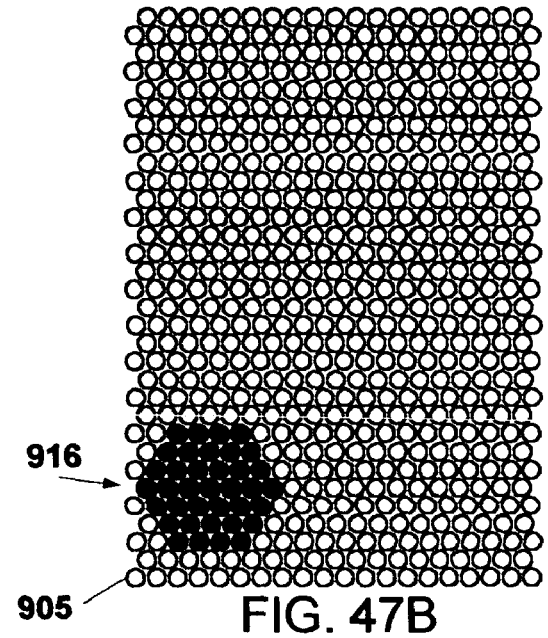

In FIG. 47A, computer 105 has moved lens 165 one position upward so that it is above the next well up from the lower, left-corner well of micro-well plate 125A. Also, computer 105 has turned on a group of LEDS 905 underneath lens 165 at its new position. FIG. 47B shows more clearly the new position of pattern 916.

Figure 48A:
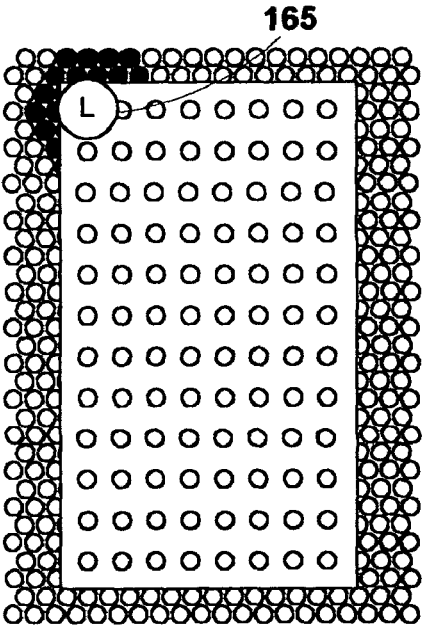
Figure 48B:
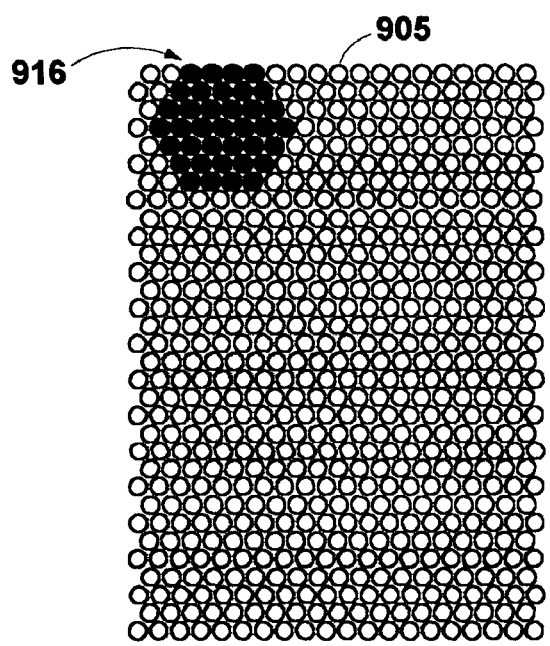

In a similar manner, computer 105 continues to move lens 165 and pattern 916 upward from well to well. Until, as shown in FIG. 48A, computer 105 has moved lens 165 upward so that it is above the upper, left-corner well of micro-well plate 125A. FIG. 48B shows more clearly the respective position of pattern 916 as shown in FIG. 48A.

Figures 49A, 49B, 50A, 50B:
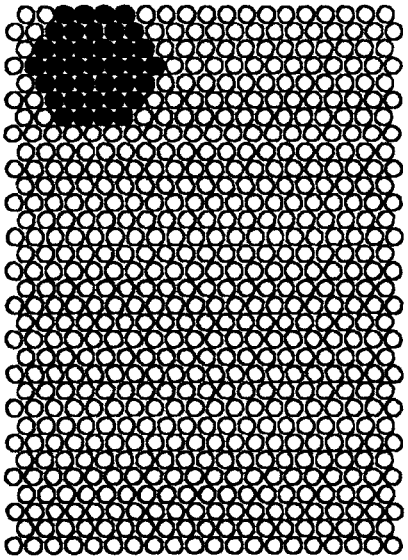

In FIG. 49A, computer 105 has moved lens back to the position shown in FIG. 46A. Also, fixture plate 129 (FIGS. 44 and 45) has moved micro-well plate 125A one position to the left. Therefore, lens 165 is now above the well just to the right of the lower, left-corner well of micro-well plate 125A. Also, computer 105 has turned on a group of LEDS 905 underneath lens 165 at its new position. FIG. 49B shows more clearly the new position of pattern 916.

In a similar manner, computer 105 continues to move lens 165, pattern 916 and fixture plate 129 so that lens 165 and pattern 916 go from well to well. Until, as shown in FIG. 50A, lens 165 is above the upper, right-corner well of micro-well plate 125A. FIG. 50B shows more clearly the new position of pattern 916.

LED Array Embodiment where Micro-well Plate Remains Stationary

Figure 51A:
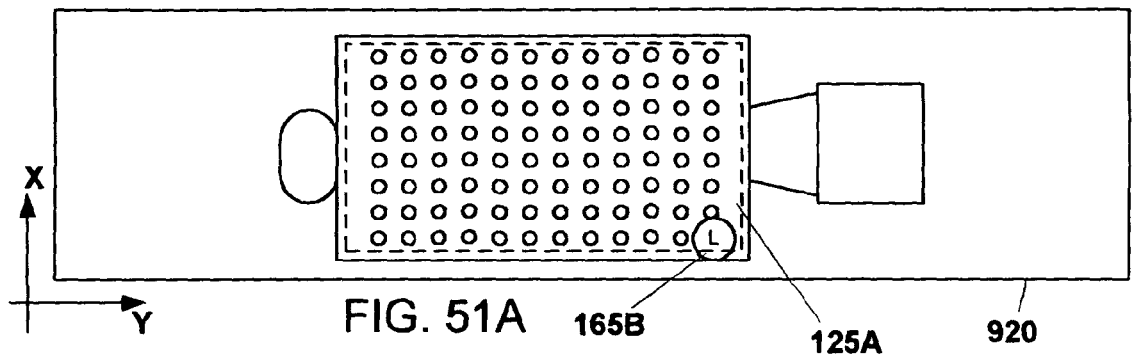
FIGS. 51A-51B show another preferred embodiment of the present invention.

FIG. 51A shows a top view of another preferred embodiment of the present invention. Micro-well plate 125A remains stationary on platform 920. Lens 165B is robotically controlled via computer 105 and is capable of vertical movement and movement in the x and y directions.

Figure 51B:
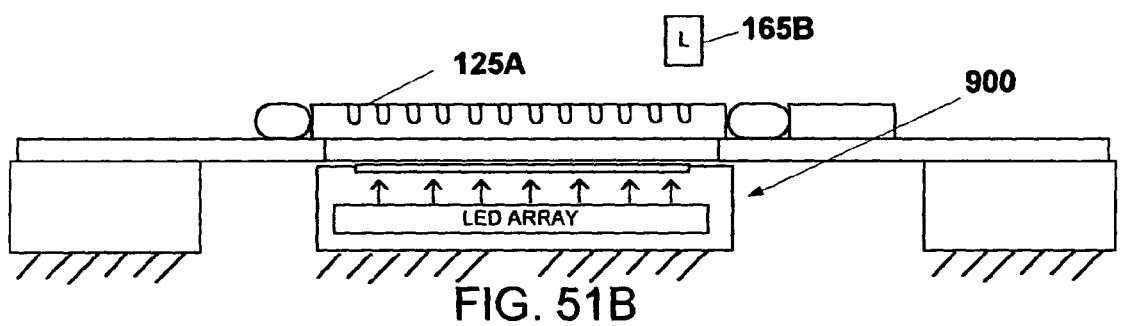

As shown in FIG. 51B, LED array light source 900 is positioned under micro-well plate 125A and is also stationary. In the preferred embodiment shown in FIGS. 51A and 51B, computer 105 controls the movement of lens 165. Computer 105 also moves pattern 916 under micro-well plate 125A by turning LEDS 905 "on" and "off" in a fashion similar to that described above.

Figure 52A:
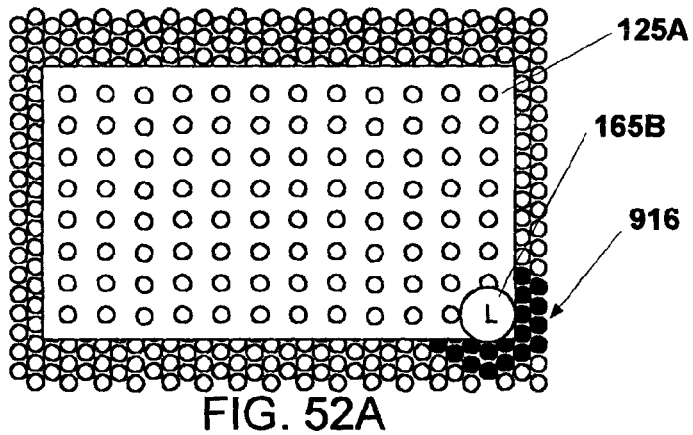
FIGS. 52A-53B illustrate the operation of the preferred embodiment shown in FIGS. 51A-51B.
Figure 52B:
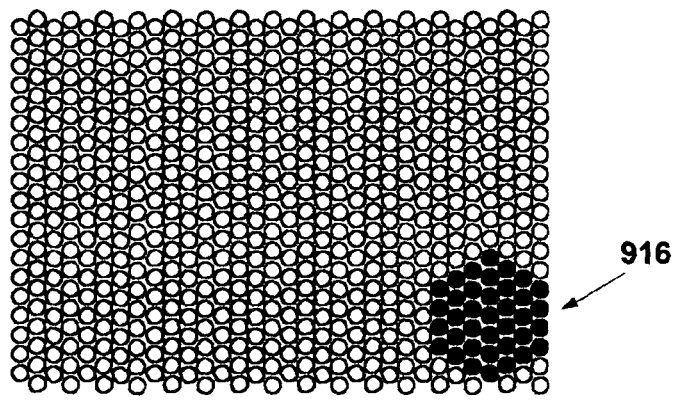

For example, in FIG. 52A computer 105 has moved lens 165 so that it is positioned above the lower, right-corner well of micro-well plate 125A. Pattern 916 of LEDS 905 is centered underneath lens 165. FIG. 52B shows more clearly the new position of pattern 916.

Figure 53A:
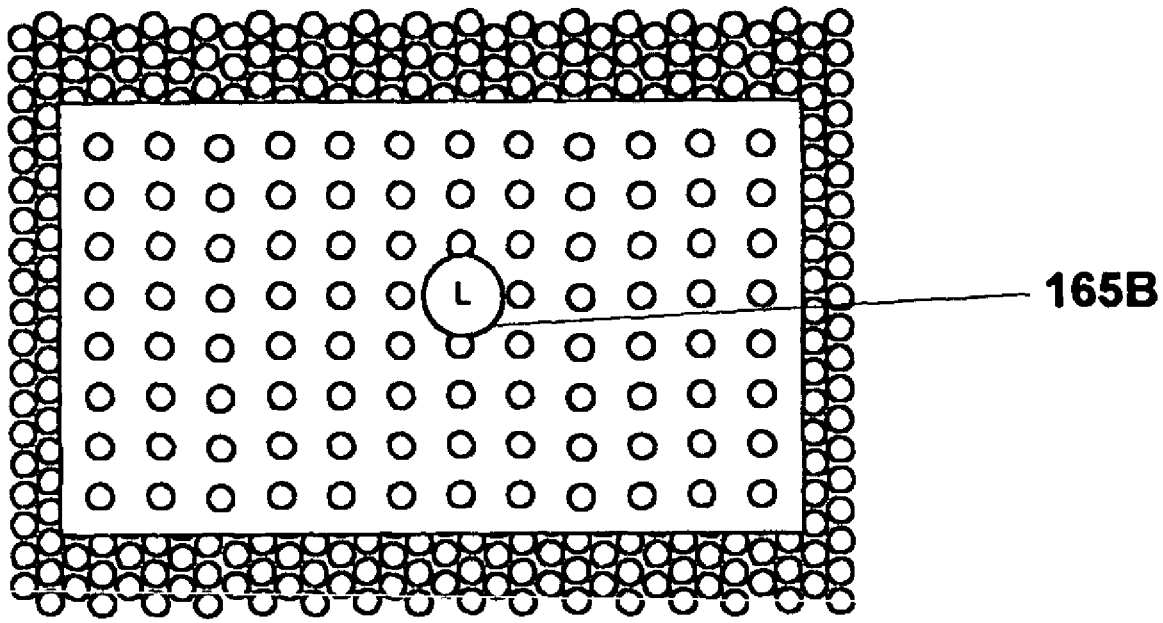
Figure 53B:
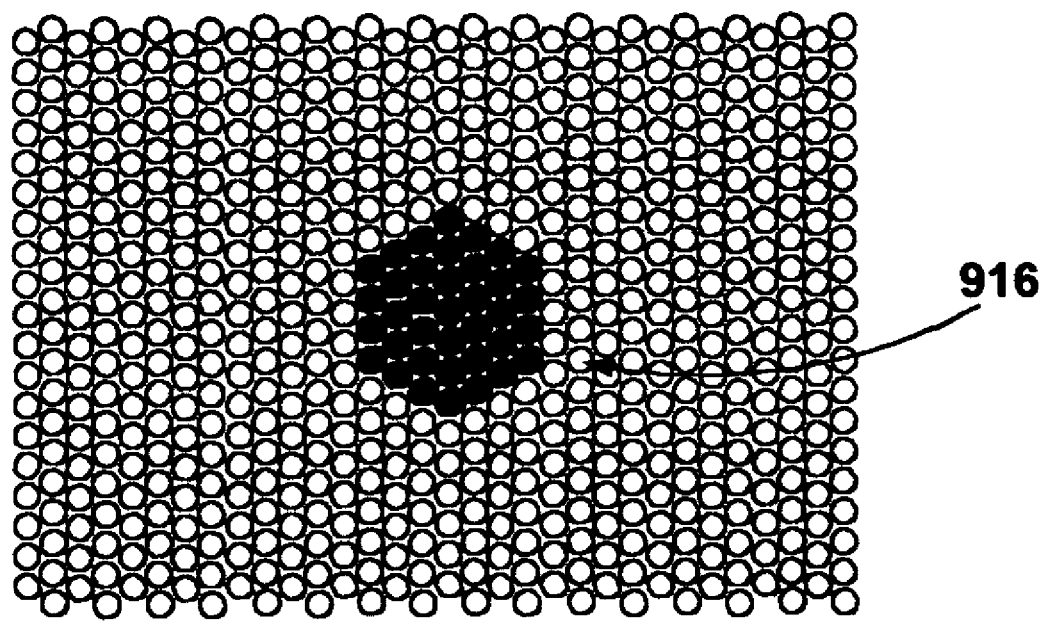

In FIG. 53A, computer 105 has moved lens 165 in the "x" and "y" direction so that it is positioned above a well more towards the center of micro-well plate 125A. Computer 105 has turned certain LEDS "on" and other LEDS "off" so that the effect is that pattern 916 is underneath lens 165. FIG. 53B shows more clearly the new position of pattern 916.

In this manner, computer 105 can move lens 165 so that it is over any well of micro-well plate 125A. Moreover, computer 105 can turn certain LEDS "on" and other LEDS "off" so that the effect is that pattern 916 will always follow the movement of lens 165 so that it is underneath lens 165.

LED Array Embodiment where Lens Remains Stationary with Respect to the "X" and "Y" Axis FIGS. 54A-54E show another preferred embodiment of the present invention. Robotic arms 930 and 931 grip platform 932. Micro-well plate 125A rests on platform 932. Lens 165C is positioned above micro-well plate 125A and is preferably capable of being raised and lowered. However, it remains stationary with respect to the x and y axis. Robotic arms 930 and 931 are controlled by computer 105 and are capable of moving platform 932 along the x and y axis. LED array light source 940 is stationary and is positioned below lens 165C. Light from LED array light source 940 provides illumination upward through cutout portion 941 of platform 932. LED array light source 940 is very similar to LED array light source 900 shown in FIGS. 42 and 43 with the exception being that array 943 is much smaller than array 915 shown in FIG. 43. Array 943 can be smaller because its position is fixed with respect to the x-y position of lens 165C. For example, a preferred array 943 has approximately 100 LEDS 905 compared to the 624 LEDS 905 shown in FIG. 43

In FIG. 54B, lens 165C is above a well towards the center of micro-well plate 125A. In FIGS. 54C-54E, robotic arms 930 and 931 have moved platform 932 in the negative "y" direction and in the negative "x" direction so that lens 165C is above a well towards the upper, right corner of micro-well plate 125A. FIG. 54C shows a side view while FIGS. 54D and 54E show top views. FIG. 54E shows a partially cut away top view of lens 165C above array 943.

In the manner described above, computer 105 can alter the x-y position of platform 932 so that any well in micro-well plate 125A can be positioned between array 943 and lens 165C.

Variation of Pattern Shape in LED Array

Figure 55A:
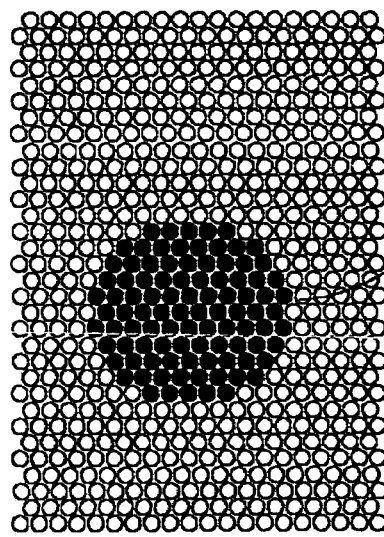
FIGS. 55A-55C show preferred patterns.
Figure 55B:
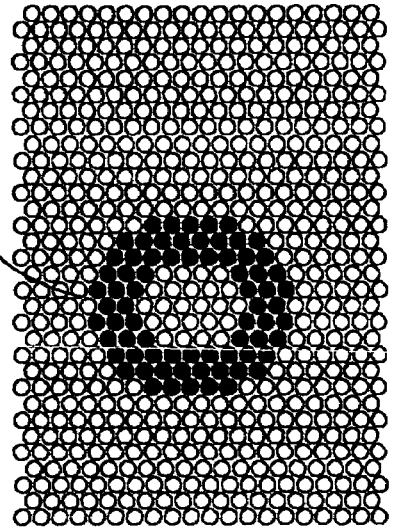

In the above preferred embodiments, pattern 916 was shown as being a hexagon (FIG. 46B). However, computer 105 can be programmed to create a variety of pattern shapes. For example, FIG. 55A shows pattern 960, which is roughly in the shape of a circle. FIG. 55B shows pattern 961, which is roughly donut shaped. Pattern 961 is used for providing dark field illumination. Dark field illumination is used to illuminate the well from the side. Dark field illumination will cause the edges of the crystal being observed to appear light in comparison to the full image.

In addition to the shapes shown in FIGS. 55A and 55B, a variety of other pattern shapes are also possible. For example, computer 105 could be programmed to create a pattern in the shape of a square, rectangle, octagon, pentagon, triangle, or a variety of other shapes.

Variation of Intensity within a Pattern

Figure 55C:
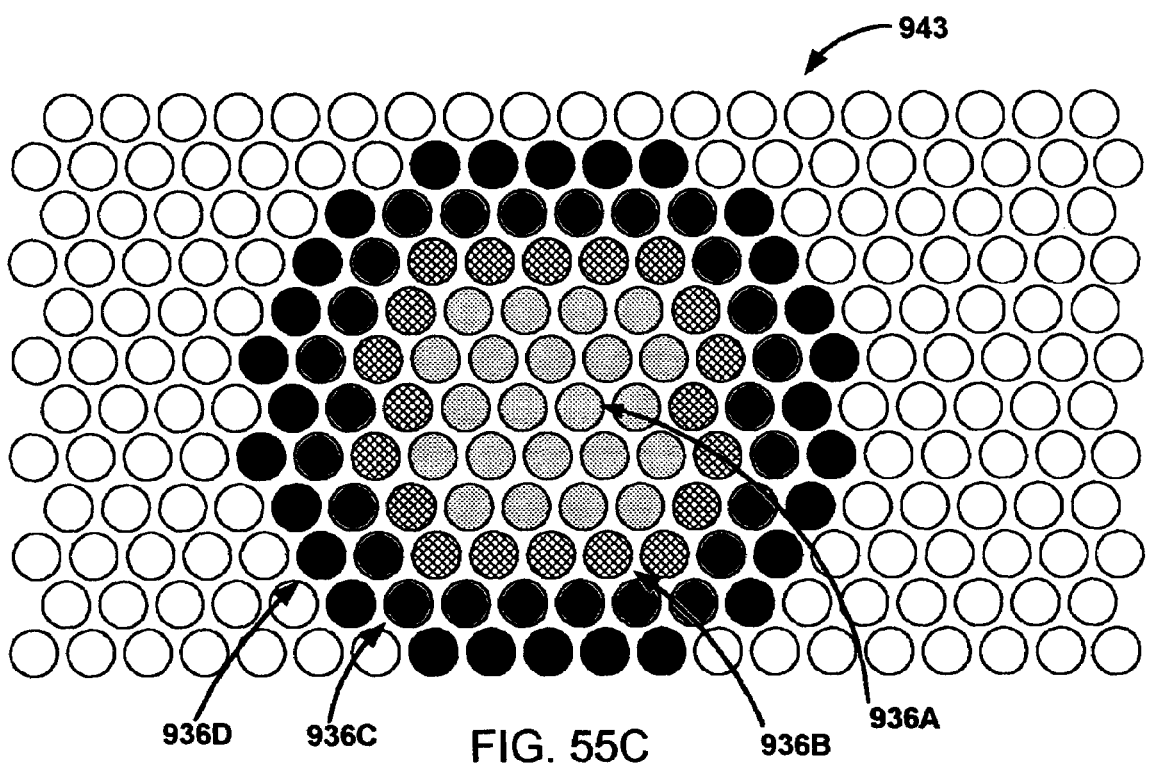

FIG. 55C shows a top view of LED array 943. In this preferred embodiment, computer 105 is programmed to individually control the intensity of the LEDS arranged in four approximately circular zones 936A-936D centered about the center of the array. This provides for patterns that have a symmetrically arranged intensity levels. For example, zone 936A has the lowest level of intensity, zone 936B has an intensity level higher than, zone 936A, zone 936C has an intensity level higher than zone 936B, and zone 936D has the highest level on intensity.

Figure 12:
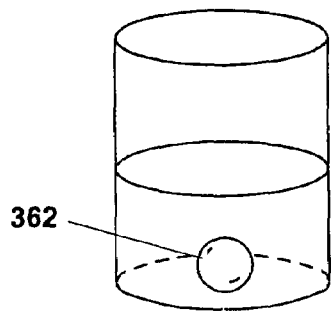
FIG. 12 shows an example of aqueous drop in oil protein crystallization.
Figure 58:
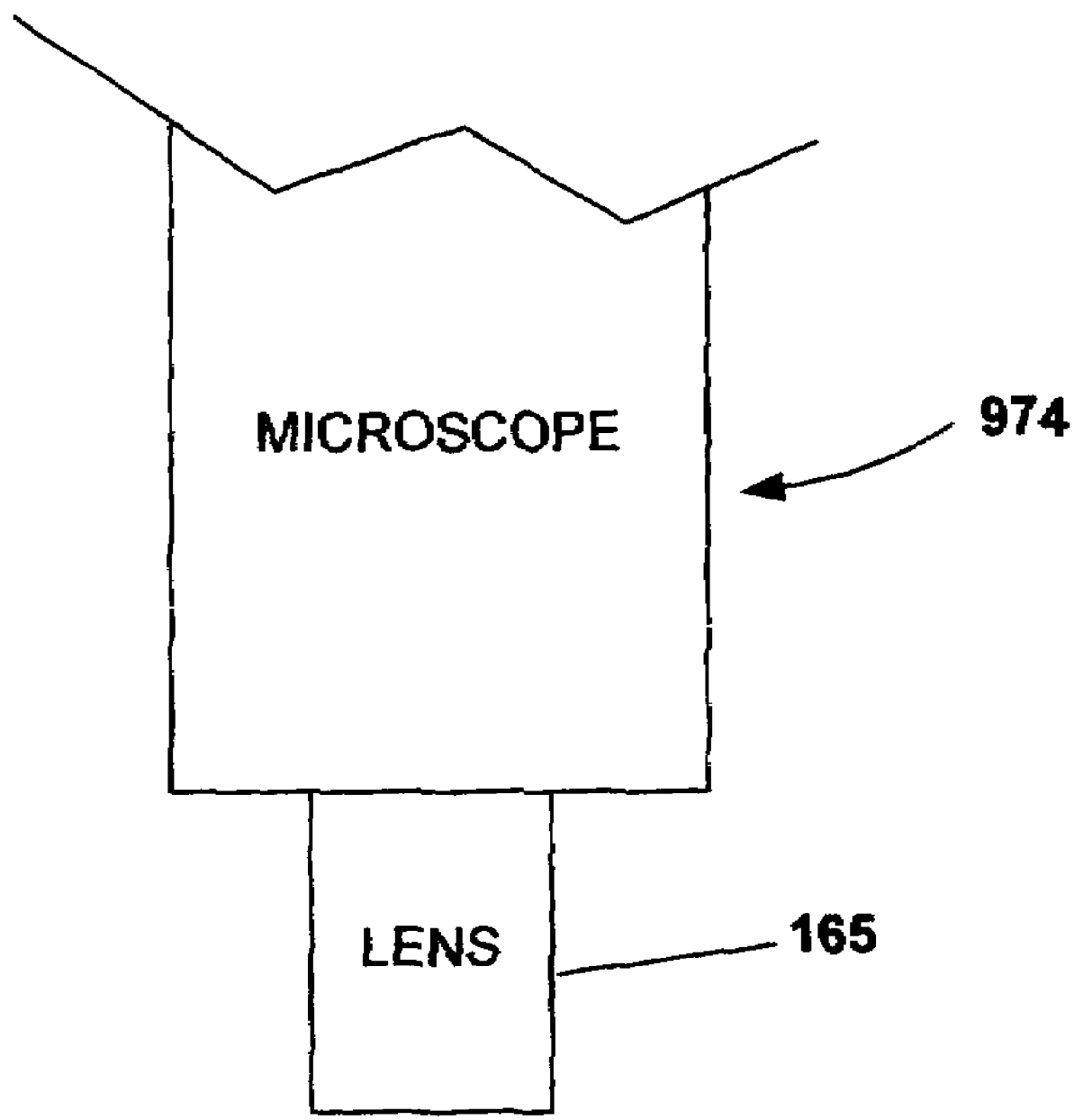
FIG. 58 shows another preferred embodiment of the present invention.

Although the above-preferred embodiments have been described with specificity, persons skilled in this art will recognize that many changes to the specific embodiments disclosed above could be made without departing from the spirit of the invention. For example, an array of LEDS can be advantageously used with specific color output such as Red, Green, or Blue LEDS in addition to the white light LEDS described above. Also, individual LEDS containing red, green, and blue emitters can be utilized to provide any color output as desired when controlled by the control computer. In addition the LEDS can be strobed so that synchronization between the light and imaging apparatus may be obtained. Also, in the embodiments shown in FIGS. 41-57B, it is possible for lens 165 to be attached to either a camera (such as cameras 135 or 155 shown in FIG. 1) or attached to a microscope (such as microscope 974 shown in FIG. 58). Although the above preferred embodiments specifically describe an indexing device in which linear actuators 115, 150, and 160 operate in conjunction to sequentially position protein crystals under cameras 155 and 135, there are a variety of other types of robotic indexing devices that could also be utilized for the same purpose. For example, an indexing device could be built in which the plurality of micro-well plates are kept in a stationary position. The camera lens would be attached to an indexing device that is preferably capable of unrestricted movement in the horizontal plane. The camera lens would be moved sequentially from micro-well to micro-well in the horizontal plane. Once in position over a micro-well, the lens could be raised or lowered in the vertical direction to achieve proper zoom and focus. In another embodiment, an indexing device could be built in which cameras 155 and 135 are kept stationary with respect to horizontal movement. In this embodiment, the plurality of micro-well plates would be preferably placed on a positioning platform that is capable of unrestricted movement in the horizontal plane. In this fashion, the positioning platform could be moved so that each micro-well is sequentially positioned underneath the appropriate camera. As with the previous embodiment, once in position over a micro-well, the lens could be raised or lowered in the vertical direction to achieve proper zoom and focus. Also, although the first preferred embodiment discussed inspecting crystals grown by the hanging drop method, other crystals grown utilizing other methods could be inspected with equal effectiveness. For example, FIG. 12 shows protein crystal growth as a result of aqueous drop in oil protein crystallization. Cameras 135 and 155 focus on the crystals in drop 362. Also, although the above preferred embodiments discussed in detail how the present invention is utilized for inspecting protein crystals inside drops of liquid, the present invention could also be utilized to inspect other types of microscopic specimens. For example, the present invention could be utilized to inspect typical micro-well micro titer plate reactions wherein the quality of the reaction can be judged by the amount and wavelength of fluorescence emitted by the specimen by configuring the system with appropriate light sources, filters, and sensitive cameras as is typical for fluorescence detection. . Also, although the above preferred embodiments disclosed the utilization of two cameras 135 and 155, it would also be possible to have just one camera that is capable of zooming out so that it can focus on the entire well and zooming in so that it can focus on the drop of liquid containing the crystal. In addition, although an area CCD camera is shown, a linear CCD camera combined with moving of the micro-well plate would also work in the present invention. Also, in another preferred embodiment the detents 510 and 520 can be simply spring loaded and not controlled by the computer 105. Although the system is shown that only moves the micro-well plates in one axis and the camera in the other two axes, the invention could likewise be practiced with either the micro-wells moving in two orthogonal axes (such as X and Y) while the camera moves only in the Z-axis or the motion of all three axes be done with the camera system, wherein the micro-well plates are stationary and the system moves above them. These other variations of system design could also require rearrangement of the light source or multiple light sources. Also, other filter types may be substituted for second filter 354. For example, a linearly polarized filter would be very effective. Also, although the above preferred embodiments disclosed specific types of cameras 135 and 155, other CCD cameras may be used in the present invention with less resolution or with greater resolution and still practice the present invention. For example, cameras of 2,000 by 2,000 pixels and even 4,000 by 4000 pixels are commercially available from several vendors. When digitizing these alternative cameras, the digitized image would have the corresponding resolution of the camera. Also, one may practice this invention and digitize to greater gray-scale accuracy than 8-bit and gain advantage if the camera supports the greater bit depth, for example if the camera were cooled to reduce image noise. Therefore, the attached claims and their legal equivalents should determine the scope of the invention.

We claim:

1. A device for inspecting microscopic objects, comprising:
   A) a lens,
   B) a plurality of LEDS arranged in an array underneath said lens, comprising:
      1) lighted LEDS, and
      2) unlighted LEDS, and
   C) at least one computer in communication control of said plurality of LEDS, wherein said at least one computer is programmed to turn on selected LEDS from said plurality of LEDS to form said lighted LEDS, and turn off other selected LEDS from said plurality of LEDS to form said unlighted LEDS, wherein said lighted LEDS form a pattern of lighted LEDS underneath said lens,
wherein said at least one computer is in communication control with said lens, wherein said at least one computer is programmed to move said lens laterally over said plurality of LEDS, wherein said at least one computer is programmed to move said pattern of lighted LEDS so that said pattern of LEDS remains underneath said lens as said lens is moved laterally.

2. The device as in claim 1, wherein said device for inspecting microscopic images is a microscope and wherein said lens is attached to said microscope.

3. The device as in claim 1, wherein said device for inspecting microscopic images is a camera and wherein said lens is attached to said camera.

4. The device as in claim 1, wherein said pattern of lighted LEDS provides dark field illumination.

5. The device as in claim 1, wherein said microscopic objects are a plurality of microscopic crystals.

6. The device as in claim 5, further comprising:
   A) at least one camera attached to said lens, and
   B) an indexing device for sequentially placing said microscopic crystals in camera-view of said lens,
wherein said at least one computer is programmed to control said indexing device and said at least one camera, wherein said at least one computer is programmed to receive from said at least one camera images of said plurality of microscopic crystals, wherein said at least one computer is programmed to classify said plurality of microscopic crystals.

7. The device as in claim 6, further comprising a computer monitor, wherein an operator interfacing with said at least one computer manually inputs a score to classify said plurality of microscopic crystals after observing said plurality of microscopic crystals on said computer monitor.

8. The device as in claim 6, wherein said at least one computer automatically classifies said plurality of microscopic crystals after receiving said images.

9. The device as in claim 1, wherein said computer is further programmed to vary the intensity level of said plurality of LEDS.

10. The device as in claim 1, wherein said intensity level is variable from off to full current on.

11. The device as in claim 1, wherein said pattern of lighted LEDS comprises at least two intensity levels.

12. A device for inspecting microscopic objects, comprising:
A) a lens,
B) a plurality of LEDS arranged in an array underneath said lens, comprising:
 1) lighted LEDS, and
 2) unlighted LEDS, and
C) at least one computer in communication control of said plurality of LEDS, wherein said at least one computer is programmed to turn on selected LEDS from said plurality of LEDS to form said lighted LEDS, and turn off other selected LEDS from said plurality of LEDS to form said unlighted LEDS, wherein said lighted LEDS form a pattern of lighted LEDS underneath said lens,
wherein said lens and said plurality of LEDS move laterally relative to each other, wherein said at least one computer is programmed to move said pattern of lighted LEDS so that said pattern of LEDS remains underneath said lens during said relative lateral movement.

13. A device for inspecting microscopic objects, comprising:
A) a lens means,
B) an array means comprising a plurality of LEDS, said LEDS comprising;
 1) lighted LEDS, and
 2) unlighted LEDS, and
C) at least one computer means in communication control of said array means, wherein said at least one computer means is programmed to turn on selected LEDS from said plurality of LEDS to form said lighted LEDS, and turn off other selected LEDS from said plurality of LEDS to form said unlighted LEDS, wherein said lighted LEDS form a pattern of lighted LEDS underneath said lens,
wherein said at least one computer means is in communication control with said lens means, wherein said at least one computer means is programmed to move said lens means laterally over said array means, wherein said at least one computer means is programmed to move said pattern of lighted LEDS so that said pattern of LEDS remains underneath said lens means as said lens means is moved laterally.

14. The device as in claim 13, wherein said device for inspecting microscopic images is a microscope means and wherein said lens means is attached to said microscope means.

15. The device as in claim 13, wherein said device for inspecting microscopic images is a camera means and wherein said lens means is attached to said camera means.

16. The device as in claim 13, wherein said pattern of lighted LEDS provides dark field illumination.

17. The device as in claim 13, wherein said microscopic objects are a plurality of microscopic crystals.

18. The device as in claim 17, further comprising:
A) at least one camera means attached to said lens, and
B) an indexing means for sequentially placing said microscopic crystals in camera-view of said at least one camera means,
wherein said at least one computer means is programmed to control said indexing means and said at least one camera means, wherein said at least one computer means is programmed to receive from said at least one camera means images of said plurality of microscopic crystals, wherein said at least one computer means is programmed to classify said plurality of microscopic crystals.

19. The device as in claim 18, further comprising a computer monitor means, wherein an operator interfacing with said at least one computer means manually inputs a score to classify said plurality of microscopic crystals after observing said plurality of microscopic crystals on said computer monitor means.

20. The device as in claim 18, wherein said at least one computer means automatically classifies said plurality of microscopic crystals after receiving said images.

21. The device as in claim 13, wherein said computer means is further programmed to vary the intensity level of said LEDS.

22. The device as in claim 13, wherein said intensity level is variable from off to full current on.

23. The device as in claim 13, wherein said pattern of lighted LEDS comprises at least two intensity levels.

24. A device for inspecting microscopic objects comprising:
A) a lens means,
B) an array means comprising a plurality of LEDS, said LEDS comprising:
 1) lighted LEDS, and
 2) unlighted LEDS, and
C) at least one computer means in communication control of said array means, wherein said at least one computer means is programmed to turn on selected LEDS from said plurality of LEDS to form said lighted LEDS, and turn off other selected LEDS from said plurality of LEDS to form said unlighted LEDS, wherein said lighted LEDS form a pattern of lighted LEDS underneath said lens,
wherein said lens means and said array means move laterally relative to each other, wherein said at least one computer means is programmed to move said pattern of lighted LEDS so that said pattern of LEDS remains underneath said lens means during said relative lateral movement.

* * * * *